US007201911B1

(12) United States Patent
Yanagi et al.

(10) Patent No.: US 7,201,911 B1
(45) Date of Patent: *Apr. 10, 2007

(54) CLONED GENOMES OF INFECTIOUS HEPATITIS C VIRUSES AND USES THEREOF

(75) Inventors: Masayuki Yanagi, Rockville, MD (US); Jens Bukh, Bethesda, MD (US); Suzanne U. Emerson, Rockville, MD (US); Robert H. Purcell, Boyds, MD (US)

(73) Assignee: United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,454

(22) Filed: Sep. 14, 2000

Related U.S. Application Data

(62) Division of application No. 09/014,416, filed on Jan. 27, 1998, now Pat. No. 6,153,421.

(60) Provisional application No. 60/053,062, filed on Jul. 18, 1997.

(51) Int. Cl.

| | |
|---|---|
| ***A61K 39/12*** | (2006.01) |
| ***A61K 30/70*** | (2006.01) |
| ***A61K 39/295*** | (2006.01) |
| ***C12N 15/00*** | (2006.01) |
| ***C12N 5/00*** | (2006.01) |
| ***C12N 5/08*** | (2006.01) |
| *A61K 39/00* | (2006.01) |

(52) U.S. Cl. .............................. 424/218.1; 424/204.1; 424/205.1; 424/189.1; 514/44; 435/320.1; 435/325; 435/370; 435/455

(58) Field of Classification Search ............ 435/320.1, 435/235.1, 325, 366, 370, 455; 536/23.1, 536/23.72; 424/184.1, 189.1, 199.1, 202.1, 424/204.1

See application file for complete search history.

(56) References Cited

U.S. PATENT DOCUMENTS 5,679,342 A * 10/1997 Houghton et al. ....... 424/93.21
6,127,116 A 10/2000 Rice et al.

FOREIGN PATENT DOCUMENTS

EP 0 516 270 A2 12/1992
WO WO 97/08310 3/1997
WO WO 98/39031 9/1998

OTHER PUBLICATIONS

Byoung J. Yoo et al, Transfection of a Differentiated Human Hepatoma Cell Line (Huh7) with In Vitro-Transcribed Hepatitis C Virus (HCV) RNA and Establishment of a Long-Term Culture Persistently Infected with HCV, Jan. 1995, p. 32-38, vol. 69, No. 1.*

Nelson Fausto, Editor-in-Chief, Replication of Hepatitis C Virus in Tissue Culture: A Potential Breakthrough in Need of Cofirmation, vol. 151, No. 2, Aug. 1997.*

Forns et al, The chllenge of developing a vaccine against hepatitis C virus, J Hepatology, 2002, vol. 37, pp. 684-695.*

Rice, Hepatitis C: Progress toward New Therapies from Third Annual PHRI Symposium, published 2006 and downloaded Jan. 23, 2006.*

Yanagi et al, "Transcripts of a Chimeric cDNA Clone of Hepatitis C Virus Genotype 1b Are Infectious *in Vivo*", Virology, vol. 244, No. 1, Apr. 25, 1998, pp. 161-172.

Dash et al, "Transfection of HepG2 Cells with Infectious Hepatitis C Virus Genome", *American* Journal of Pathology, vol. 151, No. 2, Aug. 1997, pp/ 363-373.

Fausto, "Replication of Hepatitis C Virus in Tissue Culture: A Potential Breakthrough in Need of Confirmation", American Journal of Pathology, vol. 151, No. 2, Aug. 1997, p. 361.

Kolykhalov et al, "Transmission of Hepatitis C by Intrahepatic Inoculation with Transcribed RNA", Science, vol. 277, No. 5325, Jul. 1997, pp. 570-574.

Yanagi et al, "Transcripts from a single full-length cDNA clone of hepatitis C virus are infectious when directly transfedted into the liver of a chimpanzee", *Proc. Natl. Acad. Sci.* USA, vol. 94, Aug. 1997, pp. 8738-8743.

Yoo et al, "Transfection of a Differentiated Human Hepatoma Cell Line (Huh7) with In Vitro-Transcribed Hepatitis C Virus (HCV) RNA and Establishment of a Long-Term Culture Persistently Infected with HCV", *Journal of Virology*, vol. 69 , No. 1, Jan. 1995, pp. 32-38.

Farci et al, "Prevention of Hepatitis C virus infection in chimpanzees by hyperimmune serum against thehypervariable region 1 of the envelope 2 protein", *Proc. Natl. Sci. USA*, vol. 93, Dec. 1996, pp. 15394-15399.

Inchauspe et al, "Genomic structure of the human prototype strain H of hepatitis C virus: Comparison with American and Japanese isolates", *Proc. Natl. Sci USA*, vol. 88, No. 22, Nov. 1991, pp. 10292-10296.

Kolykhalov et al, "Identification of a Highly Conserved Sequence Element at the 3' Terminus of Hepatitis C Virus Genome RNA", *Journal of Virology*, vol. 70, No. 6 Jun. 1996, pp. 3363-3371.

Ogata et al, "Nucleotide sequence and mutation rate of the H strain of hepatitis C virus", *Proc.* Natl. Acad. Sci. USA, vol. 88, Apr. 1991, pp. 3392-3396.

Okamoto et al, "Genetic Drift of Heptatis C Virus during an 8.2-Year Infection in a Chimpanzee: Variability and Stability", Virology, vol. 190, 1992, pp. 894-899.

(Continued)

*Primary Examiner*—Scott D. Priebe
*Assistant Examiner*—Maria Marvich
(74) *Attorney, Agent, or Firm*—Knobbe Martens Olson & Bear, LLP

(57) ABSTRACT

The present invention discloses nucleic acid sequences which encode infectious hepatitis C viruses and the use of these sequences, and polypeptides encoded by all or part of these sequences, in the development of vaccines and diagnostics for HCV and in the development of screening assays for the identification of antiviral agents for HCV.

8 Claims, 49 Drawing Sheets

OTHER PUBLICATIONS

Honda et al, "Structure Requirements for Initiation of Translation by Internal Ribosome Entry within Genome-Length Hepatitis C Virus RNA", Virology, vol. 222, 1996, pp. 31-42.

Kolykhalov et al, "Hepatitis C Virus-Encoded Enymatic Activites and Conserved RNA Elements in the 3' Nontranslated Region Are Essential for Virus Replication In Vivo", *Journal* of Virology, vol. 74, No. 4, Feb. 2000, pp. 2046-2051.

Lindenbach, B.D. et al. (2006) "Cell culture-grown hepatitis C virus is infectious in vivo and can be recultured in vitro" PNAS 103(10): 3805-3809.

Yu M-YW, Bartosch B, Zhang P, Guo Z-P, Renzi PM, Shen L-M, Granier C, Feinstone SM, Cosset F-L, Purcell RH. Neutralizing antibodies to hepatitis C virus (HCV) in immune globulins derived from anti-HCV-positive plasma. *PNAS USA* 2004;101(20):7705-7710.

Meunier JC, Engle RE, Faulk K, Zhao M, Bartosch B, Alter H, Emerson SU, Cosset FL, Purcell RH, Bukh J. Evidence for cross-genotype neutralization of hepatitis C virus pseudo-particles and enhancement of infectivity by apolipoprotein C1. *PNAS USA* 2005;102(12):4560-4565.

Bassett, SE, Guerra B, Brasky K, Miskovsky E. Houghton M. Klimpel GR, Lanford RE. Protective immune response to hepatitis C virus in chimpanzees rechallenged following clearance of primary infection. *Hepatology* 2001:33:1479-1487.

Major ME. Mihalik K, Puig M. Rehermann B, Nascimbeni M, Rice CM, Feinstone SM. Previously infected and recovered chimpanzees exhibit rapid responses that control hepatitis C virus replication upon rechallenge. *Journal of Virology* 2002:76(13):6586-6595.

Lanford RE. Guerra B, Chavez D. Bigger C, Brasky KM, Wang XH, Ray SC, Thomas DL. Cross-genotype immunity to hepatitis C virus. *Journal of Virology* 2004;78(3):1575-1581.

Weiner AJ, Paliard X, Selby MJ, Medina-Selby A. Coit D, Nguyen S, Kansopon J, Arian CL, Ng P, Tucker J, Lee CT, Polakos NK. Han J, Wong S, Lu HH, Rosenberg S, Brasky KM, Chien D, Kuo G, Houghton M. Intrahepatic gentic inoculation of hepatitis C virus RNA confers cross-protective immunity. *Journal of Virology* 2001;75(15):7142-7148.

Bukh J, Thimme R, Satterfield WC, Meunier JC, Spangenberg HC, Forns X, Chang KM, Emerson SU, Chisari FV, Purcell RH. Persistence of HCV after homologous monoclonal re-challenge is associated with emergence of virus variants. In Jilbert AR, Grgacic EVL, Vickery K, Burrell CJ, Cossart YE, eds. *Proceedings of the 11<sup>th</sup>International Symposium on Viral Hepatitis & Liver Disease.* Australian Centre for Hepatitis Virology 2004:375-377.

Yanagi M, Purcell RH, Emerson SU, Bukh J. Hepatitis C virus: An infectious molecular clone of a second major genotype (2a) and lack of viability of intertypic 1a and 2a chimeras. *Virology* 1999;262(1):250-263.

Okamoto H, Mishiro S, Tokita H, Tsuda F, Miyakawa Y, Mayumi M. Superinfection of chimpanzees carrying hepatitis C virus of genotype II/1b with that of genotype III/2a or I/1a. *Hepatology* 1994;20:1131-1136.

Thimme R, Bukh J, Spangenberg HC, Wieland S, Pemberton J, Steiger C, Govindarajan S, Purcell RH, Chisari FV. Viral and immunological determinants of hepatitis C virus clearance, persistance, and disease. *PNAS USA* 2002;99(24)15661-15668.

Major ME, Dahari H, Mihalik K. Puig M, Rice CM, Neumann AU, Feinstone S. Hepatitis C Virus kinetics and host responses associated with disease and outcome of infection in chimpanzees. *Hepatology* 2004;39(6):1709-1720.

Bigger CB. Braky KM, Lanford RE. DNA microarray analysis of chimpanzee liver during acute resolving hepatitis C virus infection. *Journal of Virology* 2001;75(15):7059-7066.

Su A, Pezacki JP, Wodicka L, Brideau AD, Supekova L, Thimme R, Wieland S, Bukh J, Purcell RH, Schultz PG, Chisari FV. Genomic analysis of the host response to hepatitis C virus infection. *PNAS USA* 2002;99(24):15669-15674.

* cited by examiner

H77C

```
        10         20         30         40         50
1234567890 1234567890 1234567890 1234567890 1234567890
GCCAGCCCCC TGATGGGGGC GACACTCCAC CATGAATCAC TCCCCTGTGA     50
GGAACTACTG TCTTCACGCA GAAAGCGTCT AGCCATGGCG TTAGTATGAG    100
TGTCGTGCAG CCTCCAGGAC CCCCCCTCCC GGGAGAGCCA TAGTGGTCTG    150
CGGAACCGGT GAGTACACCG GAATTGCCAG GACGACCGGG TCCTTTCTTG    200
GATAAACCCG CTCAATGCCT GGAGATTTGG GCGTGCCCCC GCAAGACTGC    250
TAGCCGAGTA GTGTTGGGTC GCGAAAGGCC TTGTGGTACT GCCTGATAGG    300
GTGCTTGCGA GTGCCCCGGG AGGTCTCGTA GACCGTGCAC CATGAGCACG    350
AATCCTAAAC CTCAAAGAAA AACCAAACGT AACACCAACC GTCGCCCACA    400
GGACGTCAAG TTCCCGGGTG GCGGTCAGAT CGTTGGTGGA GTTTACTTGT    450
TGCCGCGCAG GGGCCCTAGA TTGGGTGTGC GCGCGACGAG GAAGACTTCC    500
GAGCGGTCGC AACCTCGAGG TAGACGTCAG CCTATCCCCA AGGCACGTCG    550
GCCCGAGGGC AGGACCTGGG CTCAGCCCGG GTACCCTTGG CCCCTCTATG    600
GCAATGAGGG TTGCGGGTGG GCGGGATGGC TCCTGTCTCC CCGTGGCTCT    650
CGGCCTAGCT GGGGCCCCAC AGACCCCCGG CGTAGGTCGC GCAATTTGGG    700
TAAGGTCATC GATACCCTTA CGTGCGGCTT CGCCGACCTC ATGGGGTACA    750
TACCGCTCGT CGGCGCCCCT CTTGGAGGCG CTGCCAGGGC CCTGGCGCAT    800
GGCGTCCGGG TTCTGGAAGA CGGCGTGAAC TATGCAACAG GGAACCTTCC    850
TGGTTGCTCT TTCTCTATCT TCCTTCTGGC CCTGCTCTCT TGCCTGACTG    900
TGCCCGCTTC AGCCTACCAA GTGCGCAATT CCTCGGGGCT TTACCATGTC    950
ACCAATGATT GCCCTAACTC GAGTATTGTG TACGAGGCGG CCGATGCCAT   1000
CCTGCACACT CCGGGGTGTG TCCCTTGCGT TCGCGAGGGT AACGCCTCGA   1050
GGTGTTGGGT GGCGGTGACC CCCACGGTGG CCACCAGGGA CGGCAAACTC   1100
CCCACAACGC AGCTTCGACG TCATATCGAT CTGCTTGTCG GGAGCGCCAC   1150
CCTCTGCTCG GCCCTCTACG TGGGGGACCT GTGCGGGTCT GTCTTTCTTG   1200
TTGGTCAACT GTTTACCTTC TCTCCCAGGC GCCACTGGAC GACGCAAGAC   1250
TGCAATTGTT CTATCTATCC CGGCCATATA ACGGGTCATC GCATGGCATG   1300
GGATATGATG ATGAACTGGT CCCCTACGGC AGCGTTGGTG GTAGCTCAGC   1350
TGCTCCGGAT CCCACAAGCC ATCATGGACA TGATCGCTGG TGCTCACTGG   1400
GGAGTCCTGG CGGGCATAGC GTATTTCTCC ATGGTGGGGA ACTGGGCGAA   1450
GGTCCTGGTA GTGCTGCTGC TATTTGCCGG CGTCGACGCG GAAACCCACG   1500
TCACCGGGGG AAATGCCGGC CGCACCACGG CTGGGCTTGT TGGTCTCCTT   1550
ACACCAGGCG CCAAGCAGAA CATCCAACTG ATCAACACCA ACGGCAGTTG   1600
GCACATCAAT AGCACGGCCT TGAATTGCAA TGAAAGCCTT AACACCGGCT   1650
GGTTAGCAGG GCTCTTCTAT CAACACAAAT TCAACTCTTC AGGCTGTCCT   1700
GAGAGGTTGG CCAGCTGCCG ACGCCTTACC GATTTTGCCC AGGGCTGGGG   1750
TCCTATCAGT TATGCCAACG GAAGCGGCCT CGACGAACGC CCCTACTGCT   1800
GGCACTACCC TCCAAGACCT TGTGGCATTG TGCCCGCAAA GAGCGTGTGT   1850
GGCCCGGTAT ATTGCTTCAC TCCCAGCCCC GTGGTGGTGG GAACGACCGA   1900
```

| | | | | | |
|---|---|---|---|---|---|
| 10 | 20 | 30 | 40 | 50 | |
| 1234567890 | 1234567890 | 1234567890 | 1234567890 | 1234567890 | |
| CAGGTCGGGC | GCGCCTACCT | ACAGCTGGGG | TGCAAATGAT | ACGGATGTCT | 1950 |
| TCGTCCTTAA | CAACACCAGG | CCACCGCTGG | GCAATTGGTT | CGGTTGTACC | 2000 |
| TGGATGAACT | CAACTGGATT | CACCAAAGTG | TGCGGAGCGC | CCCCTTGTGT | 2050 |
| CATCGGAGGG | GTGGGCAACA | ACACCTTGCT | CTGCCCCACT | GATTGCTTCC | 2100 |
| GCAAACATCC | GGAAGCCACA | TACTCTCGGT | GCGGCTCCGG | TCCCTGGATT | 2150 |
| ACACCCAGGT | GCATGGTCGA | CTACCCGTAT | AGGCTTTGGC | ACTATCCTTG | 2200 |
| TACCATCAAT | TACACCATAT | TCAAAGTCAG | GATGTACGTG | GGAGGGGTCG | 2250 |
| AGCACAGGCT | GGAAGCGGCC | TGCAACTGGA | CGCGGGGCGA | ACGCTGTGAT | 2300 |
| CTGGAAGACA | GGGACAGGTC | CGAGCTCAGC | CCGTTGCTGC | TGTCCACCAC | 2350 |
| ACAGTGGCAG | GTCCTTCCGT | GTTCTTTCAC | GACCCTGCCA | GCCTTGTCCA | 2400 |
| CCGGCCTCAT | CCACCTCCAC | CAGAACATTG | TGGACGTGCA | GTACTTGTAC | 2450 |
| GGGGTAGGGT | CAAGCATCGC | GTCCTGGGCC | ATTAAGTGGG | AGTACGTCGT | 2500 |
| TCTCCTGTTC | CTTCTGCTTG | CAGACGCGCG | CGTCTGCTCC | TGCTTGTGGA | 2550 |
| TGATGTTACT | CATATCCCAA | GCGGAGGCGG | CTTTGGAGAA | CCTCGTAATA | 2600 |
| CTCAATGCAG | CATCCCTGGC | CGGGACGCAC | GGTCTTGTGT | CCTTCCTCGT | 2650 |
| GTTCTTCTGC | TTTGCGTGGT | ATCTGAAGGG | TAGGTGGGTG | CCCGGAGCGG | 2700 |
| TCTACGCCCT | CTACGGGATG | TGGCCTCTCC | TCCTGCTCCT | GCTGGCGTTG | 2750 |
| CCTCAGCGGG | CATACGCACT | GGACACGGAG | GTGGCCGCGT | CGTGTGGCGG | 2800 |
| CGTTGTTCTT | GTCGGGTTAA | TGGCGCTGAC | TCTGTCGCCA | TATTACAAGC | 2850 |
| GCTATATCAG | CTGGTGCATG | TGGTGGCTTC | AGTATTTTCT | GACCAGAGTA | 2900 |
| GAAGCGCAAC | TGCACGTGTG | GGTTCCCCCC | CTCAACGTCC | GGGGGGGGCG | 2950 |
| CGATGCCGTC | ATCTTACTCA | TGTGTGTAGT | ACACCCGACC | CTGGTATTTG | 3000 |
| ACATCACCAA | ACTACTCCTG | GCCATCTTCG | GACCCCTTTG | GATTCTTCAA | 3050 |
| GCCAGTTTGC | TTAAAGTCCC | CTACTTCGTG | CGCGTTCAAG | GCCTTCTCCG | 3100 |
| GATCTGCGCG | CTAGCGCGGA | AGATAGCCGG | AGGTCATTAC | GTGCAAATGG | 3150 |
| CCATCATCAA | GTTAGGGGCG | CTTACTGGCA | CCTATGTGTA | TAACCATCTC | 3200 |
| ACCCCTCTTC | GAGACTGGGC | GCACAACGGC | CTGCGAGATC | TGGCCGTGGC | 3250 |
| TGTGGAACCA | GTCGTCTTCT | CCCGAATGGA | GACCAAGCTC | ATCACGTGGG | 3300 |
| GGGCAGATAC | CGCCGCGTGC | GGTGACATCA | TCAACGGCTT | GCCCGTCTCT | 3350 |
| GCCCGTAGGG | GCCAGGAGAT | ACTGCTTGGG | CCAGCCGACG | GAATGGTCTC | 3400 |
| CAAGGGGTGG | AGGTTGCTGG | CGCCCATCAC | GGCGTACGCC | CAGCAGACGA | 3450 |
| GAGGCCTCCT | AGGGTGTATA | ATCACCAGCC | TGACTGGCCG | GGACAAAAAC | 3500 |
| CAAGTGGAGG | GTGAGGTCCA | GATCGTGTCA | ACTGCTACCC | AAACCTTCCT | 3550 |
| GGCAACGTGC | ATCAATGGGG | TATGCTGGAC | TGTCTACCAC | GGGGCCGGAA | 3600 |
| CGAGGACCAT | CGCATCACCC | AAGGGTCCTG | TCATCCAGAT | GTATACCAAT | 3650 |
| GTGGACCAAG | ACCTTGTGGG | CTGGCCCGCT | CCTCAAGGTT | CCCGCTCATT | 3700 |
| GACACCCTGT | ACCTGCGGCT | CCTCGGACCT | TTACCTGGTC | ACGAGGCACG | 3750 |
| CCGATGTCAT | TCCCGTGCGC | CGGCGAGGTG | ATAGCAGGGG | TAGCCTGCTT | 3800 |

| 10<br>1234567890 | 20<br>1234567890 | 30<br>1234567890 | 40<br>1234567890 | 50<br>1234567890 | |
|---|---|---|---|---|---|
| TCGCCCCGGC | CCATTTCCTA | CTTGAAAGGC | TCCTCGGGGG | GTCCGCTGTT | 3850 |
| GTGCCCCGCG | GGACACGCCG | TGGGCCTATT | CAGGGCCGCG | GTGTGCACCC | 3900 |
| GTGGAGTGGC | TAAAGCGGTG | GACTTTATCC | CTGTGGAGAA | CCTAGGGACA | 3950 |
| ACCATGAGAT | CCCCGGTGTT | CACGGACAAC | TCCTCTCCAC | CAGCAGTGCC | 4000 |
| CCAGAGCTTC | CAGGTGGCCC | ACCTGCATGC | TCCCACCGGC | AGCGGTAAGA | 4050 |
| GCACCAAGGT | CCCGGCTGCG | TACGCAGCCC | AGGGCTACAA | GGTGTTGGTG | 4100 |
| CTCAACCCCT | CTGTTGCTGC | AACGCTGGGC | TTTGGTGCTT | ACATGTCCAA | 4150 |
| GGCCCATGGG | GTTGATCCTA | ATATCAGGAC | CGGGGTGAGA | ACAATTACCA | 4200 |
| CTGGCAGCCC | CATCACGTAC | TCCACCTACG | GCAAGTTCCT | TGCCGACGGC | 4250 |
| GGGTGCTCAG | GAGGTGCTTA | TGACATAATA | ATTTGTGACG | AGTGCCACTC | 4300 |
| CACGGATGCC | ACATCCATCT | TGGGCATCGG | CACTGTCCTT | GACCAAGCAG | 4350 |
| AGACTGCGGG | GGCGAGACTG | GTTGTGCTCG | CCACTGCTAC | CCCTCCGGGC | 4400 |
| TCCGTCACTG | TGTCCCATCC | TAACATCGAG | GAGGTTGCTC | TGTCCACCAC | 4450 |
| CGGAGAGATC | CCCTTTTACG | GCAAGGCTAT | CCCCCTCGAG | GTGATCAAGG | 4500 |
| GGGGAAGACA | TCTCATCTTC | TGCCACTCAA | AGAAGAAGTG | CGACGAGCTC | 4550 |
| GCCGCGAAGC | TGGTCGCATT | GGGCATCAAT | GCCGTGGCCT | ACTACCGCGG | 4600 |
| TCTTGACGTG | TCTGTCATCC | CGACCAGCGG | CGATGTTGTC | GTCGTGTCGA | 4650 |
| CCGATGCTCT | CATGACTGGC | TTTACCGGCG | ACTTCGACTC | TGTGATAGAC | 4700 |
| TGCAACACGT | GTGTCACTCA | GACAGTCGAT | TTCAGCCTTG | ACCCTACCTT | 4750 |
| TACCATTGAG | ACAACCACGC | TCCCCCAGGA | TGCTGTCTCC | AGGACTCAAC | 4800 |
| GCCGGGGCAG | GACTGGCAGG | GGGAAGCCAG | GCATCTATAG | ATTTGTGGCA | 4850 |
| CCGGGGGAGC | GCCCCTCCGG | CATGTTCGAC | TCGTCCGTCC | TCTGTGAGTG | 4900 |
| CTATGACGCG | GGCTGTGCTT | GGTATGAGCT | CACGCCCGCC | GAGACTACAG | 4950 |
| TTAGGCTACG | AGCGTACATG | AACACCCCGG | GGCTTCCCGT | GTGCCAGGAC | 5000 |
| CATCTTGAAT | TTTGGGAGGG | CGTCTTTACG | GGCCTCACTC | ATATAGATGC | 5050 |
| CCACTTTTTA | TCCCAGACAA | AGCAGAGTGG | GGAGAACTTT | CCTTACCTGG | 5100 |
| TAGCGTACCA | AGCCACCGTG | TGCGCTAGGG | CTCAAGCCCC | TCCCCCATCG | 5150 |
| TGGGACCAGA | TGTGGAAGTG | TTTGATCCGC | CTTAAACCCA | CCCTCCATGG | 5200 |
| GCCAACACCC | CTGCTATACA | GACTGGCCGC | TGTTCAGAAT | GAAGTCACCC | 5250 |
| TGACGCACCC | AATCACCAAA | TACATCATGA | CATGCATGTC | GGCCGACCTG | 5300 |
| GAGGTCGTCA | CGAGCACCTG | GGTGCTCGTT | GGCGGCGTCC | TGGCTGCTCT | 5350 |
| GGCCGCGTAT | TGCCTGTCAA | CAGGCTGCGT | GGTCATAGTG | GGCAGGATCG | 5400 |
| TCTTGTCCGG | GAAGCCGGCA | ATTATACCTG | ACAGGGAGGT | TCTCTACCAG | 5450 |
| GAGTTCGATG | AGATGGAAGA | GTGCTCTCAG | CACTTACCGT | ACATCGAGCA | 5500 |
| AGGGATGATG | CTCGCTGAGC | AGTTCAAGCA | GAAGGCCCTC | GGCCTCCTGC | 5550 |
| AGACCGCGTC | CCGCCATGCA | GAGGTTATCA | CCCCTGCTGT | CCAGACCAAC | 5600 |
| TGGCAGAAAC | TCGAGGTCTT | TTGGGCGAAG | CACATGTGGA | ATTTCATCAG | 5650 |
| TGGGATACAA | TACTTGGCGG | GCCTGTCAAC | GCTGCCTGGT | AACCCCGCCA | 5700 |

| 10<br>1234567890 | 20<br>1234567890 | 30<br>1234567890 | 40<br>1234567890 | 50<br>1234567890 | |
|---|---|---|---|---|---|
| TTGCTTCATT | GATGGCTTTT | ACAGCTGCCG | TCACCAGCCC | ACTAACCACT | 5750 |
| GGCCAAACCC | TCCTCTTCAA | CATATTGGGG | GGGTGGGTGG | CTGCCCAGCT | 5800 |
| CGCCGCCCCC | GGTGCCGCTA | CTGCCTTTGT | GGGTGCTGGC | CTAGCTGGCG | 5850 |
| CCGCCATCGG | CAGCGTTGGA | CTGGGGAAGG | TCCTCGTGGA | CATTCTTGCA | 5900 |
| GGGTATGGCG | CGGGCGTGGC | GGGAGCTCTT | GTAGCATTCA | AGATCATGAG | 5950 |
| CGGTGAGGTC | CCCTCCACGG | AGGACCTGGT | CAATCTGCTG | CCCGCCATCC | 6000 |
| TCTCGCCTGG | AGCCCTTGTA | GTCGGTGTGG | TCTGCGCAGC | AATACTGCGC | 6050 |
| CGGCACGTTG | GCCCGGGCGA | GGGGGCAGTG | CAATGGATGA | ACCGGCTAAT | 6100 |
| AGCCTTCGCC | TCCCGGGGGA | ACCATGTTTC | CCCCACGCAC | TACGTGCCGG | 6150 |
| AGAGCGATGC | AGCCGCCCGC | GTCACTGCCA | TACTCAGCAG | CCTCACTGTA | 6200 |
| ACCCAGCTCC | TGAGGCGACT | GCATCAGTGG | ATAAGCTCGG | AGTGTACCAC | 6250 |
| TCCATGCTCC | GGTTCCTGGC | TAAGGGACAT | CTGGGACTGG | ATATGCGAGG | 6300 |
| TGCTGAGCGA | CTTTAAGACC | TGGCTGAAAG | CCAAGCTCAT | GCCACAACTG | 6350 |
| CCTGGGATTC | CCTTTGTGTC | CTGCCAGCGC | GGGTATAGGG | GGGTCTGGCG | 6400 |
| AGGAGACGGC | ATTATGCACA | CTCGCTGCCA | CTGTGGAGCT | GAGATCACTG | 6900 |
| GACATGTCAA | AAACGGGACG | ATGAGGATCG | TCGGTCCTAG | GACCTGCAGG | 6950 |
| AACATGTGGA | GTGGGACGTT | CCCCATTAAC | GCCTACACCA | CGGGCCCCTG | 6550 |
| TACTCCCCTT | CCTGCGCCGA | ACTATAAGTT | CGCGCTGTGG | AGGGTGTCTG | 6600 |
| CAGAGGAATA | CGTGGAGATA | AGGCGGGTGG | GGGACTTCCA | CTACGTATCG | 6650 |
| GGTATGACTA | CTGACAATCT | TAAATGCCCG | TGCCAGATCC | CATCGCCCGA | 6700 |
| ATTTTTCACA | GAATTGGACG | GGGTGCGCCT | ACACAGGTTT | GCGCCCCCTT | 6750 |
| GCAAGCCCTT | GCTGCGGGAG | GAGGTATCAT | TCAGAGTAGG | ACTCCACGAG | 6800 |
| TACCCGGTGG | GGTCGCAATT | ACCTTGCGAG | CCCGAACCGG | ACGTAGCCGT | 6850 |
| GTTGACGTCC | ATGCTCACTG | ATCCCTCCCA | TATAACAGCA | GAGGCGGCCG | 6900 |
| GGAGAAGGTT | GGCGAGAGGG | TCACCCCCTT | CTATGGCCAG | CTCCTCGGCT | 6950 |
| AGCCAGCTGT | CCGCTCCATC | TCTCAAGGCA | ACTTGCACCG | CCAACCATGA | 7000 |
| CTCCCCTGAC | GCCGAGCTCA | TAGAGGCTAA | CCTCCTGTGG | AGGCAGGAGA | 7050 |
| TGGGCGGCAA | CATCACCAGG | GTTGAGTCAG | AGAACAAAGT | GGTGATTCTG | 7100 |
| GACTCCTTCG | ATCCGCTTGT | GGCAGAGGAG | GATGAGCGGG | AGGTCTCCGT | 7150 |
| ACCTGCAGAA | ATTCTGCGGA | AGTCTCGGAG | ATTCGCCCGG | GCCCTGCCCG | 7200 |
| TCTGGGCGCG | GCCGGACTAC | AACCCCCCGC | TAGTAGAGAC | GTGGAAAAAG | 7250 |
| CCTGACTACG | AACCACCTGT | GGTCCATGGC | TGCCCGCTAC | CACCTCCACG | 7300 |
| GTCCCCTCCT | GTGCCTCCGC | CTCGGAAAAA | GCGTACGGTG | GTCCTCACCG | 7350 |
| AATCAACCCT | ATCTACTGCC | TTGGCCGAGC | TTGCCACCAA | AAGTTTTGGC | 7400 |
| AGCTCCTCAA | CTTCCGGCAT | TACGGGCGAC | AATACGACAA | CATCCTCTGA | 7450 |
| GCCCGCCCCT | TCTGGCTGCC | CCCCCGACTC | CGACGTTGAG | TCCTATTCTT | 7500 |
| CCATGCCCCC | CCTGGAGGGG | GAGCCTGGGG | ATCCGGATCT | CAGCGACGGG | 7550 |
| TCATGGTCGA | CGGTCAGTAG | TGGGGCCGAC | ACGGAAGATG | TCGTGTGCTG | 7600 |

| 10<br>1234567890 | 20<br>1234567890 | 30<br>1234567890 | 40<br>1234567890 | 50<br>1234567890 | |
|---|---|---|---|---|---|
| CTCAATGTCT | TATTCCTGGA | CAGGCGCACT | CGTCACCCCG | TGCGCTGCGG | 7650 |
| AAGAACAAAA | ACTGCCCATC | AACGCACTGA | GCAACTCGTT | GCTACGCCAT | 7700 |
| CACAATCTGG | TGTATTCCAC | CACTTCACGC | AGTGCTTGCC | AAAGGCAGAA | 7750 |
| GAAAGTCACA | TTTGACAGAC | TGCAAGTTCT | GGACAGCCAT | TACCAGGACG | 7800 |
| TGCTCAAGGA | GGTCAAAGCA | GCGGCGTCAA | AAGTGAAGGC | TAACTTGCTA | 7850 |
| TCCGTAGAGG | AAGCTTGCAG | CCTGACGCCC | CCACATTCAG | CCAAATCCAA | 7900 |
| GTTTGGCTAT | GGGGCAAAAG | ACGTCCGTTG | CCATCCCAGA | AAGGCCGTAG | 7950 |
| CCCACATCAA | CTCCGTGTGG | AAAGACCTTC | TGGAAGACAG | TGTAACACCA | 8000 |
| ATAGACACTA | CCATCATGGC | CAAGAACGAG | GTTTTCTGCG | TTCAGCCTGA | 8050 |
| GAAGGGGGGT | CGTAAGCCAG | CTCGTCTCAT | CGTGTTCCCC | GACCTGGGCG | 8100 |
| TGCGCGTGTG | CGAGAAGATG | GCCCTGTACG | ACGTGGTTAG | CAAGCTCCCC | 8150 |
| CTGGCCGTGA | TGGGAAGCTC | CTACGGATTC | CAATACTCAC | CAGGACAGCG | 8200 |
| GGTTGAATTC | CTCGTGCAAG | CGTGGAAGTC | CAAGAAGACC | CCGATGGGGT | 8250 |
| TCTCGTATGA | TACCCGCTGT | TTTGACTCCA | CAGTCACTGA | GAGCGACATC | 8300 |
| CGTACGGAGG | AGGCAATTTA | CCAATGTTGT | GACCTGGACC | CCCAAGCCCG | 8350 |
| CGTGGCCATC | AAGTCCCTCA | CTGAGAGGCT | TTATGTTGGG | GGCCCTCTTA | 8400 |
| CCAATTCAAG | GGGGGAAAAC | TGCGGCTACC | GCAGGTGCCG | CGCGAGCGGC | 8450 |
| GTACTGACAA | CTAGCTGTGG | TAACACCCTC | ACTTGCTACA | TCAAGGCCCG | 8500 |
| GGCAGCCTGT | CGAGCCGCAG | GGCTCCAGGA | CTGCACCATG | CTCGTGTGTG | 8550 |
| GCGACGACTT | AGTCGTTATC | TGTGAAAGTG | CGGGGGTCCA | GGAGGACGCG | 8600 |
| GCGAGCCTGA | GAGCCTTCAC | GGAGGCTATG | ACCAGGTACT | CCGCCCCCCC | 8650 |
| CGGGGACCCC | CCACAACCAG | AATACGACTT | GGAGCTTATA | ACATCATGCT | 8700 |
| CCTCCAACGT | GTCAGTCGCC | CACGACGGCG | CTGGAAAGAG | GGTCTACTAC | 8750 |
| CTTACCCGTG | ACCCTACAAC | CCCCCTCGCG | AGAGCCGCGT | GGGAGACAGC | 8800 |
| AAGACACACT | CCAGTCAATT | CCTGGCTAGG | CAACATAATC | ATGTTTGCCC | 8850 |
| CCACACTGTG | GGCGAGGATG | ATACTGATGA | CCCATTTCTT | TAGCGTCCTC | 8900 |
| ATAGCCAGGG | ATCAGCTTGA | ACAGGCTCTT | AACTGTGAGA | TCTACGGAGC | 8950 |
| CTGCTACTCC | ATAGAACCAC | TGGATCTACC | TCCAATCATT | CAAAGACTCC | 9000 |
| ATGGCCTCAG | CGCATTTTCA | CTCCACAGTT | ACTCTCCAGG | TGAAATCAAT | 9050 |
| AGGGTGGCCG | CATGCCTCAG | AAAACTTGGG | GTCCCGCCCT | TGCGAGCTTG | 9100 |
| GAGACACCGG | GCCCGGAGCG | TCCGCGCTAG | GCTTCTGTCC | AGAGGAGGCA | 9150 |
| GGGCTGCCAT | ATGTGGCAAG | TACCTCTTCA | ACTGGGCAGT | AAGAACAAAG | 9200 |
| CTCAAACTCA | CTCCAATAGC | GGCCGCTGGC | CGGCTGGACT | TGTCCGGTTG | 9250 |
| GTTCACGGCT | GGCTACAGCG | GGGGAGACAT | TTATCACAGC | GTGTCTCATG | 9300 |
| CCCGGCCCCG | CTGGTTCTGG | TTTTGCCTAC | TCCTGCTCGC | TGCAGGGGTA | 9350 |
| GGCATCTACC | TCCTCCCCAA | CCGATGAAGG | TTGGGGTAAA | CACTCCGGCC | 9400 |
| TCTTAAGCCA | TTTCCTGTTT | TTTTTTTTTT | TTTTTTTTTT | TTTTTCTTTT | 9450 |
| TTTTTTTCTT | TCCTTTCCTT | CTTTTTTTCC | TTTCTTTTTC | CCTTCTTTAA | 9500 |

| | | | | | |
|---|---|---|---|---|---|
| 10 | 20 | 30 | 40 | 50 | |
| 1234567890 | 1234567890 | 1234567890 | 1234567890 | 1234567890 | |
| TGGTGGCTCC | ATCTTAGCCC | TAGTCACGGC | TAGCTGTGAA | AGGTCCGTGA | 9550 |
| GCCGCATGAC | TGCAGAGAGT | GCTGATACTG | GCCTCTCTGC | AGATCATGT | 9599 |

```
        10         20         30         40         50
1234567890 1234567890 1234567890 1234567890 1234567890
MSTNPKPQRK TKRNTNRRPQ DVKFPGGGQI VGGVYLLPRR GPRLGVRATR     50
KTSERSQPRG RRQPIPKARR PEGRTWAQPG YPWPLYGNEG CGWAGWLLSP    100
RGSRPSWGPT DPRRRSRNLG KVIDTLTCGF ADLMGYIPLV GAPLGGAARA    150
LAHGVRVLED GVNYATGNLP GCSFSIFLLA LLSCLTVPAS AYQVRNSSGL    200
YHVTNDCPNS SIVYEAADAI LHTPGCVPCV REGNASRCWV AVTPTVATRD    250
GKLPTTQLRR HIDLLVGSAT LCSALYVGDL CGSVFLVGQL FTFSPRRHWT    300
TQDCNCSIYP GHITGHRMAW DMMMNWSPTA ALVVAQLLRI PQAIMDMIAG    350
AHWGVLAGIA YFSMVGNWAK VLVVLLLFAG VDAETHVTGG NAGRTTAGLV    400
GLLTPGAKQN IQLINTNGSW HINSTALNCN ESLNTGWLAG LFYQHKFNSS    450
GCPERLASCR RLTDFAQGWG PISYANGSGL DERPYCWHYP PRPCGIVPAK    500
SVCGPVYCFT PSPVVVGTTD RSGAPTYSWG ANDTDVFVLN NTRPPLGNWF    550
GCTWMNSTGF TKVCGAPPCV IGGVGNNTLL CPTDCFRKHP EATYSRCGSG    600
PWITPRCMVD YPYRLWHYPC TINYTIFKVR MYVGGVEHRL EAACNWTRGE    650
RCDLEDRDRS ELSPLLLSTT QWQVLPCSFT TLPALSTGLI HLHQNIVDVQ    700
YLYGVGSSIA SWAIKWEYVV LLFLLLADAR VCSCLWMMLL ISQAEAALEN    750
LVILNAASLA GTHGLVSFLV FFCFAWYLKG RWVPGAVYAL YGMWPLLLLL    800
LALPQRAYAL DTEVAASCGG VVLVGLMALT LSPYYKRYIS WCMWWLQYFL    850
TRVEAQLHVW VPPLNVRGGR DAVILLMCVV HPTLVFDITK LLLAIFGPLW    900
ILQASLLKVP YFVRVQGLLR ICALARKIAG GHYVQMAIIK LGALTGTYVY    950
NHLTPLRDWA HNGLRDLAVA VEPVVFSRME TKLITWGADT AACGDIINGL   1000
PVSARRGQEI LLGPADGMVS KGWRLLAPIT AYAQQTRGLL GCIITSLTGR   1050
DKNQVEGEVQ IVSTATQTFL ATCINGVCWT VYHGAGTRTI ASPKGPVIQM   1100
YTNVDQDLVG WPAPQGSRSL TPCTCGSSDL YLVTRHADVI PVRRRGDSRG   1150
SLLSPRPISY LKGSSGGPLL CPAGHAVGLF RAAVCTRGVA KAVDFIPVEN   1200
LGTTMRSPVF TDNSSPPAVP QSFQVAHLHA PTGSGKSTKV PAAYAAQGYK   1250
VLVLNPSVAA TLGFGAYMSK AHGVDPNIRT GVRTITTGSP ITYSTYGKFL   1300
ADGGCSGGAY DIIICDECHS TDATSILGIG TVLDQAETAG ARLVVLATAT   1350
PPGSVTVSHP NIEEVALSTT GEIPFYGKAI PLEVIKGGRH LIFCHSKKKC   1400
DELAAKLVAL GINAVAYYRG LDVSVIPTSG DVVVVSTDAL MTGFTGDFDS   1450
VIDCNTCVTQ TVDFSLDPTF TIETTTLPQD AVSRTQRRGR TGRGKPGIYR   1500
FVAPGERPSG MFDSSVLCEC YDAGCAWYEL TPAETTVRLR AYMNTPGLPV   1550
CQDHLEFWEG VFTGLTHIDA HFLSQTKQSG ENFPYLVAYQ ATVCARAQAP   1600
PPSWDQMWKC LIRLKPTLHG PTPLLYRLGA VQNEVTLTHP ITKYIMTCMS   1650
ADLEVVTSTW VLVGGVLAAL AAYCLSTGCV VIVGRIVLSG KPAIIPDREV   1700
LYQEFDEMEE CSQHLPYIEQ GMMLAEQFKQ KALGLLQTAS RHAEVITPAV   1750
QTNWQKLEVF WAKHMWNFIS GIQYLAGLST LPGNPAIASL MAFTAAVTSP   1800
LTTGQTLLFN ILGGWVAAQL AAPGAATAFV GAGLAGAAIG SVGLGKVLVD   1850
ILAGYGAGVA GALVAFKIMS GEVPSTEDLV NLLPAILSPG ALVVGVVCAA   1900
```

| 10 | 20 | 30 | 40 | 50 | |
|---|---|---|---|---|---|
| 1234567890 | 1234567890 | 1234567890 | 1234567890 | 1234567890 | |
| ILRRHVGPGE | GAVQWMNRLI | AFASRGNHVS | PTHYVPESDA | AARVTAILSS | 1950 |
| LTVTQLLRRL | HQWISSECTT | PCSGSWLRDI | WDWICEVLSD | FKTWLKAKLM | 2000 |
| PQLPGIPFVS | CQRGYRGVWR | GDGIMHTRCH | CGAEITGHVK | NGTMRIVGPR | 2050 |
| TCRNMWSGTF | PINAYTTGPC | TPLPAPNYKF | ALWRVSAEEY | VEIRRVGDFH | 2100 |
| YVSGMTTDNL | KCPCQIPSPE | FFTELDGVRL | HRFAPPCKPL | LREEVSFRVG | 2150 |
| LHEYPVGSQL | PCEPEPDVAV | LTSMLTDPSH | ITAEAAGRRL | ARGSPPSMAS | 2200 |
| SSASQLSAPS | LKATCTANHD | SPDAELIEAN | LLWRQEMGGN | ITRVESENKV | 2250 |
| VILDSFDPLV | AEEDEREVSV | PAEILRKSRR | FARALPVWAR | PDYNPPLVET | 2300 |
| WKKPDYEPPV | VHGCPLPPPR | SPPVPPPRKK | RTVVLTESTL | STALAELATK | 2350 |
| SFGSSSTSGI | TGDNTTTSSE | PAPSGCPPDS | DVESYSSMPP | LEGEPGDPDL | 2400 |
| SDGSWSTVSS | GADTEDVVCC | SMSYSWTGAL | VTPCAAEEQK | LPINALSNSL | 2450 |
| LRHHNLVYST | TSRSACQRQK | KVTFDRLQVL | DSHYQDVLKE | VKAAASKVKA | 2500 |
| NLLSVEEACS | LTPPHSAKSK | FGYGAKDVRC | HARKAVAHIN | SVWKDLLEDS | 2550 |
| VTPIDTTIMA | KNEVFCVQPE | KGGRKPARLI | VFPDLGVRVC | EKMALYDVVS | 2600 |
| KLPLAVMGSS | YGFQYSPGQR | VEFLVQAWKS | KKTPMGFSYD | TRCFDSTVTE | 2650 |
| SDIRTEEAIY | QCCDLDPQAR | VAIKSLTERL | YVGGPLTNSR | GENCGYRRCR | 2700 |
| ASGVLTTSCG | NTLTCYIKAR | AACRAAGLQD | CTMLVCGDDL | VVICESAGVQ | 2750 |
| EDAASLRAFT | EAMTRYSAPP | GDPPQPEYDL | ELITSCSSNV | SVAHDGAGKR | 2800 |
| VYYLTRDPTT | PLARAAWETA | RHTPVNSWLG | NIIMFAPTLW | ARMILMTHFF | 2850 |
| SVLIARDQLE | QALNCEIYGA | CYSIEPLDLP | PIIQRLHGLS | AFSLHSYSPG | 2900 |
| EINRVAACLR | KLGVPPLRAW | RHRARSVRAR | LLSRGGRAAI | CGKYLFNWAV | 2950 |
| RTKLKLTPIA | AAGRLDLSGW | FTAGYSGGDI | YHSVSHARPR | WFWFCLLLLA | 3000 |
| AGVGIYLLPN | R | | | | 3011 |

FIG. 4H

| | L fragment | Cons-p9 | L1* (A) | L2(A) | L6(A) | L8(A) | L9(A) | L3(B) | L7*(B) | L10(B) | L4(C) | Cons-D | Cons-F |
|---|---|---|---|---|---|---|---|---|---|---|---|---|---|
| Core | 16 | N | S | • | • | • | • | • | • | • | • | • | N |
| | 36 | L | • | • | • | P | • | • | • | • | • | • | L |
| | 52 | A | • | • | • | • | • | T | T | T | T | T | A,T |
| | 70 | R | • | • | • | • | • | Q | Q | Q | • | R,Q | R,Q |
| E1 | 189 | A | • | • | • | • | • | • | T | • | • | • | A |
| | 195 | R | • | • | • | • | • | H | • | H | • | • | R |
| | 231 | R | • | Q | Q | Q | • | • | • | • | • | • | R |
| | 233 | G | • | • | • | • | • | A | A | A | • | • | G |
| | 234 | N | • | • | • | • | • | D | D | D | • | • | N |
| | 250 | N | • | • | • | • | • | • | • | • | • | • | N |
| | 299 | E | A | • | • | • | A | • | • | • | • | • | E |
| | 304 | C | • | • | • | • | • | • | • | • | • | • | C |
| | 379 | A | • | • | • | • | • | T | • | T | • | • | A |

FIG. 7A

| | L fragment | Cons-p9 | L1* (A) | L2(A) | L6(A) | L8(A) | L9(A) | L3(B) | L7*(B) | L10(B) | L4(C) | Cons-D | Cons-F |
|---|---|---|---|---|---|---|---|---|---|---|---|---|---|
| E2 | 384 | E | • | • | • | • | • | T | T | T | • | E,T | A |
| | 386 | H | • | • | • | • | • | V | V | V | • | H,Y | H,Y |
| | 388 | T | • | • | • | • | • | S | S | S | • | T,S | T,S |
| | 390 | R | • | • | • | • | • | G | G | G | • | G | R,G |
| | 391 | V | • | • | • | • | • | • | • | A | • | • | V |
| | 392 | A | V | • | • | V | V | • | • | • | V | V | A,V |
| | 394 | H | • | • | • | • | • | R | R | R | R | • | H |
| | 405 | S | • | • | • | • | • | • | P | • | • | • | S |
| | 434 | Q | • | • | • | • | • | H | H | H | | H | Q,H |
| | 438 | F | • | • | • | • | • | L | L | L | L | L | F,L |
| | 444 | A | • | • | • | • | • | T | T | T | | T | A,T |
| | 450 | S | • | • | • | • | • | • | • | • | P | • | S |
| | 458 | S | • | • | • | N | • | • | • | • | • | • | S |
| | 466 | A | • | • | • | • | • | V | V | V | | A,V | A,V |
| | 474 | Y | • | • | • | • | • | H | • | • | • | • | Y |
| | 476 | K | • | • | • | • | • | E | E | E | E | E | K,E |
| | 496 | V | • | • | • | • | • | I | I | I | I | I | V,I |
| | 524 | V | • | • | • | • | A | • | A | • | • | • | V |
| | 536 | V | • | M | • | • | • | • | • | • | • | • | V |
| | 580 | I | • | • | • | • | • | • | V | • | • | • | I |
| | 622 | L | V | • | • | • | V | • | • | • | • | • | L |
| | 673 | Q | • | • | • | P | | • | • | • | • | • | Q |
| p7 | 783 | A | • | • | • | • | • | • | V | • | • | • | A |

FIG. 7B

| | L fragment | Cons-p9 | L1* (A) | L2(A) | L6(A) | L8(A) | L9(A) | L3(B) | L7*(B) | L10(B) | L4(C) | Cons-D | Cons-F |
|---|---|---|---|---|---|---|---|---|---|---|---|---|---|
| NS2 | 820 | G | • | • | • | • | • | • | S | • | • | • | G |
| | 857 | M | • | • | • | • | • | I | | • | • | • | M |
| | 927 | K | • | • | • | • | • | • | R | • | • | • | K |
| | 934 | V | I | I | • | I | I | • | • | • | • | • | V |
| | 937 | A | • | • | V | • | • | • | • | • | • | • | A |
| | 978 | A | • | • | • | • | • | D | D | D | • | D | A,D |
| NS3 | 1028 | P | • | • | • | S | • | • | • | • | • | • | P |
| | 1031 | A | • | • | • | • | • | • | T | • | • | • | A |
| | 1043 | V | • | • | I | • | I | I | I | • | I | • | V,I |
| | 1067 | Q | • | • | • | • | H | H | H | • | • | H,Q | Q,H |
| | 1097 | I | X | • | • | • | • | • | • | • | • | • | I |
| | 1188 | G | R | • | • | • | • | • | • | • | • | • | G |
| | 1215 | S | • | • | T | • | • | • | • | • | • | • | S |
| | 1223 | F | • | S | • | • | • | • | • | • | • | • | F |
| | 1226 | A | • | • | • | • | • | • | • | V | • | • | A |
| | 1339 | A | V | • | • | • | • | • | • | • | • | • | A |
| | 1399 | K | N | • | • | • | • | • | • | • | • | • | K |
| | 1503 | T | • | • | • | • | • | S | • | S | • | • | T |
| | 1528 | Y | • | • | • | • | • | • | • | • | • | • | Y |
| | 1535 | T | A | • | • | • | • | • | • | • | • | • | T |
| NS4A | 1662 | L | • | P | • | • | • | • | • | • | • | • | L |

FIG. 7C

| | L fragment | Cons-p9 | L1* (A) | L2(A) | L6(A) | L8(A) | L9(A) | L3(B) | L7*(B) | L10(B) | L4(C) | Cons-D | Cons-F |
|---|---|---|---|---|---|---|---|---|---|---|---|---|---|
| NS4B | 1753 | K | • | P | • | • | • | • | • | • | • | • | K |
| | 1805 | H | • | • | N | • | • | N | • | N | N | N | H,N |
| | 1949 | S | • | • | • | • | • | • | • | • | P | • | S |
| NS5A | 2105 | M | • | • | • | • | V | I | • | I | • | • | M |
| | 2136 | K | • | • | • | • | • | | • | • | R | • | K |
| | 2146 | T | • | • | • | • | • | A | A | A | • | T,A | T,A |
| | 2226 | L | • | • | • | • | • | P | • | • | • | • | L |
| | 2259 | L | • | • | • | • | • | F | • | • | • | • | L |
| | 2262 | E | • | • | • | • | • | D | D | D | • | E,D | E,D |
| | 2334 | V | • | • | • | • | • | I | • | • | • | • | V |
| | 2371 | L | • | • | • | • | • | Q | Q | Q | • | L,Q | L,Q |
| | 2385 | Y | • | • | • | • | • | • | • | • | H | • | Y |
| NS5B | 2692 | N | • | • | • | • | • | • | S | • | • | • | N |
| | 2757 | A | • | • | • | • | • | • | • | • | • | • | A |
| | 2785 | C | • | R | • | • | • | • | • | • | • | • | C |
| | 2824 | I | • | V | • | • | • | • | • | • | • | • | I |
| | 2861 | A | • | • | • | • | • | V | • | • | • | • | A |
| | S fragment | | S5 | S9 | S2 | S3 | S7 | S8 | S10 | S4 | S6 | | |
| | 2968 | G | • | • | • | • | • | S | S | • | • | • | G |
| | 2975 | S | • | • | • | • | • | G | G | G | G | • | S |
| | 2978 | D | • | • | • | • | • | • | • | • | G | • | D |
| | 2999 | S | • | F | F | F | • | • | • | • | • | • | S |

FIG. 7D

| aa \ nt | L1 (A) | L2 (A) | L6 (A) | L8 (A) | L9 (A) | L3 (B) | L7 (B) | L10 (B) | L4 (C) | HC-J4/91 | HC-J4/83 |
|---|---|---|---|---|---|---|---|---|---|---|---|
| L1 (A) | | 0.56 | 0.60 | 0.36 | 0.33 | 1.50 | 1.53 | 1.46 | 0.95 | 0.83 | 1.79 |
| L2 (A) | 0.59 | | 0.55 | 0.35 | 0.50 | 1.49 | 1.51 | 1.45 | 0.98 | 0.82 | 1.77 |
| L6 (A) | 0.52 | 0.42 | | 0.31 | 0.55 | 1.33 | 1.38 | 1.29 | 0.80 | 0.68 | 1.58 |
| L8 (A) | 0.42 | 0.38 | 0.31 | | 0.31 | 1.32 | 1.34 | 1.28 | 0.79 | 0.65 | 1.62 |
| L9 (A) | 0.35 | 0.52 | 0.45 | 0.35 | | 1.42 | 1.42 | 1.38 | 0.91 | 0.75 | 1.66 |
| L3 (B) | 1.47 | 1.43 | 1.15 | 1.33 | 1.36 | | 0.61 | 0.30 | 1.43 | 0.90 | 1.51 |
| L7 (B) | 1.36 | 1.33 | 1.05 | 1.22 | 1.22 | 0.66 | | 0.57 | 1.47 | 0.95 | 1.54 |
| L10 (B) | 1.36 | 1.33 | 0.59 | 1.22 | 1.26 | 0.31 | 0.56 | | 1.37 | 0.85 | 1.42 |
| L4 (C) | 0.77 | 0.80 | 0.59 | 0.63 | 1.26 | 1.12 | 1.08 | 1.01 | | 0.76 | 1.73 |
| HC-J4/91 | 0.94 | 0.91 | 0.63 | 0.80 | 0.87 | 0.77 | 0.73 | 0.66 | 0.52 | | 1.22 |
| HC-J4/83 | 1.96 | 1.89 | 1.68 | 1.85 | 1.82 | 1.75 | 1.61 | 1.61 | 1.71 | 1.40 | |

FIG. 8

```
                 379                                 413    468                   486
HC-J4L6  (A)  :  AGVDG ETHTTGRVAGHTTSGFTSLFSSGAS QKIQL  GWGPIT YTKPNSS DQRPYC
HC-J4L2  (A)  :  ..... ......................... .....  ...... ....... ......
HC-J4/91-20   :  ..... ..............R.......... .....  ...... ..E.... ......
HC-J4L1  (A)  :  ..... ........V................ .....  ...... ....... ......
HC-J4L8  (A)  :  ..... ........V................ .....  ...... ....... ......
HC-J4L9  (A)  :  ..... ........V................ .....  ...... ....... ......
HC-J4/91-21   :  ..... ........V................ .....  ...... ..G.... ......

HC-J4L4  (C)  :  ..... ........V.R.............. .....  ...... ..E.... ......
HC-J4/91-23   :  ..... ........V.R.............. .....  ...... ..E.... ......
HC-J4/91-22   :  ..... ........V.R.............. .....  .....A ..E.... ......

HC-J4L7  (B)  :  ..... T.Y.S.G...R..........P... .....  ...... ..E.... ......
HC-J4L10 (B)  :  T.... T.Y.S.GA..R.............. .....  ...... ..E.... ......
HC-J4L3  (B)  :  T.... T.Y.S.G...R.............. .....  ...... H.E.... ......
HC-J4/91-26   :  T.... T.Y.S.G...R.............. .....  ...... ..G.D.L ......
HC-J4/91-25   :  ..... A.Y.S.G...R.............. .....  ...... ..E.... ......
HC-J4/91-24   :  ..... A.Y.S.G...R.............. .....  ...... ..E...P ......
HC-J4/91      :  ..... A.Y.S.G...R.............. .....  ...... ..E...P ......

HC-J4/91-27   :  ..... K.Y.S.GA.S....R......P... .R...  ...... ..ESG.R ......
HC-J4/83      :  ..... ..Y.S.GA.S....TLA....P... .R...  ...... ..E.D.P ......
```

HVR1 HVR2

FIG. 10

5' Untranslated Region

```
             1                                                                                      90
HC-J4      :GCCAGCCCCC GATTGGGGGC GACACTCCAC CATAGATCAC TCCCCTGTGA GGAACTACTG TCTTCACGCA GAAAGCGTCT AGCCATGGCG
pCV-J4L6S:.......... TGA....... .......... ...GA..... .......... .......... .......... .......... ..........
pCV-H77C  :.......... TGA....... .......... ...GA..... .......... .......... .......... .......... ..........

             91                                                                                    180
HC-J4      :TTAGTATGAG TGTCGTGCAG CCTCCAGGAC CCCCCCTCCC GGGAGAGCCA TAGTGGTCTG CGGAACCGGT GAGTACACCG GAATTGCCAG
pCV-J4L6S:.......... .......... .......... .......... .......... .......... .......... .......... ..........
pCV-H77C  :.......... .......... .......... .......... .......... .......... .......... .......... ..........
                                                                                  Pin Al

             181                                                                                   270
HC-J4      :GACGACCGGG TCCTTTCTTG GATCAACCCG CTCAATGCCT GGAGATTTGG GCGTGCCCCC GCGAGACTGC TAGCCGAGTA GTGTTGGGTC
pCV-J4L6S:.......... .......... .......... .......... .......... .......... .......... .......... ..........
pCV-H77C  :.......... .......... ...A...... .......... .......... .......... ..A....... .......... ..........

             271                                                               341
HC-J4      :GCGAAAGGCC TTGTGGTACT GCCTGATAGG GTGCTTGCGA GTGCCCCGGG AGGTCTCGTA GACCGTGCAC C
pCV-J4L6S:.......... .......... .......... .......... .......... .......... .......... .
pCV-H77C  :.......... .......... .......... .......... .......... .......... .......... .
```

3' Untranslated Region

```
                  3' variable region              poly U-UC region    3' variable region
            <------------------------------------>  <---------->      <----------------
             9372                                                                9513
HC-J4      :TGAACGGGGA GCTAACCACT CCAGGCCAAT AGGCCTT--C CTG   poly (U-UC)n    ---GGTGGCT CCATCTTAG
pCV-J4L6S:.......... .......... ......-T. .A...A.TT. ...   poly (U-UC)81   AAT....... .........
pCV-H77C  :....G.TT.G .G...A.... ..G.C.TCT. .A...A.TT. ...   poly (U-UC)81   AAT....... .........
                                     Bfr 1

                                  3' conserved region (Cont.)
            ------------------------------------------------------------------------------------>
             9514                                                                        9595
H77        :CCCTAGTCAC GGCTAGCTGT GAAAGGTCCG TGAGCCGCAT GACTGCAGAG AGTGCTGATA CTGGCCTCTC TGCAGATCAT GT
pCV-J4L6S:.......... .......... .......... .......... .......... .......... .......... .......... ..
pCV-H77C  :.......... .......... .......... .......... .......... .......... .......... .......... ..
```

| 10 | 20 | 30 | 40 | 50 | |
|---|---|---|---|---|---|
| 1234567890 | 1234567890 | 1234567890 | 1234567890 | 1234567890 | |
| GCCAGCCCCC | TGATGGGGGC | GACACTCCAC | CATGAATCAC | TCCCCTGTGA | 50 |
| GGAACTACTG | TCTTCACGCA | GAAAGCGTCT | AGCCATGGCG | TTAGTATGAG | 100 |
| TGTCGTGCAG | CCTCCAGGAC | CCCCCCTCCC | GGGAGAGCCA | TAGTGGTCTG | 150 |
| CGGAACCGGT | GAGTACACCG | GAATTGCCAG | GACGACCGGG | TCCTTTCTTG | 200 |
| GATCAACCCG | CTCAATGCCT | GGAGATTTGG | GCGTGCCCCC | GCGAGACTGC | 250 |
| TAGCCGAGTA | GTGTTGGGTC | GCGAAAGGCC | TTGTGGTACT | GCCTGATAGG | 300 |
| GTGCTTGCGA | GTGCCCCGGG | AGGTCTCGTA | GACCGTGCAC | CATGAGCACG | 350 |
| AATCCTAAAC | CTCAAAGAAA | AACCAAACGT | AACACCAACC | GCCGCCCACA | 400 |
| GGACGTCAAG | TTCCCGGGCG | GTGGTCAGAT | CGTTGGTGGA | GTTTACCTGT | 450 |
| TGCCGCGCAG | GGGCCCCAGG | TTGGGTGTGC | GCGCGACTAG | GAAGGCTTCC | 500 |
| GAGCGGTCGC | AACCTCGTGG | AAGGCGACAA | CCTATCCCAA | AGGCTCGCCG | 550 |
| ACCCGAGGGC | AGGGCCTGGG | CTCAGCCCGG | GTACCCTTGG | CCCCTCTATG | 600 |
| GCAATGAGGG | CCTGGGGTGG | GCAGGATGGC | TCCTGTCACC | CCGCGGCTCC | 650 |
| CGGCCTAGTT | GGGGCCCCAC | GGACCCCCGG | CGTAGGTCGC | GTAACTTGGG | 700 |
| TAAGGTCATC | GATACCCTTA | CATGCGGCTT | CGCCGATCTC | ATGGGGTACA | 750 |
| TTCCGCTCGT | CGGCGCCCCC | CTAGGGGGCG | CTGCCAGGGC | CTTGGCACAC | 800 |
| GGTGTCCGGG | TTCTGGAGGA | CGGCGTGAAC | TATGCAACAG | GGAACTTGCC | 850 |
| CGGTTGCTCT | TTCTCTATCT | TCCTCTTGGC | TCTGCTGTCC | TGTTTGACCA | 900 |
| TCCCAGCTTC | CGCTTATGAA | GTGCGCAACG | TGTCCGGGAT | ATACCATGTC | 950 |
| ACGAACGACT | GCTCCAACTC | AAGCATTGTG | TATGAGGCAG | CGGACGTGAT | 1000 |
| CATGCATACT | CCCGGGTGCG | TGCCCTGTGT | TCAGGAGGGT | AACAGCTCCC | 1050 |
| GTTGCTGGGT | AGCGCTCACT | CCCACGCTCG | CGGCCAGGAA | TGCCAGCGTC | 1100 |
| CCCACTACGA | CAATACGACG | CCACGTCGAC | TTGCTCGTTG | GGACGGCTGC | 1150 |
| TTTCTGCTCC | GCTATGTACG | TGGGGGATCT | CTGCGGATCT | ATTTTCCTCG | 1200 |
| TCTCCCAGCT | GTTCACCTTC | TCGCCTCGCC | GGCATGAGAC | AGTGCAGGAC | 1250 |
| TGCAACTGCT | CAATCTATCC | CGGCCATGTA | TCAGGTCACC | GCATGGCTTG | 1300 |
| GGATATGATG | ATGAACTGGT | CACCTACAAC | AGCCCTAGTG | GTGTCGCAGT | 1350 |
| TGCTCCGGAT | CCCACAAGCT | GTCGTGGACA | TGGTGGCGGG | GGCCCACTGG | 1400 |
| GGAGTCCTGG | CGGGCCTTGC | CTACTATTCC | ATGGTAGGGA | ACTGGGCTAA | 1450 |
| GGTTCTGATT | GTGGCGCTAC | TCTTTGCCGG | CGTTGACGGG | GAGACCCACA | 1500 |
| CGACGGGGAG | GGTGGCCGGC | CACACCACCT | CCGGGTTCAC | GTCCCTTTTC | 1550 |
| TCATCTGGGG | CGTCTCAGAA | AATCCAGCTT | GTGAATACCA | ACGGCAGCTG | 1600 |
| GCACATCAAC | AGGACTGCCC | TAAATTGCAA | TGACTCCCTC | CAAACTGGGT | 1650 |
| TCTTTGCCGC | GCTGTTTTAC | GCACACAAGT | TCAACTCGTC | CGGGTGCCCG | 1700 |
| GAGCGCATGG | CCAGCTGCCG | CCCCATTGAC | TGGTTCGCCC | AGGGGTGGGG | 1750 |
| CCCCATCACC | TATACTAAGC | CTAACAGCTC | GGATCAGAGG | CCTTATTGCT | 1800 |
| GGCATTACGC | GCCTCGACCG | TGTGGTGTCG | TACCCGCGTC | GCAGGTGTGT | 1850 |
| GGTCCAGTGT | ATTGTTTCAC | CCCAAGCCCT | GTTGTGGTGG | GGACCACCGA | 1900 |

```
        10         20         30         40         50
1234567890 1234567890 1234567890 1234567890 1234567890
TCGTTCCGGT GTCCCTACGT ATAGCTGGGG GGAGAATGAG ACAGACGTGA   1950
TGCTCCTCAA CAACACGCGT CCGCCACAAG GCAACTGGTT CGGCTGTACA   2000
TGGATGAATA GTACTGGGTT CACTAAGACG TGCGGAGGTC CCCCGTGTAA   2050
CATCGGGGG GTCGGTAACC GCACCTTGAT CTGCCCCACG GACTGCTTCC   2100
GGAAGCACCC CGAGGCTACT TACACAAAAT GTGGCTCGGG GCCCTGGTTG   2150
ACACCTAGGT GCCTAGTAGA CTACCCATAC AGGCTTTGGC ACTACCCCTG   2200
CACTCTCAAT TTTTCCATCT TTAAGGTTAG GATGTATGTG GGGGGCGTGG   2250
AGCACAGGCT CAATGCCGCA TGCAATTGGA CTCGAGGAGA GCGCTGTAAC   2300
TTGGAGGACA GGGATAGGTC AGAACTCAGC CCGCTGCTGC TGTCTACAAC   2350
AGAGTGGCAG ATACTGCCCT GTGCTTTCAC CACCCTACCG GCTTTATCCA   2400
CTGGTTTGAT CCATCTCCAT CAGAACATCG TGGACGTGCA ATACCTGTAC   2450
GGTGTAGGGT CAGCGTTTGT CTCCTTTGCA ATCAAATGGG AGTACATCCT   2500
GTTGCTTTTC CTTCTCCTGG CAGACGCGCG CGTGTGTGCC TGCTTGTGGA   2550
TGATGCTGCT GATAGCCCAG GCTGAGGCCG CCTTAGAGAA CTTGGTGGTC   2600
CTCAATGCGG CGTCCGTGGC CGGAGCGCAT GGTATTCTCT CCTTTCTTGT   2650
GTTCTTCTGC GCCGCCTGGT ACATTAAGGG CAGGCTGGCT CCTGGGGCGG   2700
CGTATGCTTT TTATGGCGTA TGGCCGCTGC TCCTGCTCCT ACTGGCGTTA   2750
CCACCACGAG CTTACGCCTT GGACCGGGAG ATGGCTGCAT CGTGCGGGGG   2800
TGCGGTTCTT GTAGGTCTGG TATTCTTGAC CTTGTCACCA TACTACAAAG   2850
TGTTTCTCAC TAGGCTCATA TGGTGGTTAC AATACTTTAT CACCAGAGCC   2900
GAGGCGCACA TGCAAGTGTG GGTCCCCCCC CTCAACGTTC GGGGAGGCCG   2950
CGATGCCATC ATCCTCCTCA CGTGTGCGGT TCATCCAGAG TTAATTTTTG   3000
ACATCACCAA ACTCCTGCTC GCCATACTCG GCCCGCTCAT GGTGCTCCAG   3050
GCTGGCATAA CGAGAGTGCC GTACTTCGTG CGCGCTCAAG GGCTCATTCG   3100
TGCATGCATG TTAGTGCGAA AAGTCGCCGG GGGTCATTAT GTCCAAATGG   3150
TCTTCATGAA GCTGGCGCGG CTGACAGGTA CGTACGTTTA TAACCATCTT   3200
ACCCCACTGC GGGACTGGGC CCACGCGGGC CTACGAGACC TTGCGGTGGC   3250
GGTAGAGCCC GTCGTCTTCT CCGCCATGGA GACCAAGGTC ATCACCTGGG   3300
GAGCAGACAC CGCTGCGTGT GGGGACATCA TCTTGGGTCT ACCCGTCTCC   3350
GCCCGAAGGG GGAAGGAGAT ATTTTTGGGA CCGGCTGATA GTCTCGAAGG   3400
GCAAGGGTGG CGACTCCTTG CGCCCATCAC GGCCTACTCC CAACAAACGC   3450
GGGGCGTACT TGGTTGCATC ATCACTAGCC TCACAGGCCG GGACAAGAAC   3500
CAGGTCGAAG GGGAGGTTCA AGTGGTTTCT ACCGCAACAC AATCTTTCCT   3550
GGCGACCTGC ATCAACGGCG TGTGCTGGAC TGTCTACCAT GGCGCTGGCT   3600
CGAAGACCCT AGCCGGTCCA AAAGGTCCAA TCACCCAAAT GTACACCAAT   3650
GTAGACCTGG ACCTCGTCGG CTGGCAGGCG CCCCCCGGGG CGCGCTCCAT   3700
GACACCATGC AGCTGTGGCA GCTCGGACCT TTACTTGGTC ACGAGACATG   3750
CTGATGTCAT TCCGGTGCGC CGGCGAGGCG ACAGCAGGGG AAGTCTACTC   3800
```

| 10<br>1234567890 | 20<br>1234567890 | 30<br>1234567890 | 40<br>1234567890 | 50<br>1234567890 | |
|---|---|---|---|---|---|
| TCCCCCAGGC | CCGTCTCCTA | CCTGAAAGGC | TCCTCGGGTG | GTCCATTGCT | 3850 |
| TTGCCCTTCG | GGGCACGTCG | TGGGCGTCTT | CCGGGCTGCT | GTGTGCACCC | 3900 |
| GGGGGGTCGC | GAAGGCGGTG | GACTTCATAC | CCGTTGAGTC | TATGGAAACT | 3950 |
| ACCATGCGGT | CTCCGGTCTT | CACAGACAAC | TCAACCCCCC | CGGCTGTACC | 4000 |
| GCAGACATTC | CAAGTGGCAC | ATCTGCACGC | TCCTACTGGC | AGCGGCAAGA | 4050 |
| GCACCAAAGT | GCCGGCTGCG | TATGCAGCCC | AAGGGTACAA | GGTGCTCGTC | 4100 |
| CTGAACCCGT | CCGTTGCCGC | CACCTTAGGG | TTTGGGGCGT | ATATGTCCAA | 4150 |
| GGCACACGGT | ATCGACCCTA | ACATCAGAAC | TGGGGTAAGG | ACCATTACCA | 4200 |
| CGGGCGGCTC | CATTACGTAC | TCCACCTATG | GCAAGTTCCT | TGCCGACGGT | 4250 |
| GGCTGTTCTG | GGGGCGCCTA | TGACATCATA | ATATGTGATG | AGTGCCACTC | 4300 |
| AACTGACTCG | ACTACCATCT | TGGGCATCGG | CACAGTCCTG | GACCAAGCGG | 4350 |
| AGACGGCTGG | AGCGCGGCTC | GTCGTGCTCG | CCACCGCTAC | ACCTCCGGGA | 4400 |
| TCGGTTACCG | TGCCACACCC | CAATATCGAG | GAAATAGGCC | TGTCCAACAA | 4450 |
| TGGAGAGATC | CCCTTCTATG | GCAAAGCCAT | CCCCATTGAG | GCCATCAAGG | 4500 |
| GGGGGAGGCA | TCTCATTTTC | TGCCATTCCA | AGAAGAAATG | TGACGAGCTC | 4550 |
| GCCGCAAAGC | TGACAGGCCT | CGGACTGAAC | GCTGTAGCAT | ATTACCGGGG | 4600 |
| CCTTGATGTG | TCCGTCATAC | CGCCTATCGG | AGACGTCGTT | GTCGTGGCAA | 4650 |
| CAGACGCTCT | AATGACGGGT | TTCACCGGCG | ATTTTGACTC | AGTGATCGAC | 4700 |
| TGCAATACAT | GTGTCACCCA | GACAGTCGAC | TTCAGCTTGG | ATCCCACCTT | 4750 |
| CACCATTGAG | ACGACGACCG | TGCCCCAAGA | CGCGGTGTCG | CGCTCGCAAC | 4800 |
| GGCGAGGTAG | AACTGGCAGG | GGTAGGAGTG | GCATCTACAG | GTTTGTGACT | 4850 |
| CCAGGAGAAC | GGCCCTCGGG | CATGTTCGAT | TCTTCGGTCC | TGTGTGAGTG | 4900 |
| CTATGACGCG | GGCTGTGCTT | GGTATGAGCT | CACGCCCGCT | GAGACCTCGG | 4950 |
| TTAGGTTGCG | GGCTTACCTA | AATACACCAG | GGTTGCCCGT | CTGCCAGGAC | 5000 |
| CATCTGGAGT | TCTGGGAGAG | CGTCTTCACA | GGCCTCACCC | ACATAGATGC | 5050 |
| CCACTTCCTG | TCCCAGACTA | AACAGGCAGG | AGACAACTTT | CCTTACCTGG | 5100 |
| TGGCATATCA | AGCTACAGTG | TGCGCCAGGG | CTCAAGCTCC | ACCTCCATCG | 5150 |
| TGGGACCAAA | TGTGGAAGTG | TCTCATACGG | CTGAAACCTA | CACTGCACGG | 5200 |
| GCCAACACCC | CTGCTGTATA | GGCTAGGAGC | CGTCCAAAAT | GAGGTCATCC | 5250 |
| TCACACACCC | CATAACTAAA | TACATCATGG | CATGCATGTC | GGCTGACCTG | 5300 |
| GAGGTCGTCA | CTAGCACCTG | GGTGCTGGTA | GGCGGAGTCC | TTGCAGCTTT | 5350 |
| GGCCGCATAC | TGCCTGACGA | CAGGCAGTGT | GGTCATTGTG | GGCAGGATCA | 5400 |
| TCTTGTCCGG | GAAGCCAGCT | GTCGTTCCCG | ACAGGGAAGT | CCTCTACCAG | 5450 |
| GAGTTCGATG | AGATGGAAGA | GTGTGCCTCA | CAACTTCCTT | ACATCGAGCA | 5500 |
| GGGAATGCAG | CTCGCCGAGC | AATTCAAGCA | AAAGGCGCTC | GGGTTGTTGC | 5550 |
| AAACGGCCAC | CAAGCAAGCG | GAGGCTGCTG | CTCCCGTGGT | GGAGTCCAAG | 5600 |
| TGGCGAGCCC | TTGAGACCTT | CTGGGCGAAG | CACATGTGGA | ATTTCATCAG | 5650 |
| CGGAATACAG | TACCTAGCAG | GCTTATCCAC | TCTGCCTGGA | AACCCCGCGA | 5700 |

| 10<br>1234567890 | 20<br>1234567890 | 30<br>1234567890 | 40<br>1234567890 | 50<br>1234567890 | |
|---|---|---|---|---|---|
| TAGCATCATT | GATGGCATTT | ACAGCTTCTA | TCACTAGCCC | GCTCACCACC | 5750 |
| CAAAACACCC | TCCTGTTTAA | CATCTTGGGG | GGATGGGTGG | CTGCCCAACT | 5800 |
| CGCTCCTCCC | AGCGCTGCGT | CAGCTTTCGT | GGGCGCCGGC | ATCGCCGGAG | 5850 |
| CGGCTGTTGG | CAGCATAGGC | CTTGGGAAGG | TGCTCGTGGA | CATCTTGGCG | 5900 |
| GGCTATGGGG | CAGGGGTAGC | CGGCGCACTC | GTGGCCTTTA | AGGTCATGAG | 5950 |
| CGGCGAGGTG | CCCTCCACCG | AGGACCTGGT | CAACTTACTC | CCTGCCATCC | 6000 |
| TCTCTCCTGG | TGCCCTGGTC | GTCGGGGTCG | TGTGCGCAGC | AATACTGCGT | 6050 |
| CGGCACGTGG | GCCCGGGAGA | GGGGGCTGTG | CAGTGGATGA | ACCGGCTGAT | 6100 |
| AGCGTTCGCT | TCGCGGGGTA | ACCACGTCTC | CCCTACGCAC | TATGTGCCTG | 6150 |
| AGAGCGACGC | TGCAGCACGT | GTCACTCAGA | TCCTCTCTAG | CCTTACCATC | 6200 |
| ACTCAACTGC | TGAAGCGGCT | CCACCAGTGG | ATTAATGAGG | ACTGCTCTAC | 6250 |
| GCCATGCTCC | GGCTCGTGGC | TAAGGGATGT | TTGGGATTGG | ATATGCACGG | 6300 |
| TGTTGACTGA | CTTCAAGACC | TGGCTCCAGT | CCAAACTCCT | GCCGCGGTTA | 6350 |
| CCGGGAGTCC | CTTTCCTGTC | ATGCCAACGC | GGGTACAAGG | GAGTCTGGCG | 6400 |
| GGGGGACGGC | ATCATGCAAA | CCACCTGCCC | ATGCGGAGCA | CAGATCGCCG | 6450 |
| GACATGTCAA | AAACGGTTCC | ATGAGGATCG | TAGGGCCTAG | AACCTGCAGC | 6500 |
| AACACGTGGC | ACGGAACGTT | CCCCATCAAC | GCATACACCA | CGGGACCTTG | 6550 |
| CACACCCTCC | CCGGCGCCCA | ACTATTCCAG | GGCGCTATGG | CGGGTGGCTG | 6600 |
| CTGAGGAGTA | CGTGGAGGTT | ACGCGTGTGG | GGGATTTCCA | CTACGTGACG | 6650 |
| GGCATGACCA | CTGACAACGT | AAAGTGCCCA | TGCCAGGTTC | CGGCCCCCGA | 6700 |
| ATTCTTCACG | GAGGTGGATG | GAGTGCGGTT | GCACAGGTAC | GCTCCGGCGT | 6750 |
| GCAAACCTCT | TCTACGGGAG | GACGTCACGT | TCCAGGTCGG | GCTCAACCAA | 6800 |
| TACTTGGTCG | GGTCGCAGCT | CCCATGCGAG | CCCGAACCGG | ACGTAACAGT | 6850 |
| GCTTACTTCC | ATGCTCACCG | ATCCCTCCCA | CATTACAGCA | GAGACGGCTA | 6900 |
| AGCGTAGGCT | GGCTAGAGGG | TCTCCCCCCT | CTTTAGCCAG | CTCATCAGCT | 6950 |
| AGCCAGTTGT | CTGCGCCTTC | TTTGAAGGCG | ACATGCACTA | CCCACCATGA | 7000 |
| CTCCCCCGGAC | GCTGACCTCA | TCGAGGCCAA | CCTCTTGTGG | CGGCAGGAGA | 7050 |
| TGGGCGGAAA | CATCACTCGC | GTGGAGTCAG | AGAATAAGGT | AGTAATTCTG | 7100 |
| GACTCTTTCG | AACCGCTTCA | CGCGGAGGGG | GATGAGAGGG | AGATATCCGT | 7150 |
| CGCGGCGGAG | ATCCTGCGAA | AATCCAGGAA | GTTCCCCTCA | GCGTTGCCCA | 7200 |
| TATGGGCACG | CCCGGACTAC | AATCCTCCAC | TGCTAGAGTC | CTGGAAGGAC | 7250 |
| CCGGACTACG | TCCCTCCGGT | GGTACACGGA | TGCCCATTGC | CACCTACCAA | 7300 |
| GGCTCCTCCA | ATACCACCTC | CACGGAGAAA | GAGGACGGTT | GTCCTGACAG | 7350 |
| AATCCAATGT | GTCTTCTGCC | TTGGCGGAGC | TCGCCACTAA | GACCTTCGGT | 7400 |
| AGCTCCGGAT | CGTCGGCCGT | TGATAGCGGC | ACGGCGACCG | CCCTTCCTGA | 7450 |
| CCTGGCCTCC | GACGACGGTG | ACAAAGGATC | CGACGTTGAG | TCGTACTCCT | 7500 |
| CCATGCCCCC | CCTTGAAGGG | GAGCCGGGGG | ACCCCGATCT | CAGCGACGGG | 7550 |
| TCTTGGTCTA | CCGTGAGTGA | GGAGGCTAGT | GAGGATGTCG | TCTGCTGCTC | 7600 |

| 10<br>1234567890 | 20<br>1234567890 | 30<br>1234567890 | 40<br>1234567890 | 50<br>1234567890 | |
|---|---|---|---|---|---|
| AATGTCCTAT | ACGTGGACAG | GCGCCCTGAT | CACGCCATGC | GCTGCGGAGG | 7650 |
| AAAGTAAGCT | GCCCATCAAC | CCGTTGAGCA | ACTCTTTGCT | GCGTCACCAC | 7700 |
| AACATGGTCT | ACGCCACAAC | ATCCCGCAGC | GCAAGCCTCC | GGCAGAAGAA | 7750 |
| GGTCACCTTT | GACAGATTGC | AAGTCCTGGA | TGATCATTAC | CGGGACGTAC | 7800 |
| TCAAGGAGAT | GAAGGCGAAG | GCGTCCACAG | TTAAGGCTAA | GCTTCTATCT | 7850 |
| ATAGAGGAGG | CCTGCAAGCT | GACGCCCCCA | CATTCGGCCA | AATCCAAATT | 7900 |
| TGGCTATGGG | GCAAAGGACG | TCCGGAACCT | ATCCAGCAGG | GCCGTTAACC | 7950 |
| ACATCCGCTC | CGTGTGGGAG | GACTTGCTGG | AAGACACTGA | AACACCAATT | 8000 |
| GACACCACCA | TCATGGCAAA | AAGTGAGGTT | TTCTGCGTCC | AACCAGAGAA | 8050 |
| GGGAGGCCGC | AAGCCAGCTC | GCCTTATCGT | ATTCCCAGAC | CTGGGAGTTC | 8100 |
| GTGTATGCGA | GAAGATGGCC | CTTTACGACG | TGGTCTCCAC | CCTTCCTCAG | 8150 |
| GCCGTGATGG | GCTCCTCATA | CGGATTTCAA | TACTCCCCCA | AGCAGCGGGT | 8200 |
| CGAGTTCCTG | GTGAATACCT | GGAAATCAAA | GAAATGCCCT | ATGGGCTTCT | 8250 |
| CATATGACAC | CCGCTGTTTT | GACTCAACGG | TCACTGAGAG | TGACATTCGT | 8300 |
| GTTGAGGAGT | CAATTTACCA | ATGTTGTGAC | TTGGCCCCCG | AGGCCAGACA | 8350 |
| GGCCATAAGG | TCGCTCACAG | AGCGGCTTTA | CATCGGGGGT | CCCCTGACTA | 8400 |
| ACTCAAAAGG | GCAGAACTGC | GGTTATCGCC | GGTGCCGCGC | AAGTGGCGTG | 8450 |
| CTGACGACTA | GCTGCGGTAA | TACCCTCACA | TGTTACTTGA | AGGCCACTGC | 8500 |
| AGCCTGTCGA | GCTGCAAAGC | TCCAGGACTG | CACGATGCTC | GTGAACGGAG | 8550 |
| ACGACCTTGT | CGTTATCTGT | GAAAGCGCGG | GAACCCAGGA | GGATGCGGCG | 8600 |
| GCCCTACGAG | CCTTCACGGA | GGCTATGACT | AGGTATTCCG | CCCCCCCCGG | 8650 |
| GGATCCGCCC | CAACCAGAAT | ACGACCTGGA | GCTGATAACA | TCATGTTCCT | 8700 |
| CCAATGTGTC | AGTCGCGCAC | GATGCATCTG | GCAAAAGGGT | ATACTACCTC | 8750 |
| ACCCGTGACC | CCACCACCCC | CCTTGCACGG | GCTGCGTGGG | AGACAGCTAG | 8800 |
| ACACACTCCA | ATCAACTCTT | GGCTAGGCAA | TATCATCATG | TATGCGCCCA | 8850 |
| CCCTATGGGC | AAGGATGATT | CTGATGACTC | ACTTTTTCTC | CATCCTTCTA | 8900 |
| GCTCAAGAGC | AACTTGAAAA | AGCCCTGGAT | TGTCAGATCT | ACGGGGCTTG | 8950 |
| CTACTCCATT | GAGCCACTTG | ACCTACCTCA | GATCATTGAA | CGACTCCATG | 9000 |
| GTCTTAGCGC | ATTTACACTC | CACAGTTACT | CTCCAGGTGA | GATCAATAGG | 9050 |
| GTGGCTTCAT | GCCTCAGGAA | ACTTGGGGTA | CCACCCTTGC | GAACCTGGAG | 9100 |
| ACATCGGGCC | AGAAGTGTCC | GCGCTAAGCT | ACTGTCCCAG | GGGGGGAGGG | 9150 |
| CCGCCACTTG | TGGCAGATAC | CTCTTTAACT | GGGCAGTAAG | GACCAAGCTT | 9200 |
| AAACTCACTC | CAATCCCGGC | CGCGTCCCAG | CTGGACTTGT | CTGGCTGGTT | 9250 |
| CGTCGCTGGT | TACAGCGGGG | GAGACATATA | TCACAGCCTG | TCTCGTGCCC | 9300 |
| GACCCCGCTG | GTTTCCGTTG | TGCCTACTCC | TACTTTCTGT | AGGGGTAGGC | 9350 |
| ATTTACCTGC | TCCCCAACCG | ATGAACGGGG | AGCTAACCAC | TCCAGGCCTT | 9400 |
| AAGCCATTTC | CTGTTTTTTT | TTTTTTTTTT | TTTTTTTTTT | TCTTTTTTTT | 9450 |
| TTTCTTTCCT | TTCCTTCTTT | TTTTCCTTTC | TTTTTCCCTT | CTTTAATGGT | 9500 |

| | | | | | |
|---|---|---|---|---|---|
| 10 | 20 | 30 | 40 | 50 | |
| 1234567890 | 1234567890 | 1234567890 | 1234567890 | 1234567890 | |
| GGCTCCATCT | TAGCCCTAGT | CACGGCTAGC | TGTGAAAGGT | CCGTGAGCCG | 9550 |
| CATGACTGCA | GAGAGTGCTG | ATACTGGCCT | CTCTGCAGAT | CATGT | 9595 |

| 10<br>1234567890 | 20<br>1234567890 | 30<br>1234567890 | 40<br>1234567890 | 50<br>1234567890 | |
|---|---|---|---|---|---|
| MSTNPKPQRK | TKRNTNRRPQ | DVKFPGGGQI | VGGVYLLPRR | GPRLGVRATR | 50 |
| KASERSQPRG | RRQPIPKARR | PEGRAWAQPG | YPWPLYGNEG | LGWAGWLLSP | 100 |
| RGSRPSWGPT | DPRRRSRNLG | KVIDTLTCGF | ADLMGYIPLV | GAPLGGAARA | 150 |
| LAHGVRVLED | GVNYATGNLP | GCSFSIFLLA | LLSCLTIPAS | AYEVRNVSGI | 200 |
| YHVTNDCSNS | SIVYEAADVI | MHTPGCVPCV | QEGNSSRCWV | ALTPTLAARN | 250 |
| ASVPTTTIRR | HVDLLVGTAA | FCSAMYVGDL | CGSIFLVSQL | FTFSPRRHET | 300 |
| VQDCNCSIYP | GHVSGHRMAW | DMMMNWSPTT | ALVVSQLLRI | PQAVVDMVAG | 350 |
| AHWGVLAGLA | YYSMVGNWAK | VLIVALLFAG | VDGETHTTGR | VAGHTTSGFT | 400 |
| SLFSSGASQK | IQLVNTNGSW | HINRTALNCN | DSLQTGFFAA | LFYAHKFNSS | 450 |
| GCPERMASCR | PIDWFAQGWG | PITYTKPNSS | DQRPYCWHYA | PRPCGVVPAS | 500 |
| QVCGPVYCFT | PSPVVVGTTD | RSGVPTYSWG | ENETDVMLLN | NTRPPQGNWF | 550 |
| GCTWMNSTGF | TKTCGGPPCN | IGGVGNRTLI | CPTDCFRKHP | EATYTKCGSG | 600 |
| PWLTPRCLVD | YPYRLWHYPC | TLNFSIFKVR | MYVGGVEHRL | NAACNWTRGE | 650 |
| RCNLEDRDRS | ELSPLLLSTT | EWQILPCAFT | TLPALSTGLI | HLHQNIVDVQ | 700 |
| YLYGVGSAFV | SFAIKWEYIL | LLFLLLADAR | VCACLWMMLL | IAQAEAALEN | 750 |
| LVVLNAASVA | GAHGILSFLV | FFCAAWYIKG | RLAPGAAYAF | YGVWPLLLLL | 800 |
| LALPPRAYAL | DREMAASCGG | AVLVGLVFLT | LSPYYKVFLT | RLIWWLQYFI | 850 |
| TRAEAHMQVW | VPPLNVRGGR | DAIILLTCAV | HPELIFDITK | LLLAILGPLM | 900 |
| VLQAGITRVP | YFVRAQGLIR | ACMLVRKVAG | GHYVQMVFMK | LGALTGTYVY | 950 |
| NHLTPLRDWA | HAGLRDLAVA | VEPVVFSAME | TKVITWGADT | AACGDIILGL | 1000 |
| PVSARRGKEI | FLGPADSLEG | QGWRLLAPIT | AYSQQTRGVL | GCIITSLTGR | 1050 |
| DKNQVEGEVQ | VVSTATQSFL | ATCINGVCWT | VYHGAGSKTL | AGPKGPITQM | 1100 |
| YTNVDLDLVG | WQAPPGARSM | TPCSCGSSDL | YLVTRHADVI | PVRRRGDSRG | 1150 |
| SLLSPRPVSY | LKGSSGGPLL | CPSGHVVGVF | RAAVCTRGVA | KAVDFIPVES | 1200 |
| METTMRSPVF | TDNSTPPAVP | QTFQVAHLHA | PTGSGKSTKV | PAAYAAQGYK | 1250 |
| VLVLNPSVAA | TLGFGAYMSK | AHGIDPNIRT | GVRTITTGGS | ITYSTYGKFL | 1300 |
| ADGGCSGGAY | DIIICDECHS | TDSTTILGIG | TVLDQAETAG | ARLVVLATAT | 1350 |
| PPGSVTVPHP | NIEEIGLSNN | GEIPFYGKAI | PIEAIKGGRH | LIFCHSKKKC | 1400 |
| DELAAKLTGL | GLNAVAYYRG | LDVSVIPPIG | DVVVVATDAL | MTGFTGDFDS | 1450 |
| VIDCNTCVTQ | TVDFSLDPTF | TIETTTVPQD | AVSRSQRRGR | TGRGRSGIYR | 1500 |
| FVTPGERPSG | MFDSSVLCEC | YDAGCAWYEL | TPAETSVRLR | AYLNTPGLPV | 1550 |
| CQDHLEFWES | VFTGLTHIDA | HFLSQTKQAG | DNFPYLVAYQ | ATVCARAQAP | 1600 |
| PPSWDQMWKC | LIRLKPTLHG | PTPLLYRLGA | VQNEVILTHP | ITKYIMACMS | 1650 |
| ADLEVVTSTW | VLVGGVLAAL | AAYCLTTGSV | VIVGRIILSG | KPAVVPDREV | 1700 |
| LYQEFDEMEE | CASQLPYIEQ | GMQLAEQFKQ | KALGLLQTAT | KQAEAAAPVV | 1750 |
| ESKWRALETF | WAKHMWNFIS | GIQYLAGLST | LPGNPAIASL | MAFTASITSP | 1800 |
| LTTQNTLLFN | ILGGWVAAQL | APPSAASAFV | GAGIAGAAVG | SIGLGKVLVD | 1850 |
| ILAGYGAGVA | GALVAFKVMS | GEVPSTEDLV | NLLPAILSPG | ALVVGVVCAA | 1900 |

| 10<br>1234567890 | 20<br>1234567890 | 30<br>1234567890 | 40<br>1234567890 | 50<br>1234567890 | |
|---|---|---|---|---|---|
| ILRRHVGPGE | GAVQWMNRLI | AFASRGNHVS | PIHYVPESDA | AARVTQILSS | 1950 |
| LTTTQLLKRL | HQWINEDCST | PCSGSWLRDV | WDWICTVLTD | FKTWLQSKLL | 2000 |
| PRLPGVPFLS | CQRGYKGVWR | GDGIMQTTCP | CGAQIAGHVK | NGSMRIVGPR | 2050 |
| TCSNTWHGTF | PINAYTTGPC | TPSPAPNYSR | ALWRVAAEEY | VEVTRVGDFH | 2100 |
| YVTGMTTDNV | KCPCQVPAPE | FFTEVDGVRL | HRYAPACKPL | LREDVTFQVG | 2150 |
| LNQYLVGSQL | PCEPEPDVTV | LTSMLTDPSH | ITAETAKRRL | ARGSPPSLAS | 2200 |
| SSASQLSAPS | LKATCTTHHD | SPDADLIEAN | LLWRQEMGGN | ITRVESENKV | 2250 |
| VILDSFEPLH | AEGDEREISV | AAEILRKSRK | FPSALPIWAR | PDYNPPLLES | 2300 |
| WKDPDYVPPV | VHGCPLPPTK | APPIPPPRRK | RTVVLTESNV | SSALAELATK | 2350 |
| TFGSSGSSAV | DSGTATALPD | LASDDGDKGS | DVESYSSMPP | LEGEPGDPDL | 2400 |
| SDGSWSTVSE | EASEDVVCCS | MSYTWTGALI | TPCAAEESKL | PINPLSNSLL | 2450 |
| RHHNMVYATT | SRSASLRQKK | VTFDRLQVLD | DHYRDVLKEM | KAKASTVKAK | 2500 |
| LLSIEEACKL | TPPHSAKSKF | GYGAKDVRNL | SSRAVNHIRS | VWEDLLEDTE | 2550 |
| TPIDTTIMAK | SEVFCVQPEK | GGRKPARLIV | FPDLGVRVCE | KMALYDVVST | 2600 |
| LPQAVMGSSY | GFQYSPKQRV | EFLVNTWKSK | KCPMGFSYDT | RCFDSTVTES | 2650 |
| DIRVEESIYQ | CCDLAPEARQ | AIRSLTERLY | IGGPLTNSKG | QNCGYRRCRA | 2700 |
| SGVLTTSCGN | TLTCYLKATA | ACRAAKLQDC | TMLVNGDDLV | VICESAGTQE | 2750 |
| DAAALRAFTE | AMTRYSAPPG | DPPQPEYDLE | LITSCSSNVS | VAHDASGKRV | 2800 |
| YYLTRDPTTP | LARAAWETAR | HTPINSWLGN | IIMYAPTLWA | RMILMTHFFS | 2850 |
| ILLAQEQLEK | ALDCQIYGAC | YSIEPLDLPQ | IIERLHGLSA | FTLHSYSPGE | 2900 |
| INRVASCLRK | LGVPPLRTWR | HRARSVRAKL | LSQGGRAATC | GRYLFNWAVR | 2950 |
| TKLKLTPIPA | ASQLDLSGWF | VAGYSGGDIY | HSLSRARPRW | FPLCLLLLSV | 3000 |
| GVGIYLLPNR | | | | | 3010 |

FIG. 14H

2. Strategy for constructing chimeric clone of HCV (pH77CV-J4) which contains the nonstructural region of strain H77 and the structural region of strain HC-J4

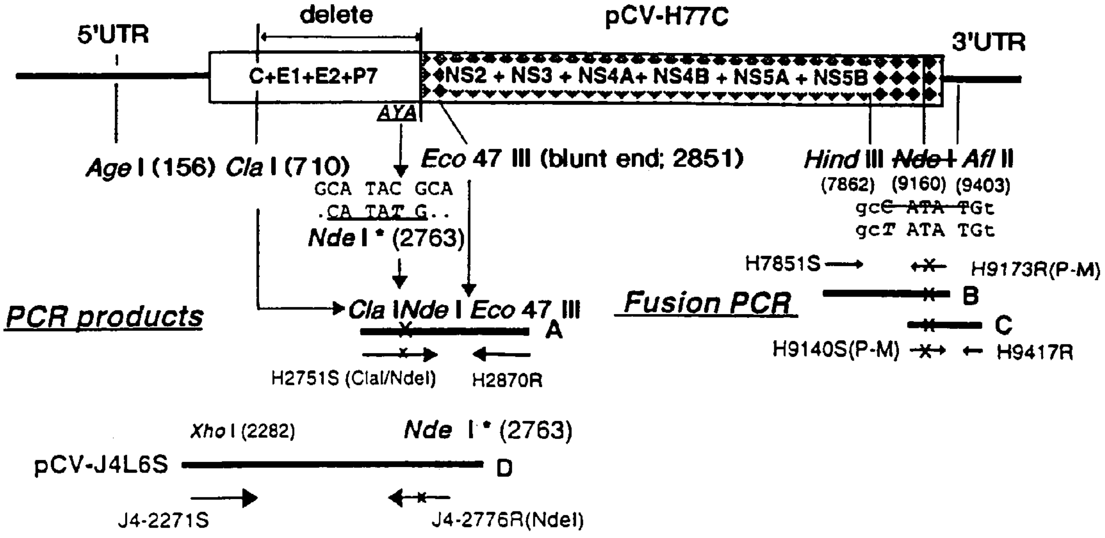

1. Fragment A, B, C and D ; PCR amplification from pCV-H77C or pCV-J4L6S
   - Fragment A ; additional *Cla* I site, artificial *Nde* I site induced by a single mutation (C→T at nt 2765 of H77C) and authentic *Eco*47 III site
   - Fragment B and C ; eliminated Nde I site by a single mutation within the primers (C→T at nt 9158 of H77C), and fusion PCR with both fragments
   - Fragment D ; artificial *Nde* I site induced by 2 point mutations within the primer (T→A at nt 2762 and C→T at nt 2765 of J4L6S)
2. TA cloning of PCR products
3. Sequence analysis
4. Cloning of Fragment A (*Cla* I-*Eco* 47III ) and Fragment B/C (*Hind* III-*Afl* II ) with correct sequence into pCV-H77C
5. Complete sequence analysis of new cassette vector [pH77CV], into which the structural regions of different genotypes can be inserted.
6. Cloning of Fragment-*Age* I/*Xho* I (cut out from pCV-J4L6S) and Fragment D (*Xho* I-*Nde* I) with correct sequence into the new cassette vector ; 3 piece ligation
7. Complete sequence analysis of 1a+1b chimera [pH77CV-J4]
8. *In vitro* transcription (within 24 hours of inoculation)
9. Percutaneous intrahepatic transfection into chimpanzee

FIG. 15 pH77CV-J4 Sequence

| | | | | | |
|---|---|---|---|---|---|
| GCCAGCCCCC | TGATGGGGGC | GACACTCCAC | CATGAATCAC | TCCCCTGTGA | 50 |
| GGAACTACTG | TCTTCACGCA | GAAAGCGTCT | AGCCATGGCG | TTAGTATGAG | 100 |
| TGTCGTGCAG | CCTCCAGGAC | CCCCCCTCCC | GGGAGAGCCA | TAGTGGTCTG | 150 |
| CGGAACCGGT | GAGTACACCG | GAATTGCCAG | GACGACCGGG | TCCTTTCTTG | 200 |
| GATCAACCCG | CTCAATGCCT | GGAGATTTGG | GCGTGCCCCC | GCGAGACTGC | 250 |
| TAGCCGAGTA | GTGTTGGGTC | GCGAAAGGCC | TTGTGGTACT | GCCTGATAGG | 300 |
| GTGCTTGCGA | GTGCCCCGGG | AGGTCTCGTA | GACCGTGCAC | CATGAGCACG | 350 |
| AATCCTAAAC | CTCAAAGAAA | AACCAAACGT | AACACCAACC | GCCGCCCACA | 400 |
| GGACGTCAAG | TTCCCGGGCG | GTGGTCAGAT | CGTTGGTGGA | GTTTACCTGT | 450 |
| TGCCGCGCAG | GGGCCCCAGG | TTGGGTGTGC | GCGCGACTAG | GAAGGCTTCC | 500 |
| GAGCGGTCGC | AACCTCGTGG | AAGGCGACAA | CCTATCCCAA | AGGCTCGCCG | 550 |
| ACCCGAGGGC | AGGGCCTGGG | CTCAGCCCGG | GTACCCTTGG | CCCCTCTATG | 600 |
| GCAATGAGGG | CCTGGGGTGG | GCAGGATGGC | TCCTGTCACC | CCGCGGCTCC | 650 |
| CGGCCTAGTT | GGGGCCCCAC | GGACCCCCGG | CGTAGGTCGC | GTAACTTGGG | 700 |
| TAAGGTCATC | GATACCCTTA | CATGCGGCTT | CGCCGATCTC | ATGGGGTACA | 750 |
| TTCCGCTCGT | CGGCGCCCCC | CTAGGGGGCG | CTGCCAGGGC | CTTGGCACAC | 800 |
| GGTGTCCGGG | TTCTGGAGGA | CGGCGTGAAC | TATGCAACAG | GGAACTTGCC | 850 |
| CGGTTGCTCT | TTCTCTATCT | TCCTCTTGGC | TCTGCTGTCC | TGTTTGACCA | 900 |
| TCCCAGCTTC | CGCTTATGAA | GTGCGCAACG | TGTCCGGGAT | ATACCATGTC | 950 |
| ACGAACGACT | GCTCCAACTC | AAGCATTGTG | TATGAGGCAG | CGGACGTGAT | 1000 |
| CATGCATACT | CCCGGGTGCG | TGCCCTGTGT | TCAGGAGGGT | AACAGCTCCC | 1050 |
| GTTGCTGGGT | AGCGCTCACT | CCCACGCTCG | CGGCCAGGAA | TGCCAGCGTC | 1100 |
| CCCACTACGA | CAATACGACG | CCACGTCGAC | TTGCTCGTTG | GGACGGCTGC | 1150 |
| TTTCTGCTCC | GCTATGTACG | TGGGGGATCT | CTGCGGATCT | ATTTTCCTCG | 1200 |
| TCTCCCAGCT | GTTCACCTTC | TCGCCTCGCC | GGCATGAGAC | AGTGCAGGAC | 1250 |
| TGCAACTGCT | CAATCTATCC | CGGCCATGTA | TCAGGTCACC | GCATGGCTTG | 1300 |
| GGATATGATG | ATGAACTGGT | CACCTACAAC | AGCCCTAGTG | GTGTCGCAGT | 1350 |
| TGCTCCGGAT | CCCACAAGCT | GTCGTGGACA | TGGTGGCGGG | GGCCCACTGG | 1400 |
| GGAGTCCTGG | CGGGCCTTGC | CTACTATTCC | ATGGTAGGGA | ACTGGGCTAA | 1450 |
| GGTTCTGATT | GTGGCGCTAC | TCTTTGCCGG | CGTTGACGGG | GAGACCCACA | 1500 |
| CGACGGGGAG | GGTGGCCGGC | CACACCACCT | CCGGGTTCAC | GTCCCTTTTC | 1550 |
| TCATCTGGGG | CGTCTCAGAA | AATCCAGCTT | GTGAATACCA | ACGGCAGCTG | 1600 |
| GCACATCAAC | AGGACTGCCC | TAAATTGCAA | TGACTCCCTC | CAAACTGGGT | 1650 |
| TCTTTGCCGC | GCTGTTTTAC | GCACACAAGT | TCAACTCGTC | CGGGTGCCCG | 1700 |
| GAGCGCATGG | CCAGCTGCCG | CCCCATTGAC | TGGTTCGCCC | AGGGGTGGGG | 1750 |
| CCCCATCACC | TATACTAAGC | CTAACAGCTC | GGATCAGAGG | CCTTATTGCT | 1800 |

FIG. 16A pH77CV-J4 Sequence

| | | | | | |
|---|---|---|---|---|---|
| GGCATTACGC | GCCTCGACCG | TGTGGTGTCG | TACCCGCGTC | GCAGGTGTGT | 1850 |
| GGTCCAGTGT | ATTGTTTCAC | CCCAAGCCCT | GTTGTGGTGG | GGACCACCGA | 1900 |
| TCGTTCCGGT | GTCCCTACGT | ATAGCTGGGG | GGAGAATGAG | ACAGACGTGA | 1950 |
| TGCTCCTCAA | CAACACGCGT | CCGCCACAAG | GCAACTGGTT | CGGCTGTACA | 2000 |
| TGGATGAATA | GTACTGGGTT | CACTAAGACG | TGCGGAGGTC | CCCCGTGTAA | 2050 |
| CATCGGGGGG | GTCGGTAACC | GCACCTTGAT | CTGCCCCACG | GACTGCTTCC | 2100 |
| GGAAGCACCC | CGAGGCTACT | TACACAAAAT | GTGGCTCGGG | GCCCTGGTTG | 2150 |
| ACACCTAGGT | GCCTAGTAGA | CTACCCATAC | AGGCTTTGGC | ACTACCCCTG | 2200 |
| CACTCTCAAT | TTTTCCATCT | TTAAGGTTAG | GATGTATGTG | GGGGGCGTGG | 2250 |
| AGCACAGGCT | CAATGCCGCA | TGCAATTGGA | CTCGAGGAGA | GCGCTGTAAC | 2300 |
| TTGGAGGACA | GGGATAGGTC | AGAACTCAGC | CCGCTGCTGC | TGTCTACAAC | 2350 |
| AGAGTGGCAG | ATACTGCCCT | GTGCTTTCAC | CACCCTACCG | GCTTTATCCA | 2400 |
| CTGGTTTGAT | CCATCTCCAT | CAGAACATCG | TGGACGTGCA | ATACCTGTAC | 2450 |
| GGTGTAGGGT | CAGCGTTTGT | CTCCTTTGCA | ATCAAATGGG | AGTACATCCT | 2500 |
| GTTGCTTTTC | CTTCTCCTGG | CAGACGCGCG | CGTGTGTGCC | TGCTTGTGGA | 2550 |
| TGATGCTGCT | GATAGCCCAG | GCTGAGGCCG | CCTTAGAGAA | CTTGGTGGTC | 2600 |
| CTCAATGCGG | CGTCCGTGGC | CGGAGCGCAT | GGTATTCTCT | CCTTTCTTGT | 2650 |
| GTTCTTCTGC | GCCGCCTGGT | ACATTAAGGG | CAGGCTGGCT | CCTGGGGCGG | 2700 |
| CGTATGCTTT | TTATGGCGTA | TGGCCGCTGC | TCCTGCTCCT | ACTGGCGTTA | 2750 |
| CCACCACGAG | CATATGCACT | GGACACGGAG | GTGGCCGCGT | CGTGTGGCGG | 2800 |
| CGTTGTTCTT | GTCGGGTTAA | TGGCGCTGAC | TCTGTCGCCA | TATTACAAGC | 2850 |
| GCTATATCAG | CTGGTGCATG | TGGTGGCTTC | AGTATTTTCT | GACCAGAGTA | 2900 |
| GAAGCGCAAC | TGCACGTGTG | GGTTCCCCCC | CTCAACGTCC | GGGGGGGGCG | 2950 |
| CGATGCCGTC | ATCTTACTCA | TGTGTGTAGT | ACACCCGACC | CTGGTATTTG | 3000 |
| ACATCACCAA | ACTACTCCTG | GCCATCTTCG | GACCCCTTTG | GATTCTTCAA | 3050 |
| GCCAGTTTGC | TTAAAGTCCC | CTACTTCGTG | CGCGTTCAAG | GCCTTCTCCG | 3100 |
| GATCTGCGCG | CTAGCGCGGA | AGATAGCCGG | AGGTCATTAC | GTGCAAATGG | 3150 |
| CCATCATCAA | GTTAGGGGCG | CTTACTGGCA | CCTATGTGTA | TAACCATCTC | 3200 |
| ACCCCTCTTC | GAGACTGGGC | GCACAACGGC | CTGCGAGATC | TGGCCGTGGC | 3250 |
| TGTGGAACCA | GTCGTCTTCT | CCCGAATGGA | GACCAAGCTC | ATCACGTGGG | 3300 |
| GGGCAGATAC | CGCCGCGTGC | GGTGACATCA | TCAACGGCTT | GCCCGTCTCT | 3350 |
| GCCCGTAGGG | GCCAGGAGAT | ACTGCTTGGG | CCAGCCGACG | GAATGGTCTC | 3400 |
| CAAGGGGTGG | AGGTTGCTGG | CGCCCATCAC | GGCGTACGCC | CAGCAGACGA | 3450 |
| GAGGCCTCCT | AGGGTGTATA | ATCACCAGCC | TGACTGGCCG | GGACAAAAAC | 3500 |
| CAAGTGGAGG | GTGAGGTCCA | GATCGTGTCA | ACTGCTACCC | AAACCTTCCT | 3550 |
| GGCAACGTGC | ATCAATGGGG | TATGCTGGAC | TGTCTACCAC | GGGGCCGGAA | 3600 |

FIG. 16B pH77CV-J4 Sequence

```
CGAGGACCAT CGCATCACCC AAGGGTCCTG TCATCCAGAT GTATACCAAT   3650
GTGGACCAAG ACCTTGTGGG CTGGCCCGCT CCTCAAGGTT CCCGCTCATT   3700
GACACCCTGT ACCTGCGGCT CCTCGGACCT TTACCTGGTC ACGAGGCACG   3750
CCGATGTCAT TCCCGTGCGC CGGCGAGGTG ATAGCAGGGG TAGCCTGCTT   3800

TCGCCCCGGC CCATTTCCTA CTTGAAAGGC TCCTCGGGGG GTCCGCTGTT   3850
GTGCCCCGCG GGACACGCCG TGGGCCTATT CAGGGCCGCG GTGTGCACCC   3900
GTGGAGTGGC TAAAGCGGTG GACTTTATCC CTGTGGAGAA CCTAGGGACA   3950
ACCATGAGAT CCCCGGTGTT CACGGACAAC TCCTCTCCAC CAGCAGTGCC   4000
CCAGAGCTTC CAGGTGGCCC ACCTGCATGC TCCCACCGGC AGCGGTAAGA   4050
GCACCAAGGT CCCGGCTGCG TACGCAGCCC AGGGCTACAA GGTGTTGGTG   4100
CTCAACCCCT CTGTTGCTGC AACGCTGGGC TTTGGTGCTT ACATGTCCAA   4150
GGCCCATGGG GTTGATCCTA ATATCAGGAC CGGGGTGAGA ACAATTACCA   4200
CTGGCAGCCC CATCACGTAC TCCACCTACG GCAAGTTCCT TGCCGACGGC   4250
GGGTGCTCAG GAGGTGCTTA TGACATAATA ATTTGTGACG AGTGCCACTC   4300
CACGGATGCC ACATCCATCT TGGGCATCGG CACTGTCCTT GACCAAGCAG   4350
AGACTGCGGG GGCGAGACTG GTTGTGCTCG CCACTGCTAC CCCTCCGGGC   4400
TCCGTCACTG TGTCCCATCC TAACATCGAG GAGGTTGCTC TGTCCACCAC   4450
CGGAGAGATC CCCTTTTACG GCAAGGCTAT CCCCCTCGAG GTGATCAAGG   4500
GGGGAAGACA TCTCATCTTC TGCCACTCAA AGAAGAAGTG CGACGAGCTC   4550
GCCGCGAAGC TGGTCGCATT GGGCATCAAT GCCGTGGCCT ACTACCGCGG   4600
TCTTGACGTG TCTGTCATCC CGACCAGCGG CGATGTTGTC GTCGTGTCGA   4650
CCGATGCTCT CATGACTGGC TTTACCGGCG ACTTCGACTC TGTGATAGAC   4700
TGCAACACGT GTGTCACTCA GACAGTCGAT TTCAGCCTTG ACCCTACCTT   4750
TACCATTGAG ACAACCACGC TCCCCCAGGA TGCTGTCTCC AGGACTCAAC   4800
GCCGGGGCAG GACTGGCAGG GGGAAGCCAG GCATCTATAG ATTTGTGGCA   4850
CCGGGGGAGC GCCCCTCCGG CATGTTCGAC TCGTCCGTCC TCTGTGAGTG   4900
CTATGACGCG GGCTGTGCTT GGTATGAGCT CACGCCCGCC GAGACTACAG   4950
TTAGGCTACG AGCGTACATG AACACCCCGG GGCTTCCCGT GTGCCAGGAC   5000
CATCTTGAAT TTTGGGAGGG CGTCTTTACG GGCCTCACTC ATATAGATGC   5050
CCACTTTTTA TCCCAGACAA AGCAGAGTGG GGAGAACTTT CCTTACCTGG   5100
TAGCGTACCA AGCCACCGTG TGCGCTAGGG CTCAAGCCCC TCCCCCATCG   5150
TGGGACCAGA TGTGGAAGTG TTTGATCCGC CTTAAACCCA CCCTCCATGG   5200
GCCAACACCC CTGCTATACA GACTGGGCGC TGTTCAGAAT GAAGTCACCC   5250
TGACGCACCC AATCACCAAA TACATCATGA CATGCATGTC GGCCGACCTG   5300
GAGGTCGTCA CGAGCACCTG GGTGCTCGTT GGCGGCGTCC TGGCTGCTCT   5350
GGCCGCGTAT TGCCTGTCAA CAGGCTGCGT GGTCATAGTG GGCAGGATCG   5400
```

FIG. 16C pH77CV-J4 Sequence

TCTTGTCCGG GAAGCCGGCA ATTATACCTG ACAGGGAGGT TCTCTACCAG 5450
GAGTTCGATG AGATGGAAGA GTGCTCTCAG CACTTACCGT ACATCGAGCA 5500
AGGGATGATG CTCGCTGAGC AGTTCAAGCA GAAGGCCCTC GGCCTCCTGC 5550
AGACCGCGTC CCGCCATGCA GAGGTTATCA CCCCTGCTGT CCAGACCAAC 5600
TGGCAGAAAC TCGAGGTCTT TTGGGCGAAG CACATGTGGA ATTTCATCAG 5650
TGGGATACAA TACTTGGCGG GCCTGTCAAC GCTGCCTGGT AACCCCGCCA 5700
TTGCTTCATT GATGGCTTTT ACAGCTGCCG TCACCAGCCC ACTAACCACT 5750
GGCCAAACCC TCCTCTTCAA CATATTGGGG GGGTGGGTGG CTGCCCAGCT 5800
CGCCGCCCCC GGTGCCGCTA CTGCCTTTGT GGGTGCTGGC CTAGCTGGCG 5850
CCGCCATCGG CAGCGTTGGA CTGGGGAAGG TCCTCGTGGA CATTCTTGCA 5900
GGGTATGGCG CGGGCGTGGC GGGAGCTCTT GTAGCATTCA AGATCATGAG 5950
CGGTGAGGTC CCCTCCACGG AGGACCTGGT CAATCTGCTG CCCGCCATCC 6000
TCTCGCCTGG AGCCCTTGTA GTCGGTGTGG TCTGCGCAGC AATACTGCGC 6050
CGGCACGTTG GCCCGGGCGA GGGGGCAGTG CAATGGATGA ACCGGCTAAT 6100
AGCCTTCGCC TCCCGGGGGA ACCATGTTTC CCCCACGCAC TACGTGCCGG 6150
AGAGCGATGC AGCCGCCCGC GTCACTGCCA TACTCAGCAG CCTCACTGTA 6200
ACCCAGCTCC TGAGGCGACT GCATCAGTGG ATAAGCTCGG AGTGTACCAC 6250
TCCATGCTCC GGTTCCTGGC TAAGGGACAT CTGGGACTGG ATATGCGAGG 6300
TGCTGAGCGA CTTTAAGACC TGGCTGAAAG CCAAGCTCAT GCCACAACTG 6350
CCTGGGATTC CCTTTGTGTC CTGCCAGCGC GGGTATAGGG GGGTCTGGCG 6400
AGGAGACGGC ATTATGCACA CTCGCTGCCA CTGTGGAGCT GAGATCACTG 6450
GACATGTCAA AAACGGGACG ATGAGGATCG TCGGTCCTAG GACCTGCAGG 6500
AACATGTGGA GTGGGACGTT CCCCATTAAC GCCTACACCA CGGGCCCCTG 6550
TACTCCCCTT CCTGCGCCGA ACTATAAGTT CGCGCTGTGG AGGGTGTCTG 6600
CAGAGGAATA CGTGGAGATA AGGCGGGTGG GGGACTTCCA CTACGTATCG 6650
GGTATGACTA CTGACAATCT TAAATGCCCG TGCCAGATCC CATCGCCCGA 6700
ATTTTTCACA GAATTGGACG GGGTGCGCCT ACACAGGTTT GCGCCCCCTT 6750
GCAAGCCCTT GCTGCGGGAG GAGGTATCAT TCAGAGTAGG ACTCCACGAG 6800
TACCCGGTGG GGTCGCAATT ACCTTGCGAG CCCGAACCGG ACGTAGCCGT 6850
GTTGACGTCC ATGCTCACTG ATCCCTCCCA TATAACAGCA GAGGCGGCCG 6900
GGAGAAGGTT GGCGAGAGGG TCACCCCCTT CTATGGCCAG CTCCTCGGCT 6950
AGCCAGCTGT CCGCTCCATC TCTCAAGGCA ACTTGCACCG CCAACCATGA 7000
CTCCCCTGAC GCCGAGCTCA TAGAGGCTAA CCTCCTGTGG AGGCAGGAGA 7050
TGGGCGGCAA CATCACCAGG GTTGAGTCAG AGAACAAAGT GGTGATTCTG 7100
GACTCCTTCG ATCCGCTTGT GGCAGAGGAG GATGAGCGGG AGGTCTCCGT 7150
ACCTGCAGAA ATTCTGCGGA AGTCTCGGAG ATTCGCCCGG GCCCTGCCCG 7200

FIG. 16D pH77CV-J4 Sequence

```
TCTGGGCGCG GCCGGACTAC AACCCCCCGC TAGTAGAGAC GTGGAAAAAG   7250
CCTGACTACG AACCACCTGT GGTCCATGGC TGCCCGCTAC CACCTCCACG   7300
GTCCCCTCCT GTGCCTCCGC CTCGGAAAAA GCGTACGGTG GTCCTCACCG   7350
AATCAACCCT ATCTACTGCC TTGGCCGAGC TTGCCACCAA AAGTTTTGGC   7400
AGCTCCTCAA CTTCCGGCAT TACGGGCGAC AATACGACAA CATCCTCTGA   7450
GCCCGCCCCT TCTGGCTGCC CCCCCGACTC CGACGTTGAG TCCTATTCTT   7500
CCATGCCCCC CCTGGAGGGG GAGCCTGGGG ATCCGGATCT CAGCGACGGG   7550
TCATGGTCGA CGGTCAGTAG TGGGGCCGAC ACGGAAGATG TCGTGTGCTG   7600
CTCAATGTCT TATTCCTGGA CAGGCGCACT CGTCACCCCG TGCGCTGCGG   7650
AAGAACAAAA ACTGCCCATC AACGCACTGA GCAACTCGTT GCTACGCCAT   7700
CACAATCTGG TGTATTCCAC CACTTCACGC AGTGCTTGCC AAAGGCAGAA   7750
GAAAGTCACA TTTGACAGAC TGCAAGTTCT GGACAGCCAT TACCAGGACG   7800
TGCTCAAGGA GGTCAAAGCA GCGGCGTCAA AAGTGAAGGC TAACTTGCTA   7850
TCCGTAGAGG AAGCTTGCAG CCTGACGCCC CCACATTCAG CCAAATCCAA   7900
GTTTGGCTAT GGGGCAAAAG ACGTCCGTTG CCATGCCAGA AAGGCCGTAG   7950
CCCACATCAA CTCCGTGTGG AAAGACCTTC TGGAAGACAG TGTAACACCA   8000
ATAGACACTA CCATCATGGC CAAGAACGAG GTTTTCTGCG TTCAGCCTGA   8050
GAAGGGGGGT CGTAAGCCAG CTCGTCTCAT CGTGTTCCCC GACCTGGGCG   8100
TGCGCGTGTG CGAGAAGATG GCCCTGTACG ACGTGGTTAG CAAGCTCCCC   8150
CTGGCCGTGA TGGGAAGCTC CTACGGATTC CAATACTCAC CAGGACAGCG   8200
GGTTGAATTC CTCGTGCAAG CGTGGAAGTC CAAGAAGACC CCGATGGGGT   8250
TCTCGTATGA TACCCGCTGT TTTGACTCCA CAGTCACTGA GAGCGACATC   8300
CGTACGGAGG AGGCAATTTA CCAATGTTGT GACCTGGACC CCCAAGCCCG   8350
CGTGGCCATC AAGTCCCTCA CTGAGAGGCT TTATGTTGGG GGCCCTCTTA   8400
CCAATTCAAG GGGGGAAAAC TGCGGCTACC GCAGGTGCCG CGCGAGCGGC   8450
GTACTGACAA CTAGCTGTGG TAACACCCTC ACTTGCTACA TCAAGGCCCG   8500
GGCAGCCTGT CGAGCCGCAG GGCTCCAGGA CTGCACCATG CTCGTGTGTG   8550
GCGACGACTT AGTCGTTATC TGTGAAAGTG CGGGGGTCCA GGAGGACGCG   8600
GCGAGCCTGA GAGCCTTCAC GGAGGCTATG ACCAGGTACT CCGCCCCCCC   8650
CGGGGACCCC CCACAACCAG AATACGACTT GGAGCTTATA ACATCATGCT   8700
CCTCCAACGT GTCAGTCGCC CACGACGGCG CTGGAAAGAG GGTCTACTAC   8750
CTTACCCGTG ACCCTACAAC CCCCCTCGCG AGAGCCGCGT GGGAGACAGC   8800
AAGACACACT CCAGTCAATT CCTGGCTAGG CAACATAATC ATGTTTGCCC   8850
CCACACTGTG GGCGAGGATG ATACTGATGA CCCATTTCTT TAGCGTCCTC   8900
ATAGCCAGGG ATCAGCTTGA ACAGGCTCTT AACTGTGAGA TCTACGGAGC   8950
CTGCTACTCC ATAGAACCAC TGGATCTACC TCCAATCATT CAAAGACTCC   9000
```

FIG. 16E pH77CV-J4 Sequence

```
ATGGCCTCAG CGCATTTTCA CTCCACAGTT ACTCTCCAGG TGAAATCAAT    9050
AGGGTGGCCG CATGCCTCAG AAAACTTGGG GTCCCGCCCT TGCGAGCTTG    9100
GAGACACCGG GCCCGGAGCG TCCGCGCTAG GCTTCTGTCC AGAGGAGGCA    9150
GGGCTGCTAT ATGTGGCAAG TACCTCTTCA ACTGGGCAGT AAGAACAAAG    9200
CTCAAACTCA CTCCAATAGC GGCCGCTGGC CGGCTGGACT TGTCCGGTTG    9250
GTTCACGGCT GGCTACAGCG GGGGAGACAT TTATCACAGC GTGTCTCATG    9300
CCCGGCCCCG CTGGTTCTGG TTTTGCCTAC TCCTGCTCGC TGCAGGGGTA    9350
GGCATCTACC TCCTCCCCAA CCGATGAAGG TTGGGGTAAA CACTCCGGCC    9400
TCTTAAGCCA TTTCCTGTTT TTTTTTTTTT TTTTTTTTTT TTTTTCTTTT    9450
TTTTTTTCTT TCCTTTCCTT CTTTTTTTCC TTTCTTTTTC CCTTCTTTAA    9500
TGGTGGCTCC ATCTTAGCCC TAGTCACGGC TAGCTGTGAA AGGTCCGTGA    9550
GCCGCATGAC TGCAGAGAGT GCTGATACTG GCCTCTCTGC AGATCATGT     9599
```

FIG. 16F

H77CV-J4aa Sequence

| 10 | 20 | 30 | 40 | 50 | |
|---|---|---|---|---|---|
| 1234567890 | 1234567890 | 1234567890 | 1234567890 | 1234567890 | |
| MSTNPKPQRK | TKRNTNRRPQ | DVKFPGGGQI | VGGVYLLPRR | GPRLGVRATR | 50 |
| KASERSQPRG | RRQPIPKARR | PEGRAWAQPG | YPWPLYGNEG | LGWAGWLLSP | 100 |
| RGSRPSWGPT | DPRRRSRNLG | KVIDTLTCGF | ADLMGYIPLV | GAPLGGAARA | 150 |
| LAHGVRVLED | GVNYATGNLP | GCSFSIFLLA | LLSCLTIPAS | AYEVRNVSGI | 200 |
| YHVTNDCSNS | SIVYEAADVI | MHTPGCVPCV | QEGNSSRCWV | ALTPTLAARN | 250 |
| ASVPTTTIRR | HVDLLVGTAA | FCSAMYVGDL | CGSIFLVSQL | FTFSPRRHET | 300 |
| VQDCNCSIYP | GHVSGHRMAW | DMMMNWSPTT | ALVVSQLLRI | PQAVVDMVAG | 350 |
| AHWGVLAGLA | YYSMVGNWAK | VLIVALLFAG | VDGETHTTGR | VAGHTTSGFT | 400 |
| SLFSSGASQK | IQLVNTNGSW | HINRTALNCN | DSLQTGFFAA | LFYAHKFNSS | 450 |
| GCPERMASCR | PIDWFAQGWG | PITYTKPNSS | DQRPYCWHYA | PRPCGVVPAS | 500 |
| QVCGPVYCFT | PSPVVVGTTD | RSGVPTYSWG | ENETDVMLLN | NTRPPQGNWF | 550 |
| GCTWMNSTGF | TKTCGGPPCN | IGGVGNRTLI | CPTDCFRKHP | EATYTKCGSG | 600 |
| PWLTPRCLVD | YPYRLWHYPC | TLNFSIFKVR | MYVGGVEHRL | NAACNWTRGE | 650 |
| RCNLEDRDRS | ELSPLLLSTT | EWQILPCAFT | TLPALSTGLI | HLHQNIVDVQ | 700 |
| YLYGVGSAFV | SFAIKWEYIL | LLFLLLADAR | VCACLWMMLL | IAQAEAALEN | 750 |
| LVVLNAASVA | GAHGILSFLV | FFCAAWYIKG | RLAPGAAYAF | YGVWPLLLLL | 800 |
| LALPPRAYAL | DTEVAASCGG | VVLVGLMALT | LSPYYKRYIS | WCMWWLQYFL | 850 |
| TRVEAQLHVW | VPPLNVRGGR | DAVILLMCVV | HPTLVFDITK | LLLAIFGPLW | 900 |
| ILQASLLKVP | YFVRVQGLLR | ICALARKIAG | GHYVQMAIIK | LGALTGTYVY | 950 |
| NHLTPLRDWA | HNGLRDLAVA | VEPVVFSRME | TKLITWGADT | AACGDIINGL | 1000 |
| PVSARRGQEI | LLGPADGMVS | KGWRLLAPIT | AYAQQTRGLL | GCIITSLTGR | 1050 |
| DKNQVEGEVQ | IVSTATQTFL | ATCINGVCWT | VYHGAGTRTI | ASPKGPVIQM | 1100 |
| YTNVDQDLVG | WPAPQGSRSL | TPCTCGSSDL | YLVTRHADVI | PVRRRGDSRG | 1150 |
| SLLSPRPISY | LKGSSGGPLL | CPAGHAVGLF | RAAVCTRGVA | KAVDFIPVEN | 1200 |
| LGTTMRSPVF | TDNSSPPAVP | QSFQVAHLHA | PTGSGKSTKV | PAAYAAQGYK | 1250 |
| VLVLNPSVAA | TLGFGAYMSK | AHGVDPNIRT | GVRTITTGSP | ITYSTYGKFL | 1300 |
| ADGGCSGGAY | DIIICDECHS | TDATSILGIG | TVLDQAETAG | ARLVVLATAT | 1350 |
| PPGSVTVSHP | NIEEVALSTT | GEIPFYGKAI | PLEVIKGGRH | LIFCHSKKKC | 1400 |
| DELAAKLVAL | GINAVAYYRG | LDVSVIPTSG | DVVVVSTDAL | MTGFTGDFDS | 1450 |
| VIDCNTCVTQ | TVDFSLDPTF | TIETTTLPQD | AVSRTQRRGR | TGRGKPGIYR | 1500 |
| FVAPGERPSG | MFDSSVLCEC | YDAGCAWYEL | TPAETTVRLR | AYMNTPGLPV | 1550 |
| CQDHLEFWEG | VFTGLTHIDA | HFLSQTKQSG | ENFPYLVAYQ | ATVCARAQAP | 1600 |
| PPSWDQMWKC | LIRLKPTLHG | PTPLLYRLGA | VQNEVTLTHP | ITKYIMTCMS | 1650 |
| ADLEVVTSTW | VLVGGVLAAL | AAYCLSTGCV | VIVGRIVLSG | KPAIIPDREV | 1700 |
| LYQEFDEMEE | CSQHLPYIEQ | GMMLAEQFKQ | KALGLLQTAS | RHAEVTTPAV | 1750 |
| QTNWQKLEVF | WAKHMWNFIS | GIQYLAGLST | LPGNPAIASL | MAFTAAVTSP | 1800 |
| LTTGQTLLFN | ILGGWVAAQL | AAPGAATAFV | GAGLAGAAIG | SVGLGKVLVD | 1850 |
| ILAGYGAGVA | GALVAFKIMS | GEVPSTEDLV | NLLPAILSPG | ALVVGVVCAA | 1900 |

FIG. 16G

H77CV-J4aa Sequence

| 10<br>1234567890 | 20<br>1234567890 | 30<br>1234567890 | 40<br>1234567890 | 50<br>1234567890 | |
|---|---|---|---|---|---|
| ILRRHVGPGE | GAVQWMNRLI | AFASRGNHVS | PTHYVPESDA | AARVTAILSS | 1950 |
| LTVTQLLRRL | HQWISSECTT | PCSGSWLRDI | WDWICEVLSD | FKTWLKAKLM | 2000 |
| PQLPGIPFVS | CQRGYRGVWR | GDGIMHTRCH | CGAEITGHVK | NGTMRIVGPR | 2050 |
| TCRNMWSGTF | PINAYTTGPC | TPLPAPNYKF | ALWRVSAEEY | VEIRRVGDFH | 2100 |
| YVSGMTTDNL | KCPCQIPSPE | FFTELDGVRL | HRFAPPCKPL | LREEVSFRVG | 2150 |
| LHEYPVGSQL | PCEPEPDVAV | LTSMLTDPSH | ITAEAAGRRL | ARGSPPSMAS | 2200 |
| SSASQLSAPS | LKATCTANHD | SPDAELIEAN | LLWRQEMGGN | ITRVESENKV | 2250 |
| VILDSFDPLV | AEEDEREVSV | PAEILRKSRR | FARALPVWAR | PDYNPPLVET | 2300 |
| WKKPDYEPPV | VHGCPLPPPR | SPPVPPPRKK | RTVVLTESTL | STALAELATK | 2350 |
| SFGSSSTSGI | TGDNTTTSSE | PAPSGCPPDS | DVESYSSMPP | LEGEPGDPDL | 2400 |
| SDGSWSTVSS | GADTEDVVCC | SMSYSWTGAL | VTPCAAEEQK | LPINALSNSL | 2450 |
| LRHHNLVYST | TSRSACQRQK | KVTFDRLQVL | DSHYQDVLKE | VKAAASKVKA | 2500 |
| NLLSVEEACS | LTPPHSAKSK | FGYGAKDVRC | HARKAVAHIN | SVWKDLLEDS | 2550 |
| VTPIDTTIMA | KNEVFCVQPE | KGGRKPARLI | VFPDLGVRVC | EKMALYDVVS | 2600 |
| KLPLAVMGSS | YGFQYSPGQR | VEFLVQAWKS | KKTPMGFSYD | TRCFDSTVTE | 2650 |
| SDIRTEEAIY | QCCDLDPQAR | VAIKSLTERL | YVGGPLTNSR | GENCGYRRCR | 2700 |
| ASGVLTTSCG | NTLTCYIKAR | AACRAAGLQD | CTMLVCGDDL | VVICESAGVQ | 2750 |
| EDAASLRAFT | EAMTRYSAPP | GDPPQPEYDL | ELITSCSSNV | SVAHDGAGKR | 2800 |
| VYYLTRDPTT | PLARAAWETA | RHTPVNSWLG | NIIMFAPTLW | ARMILMTHFF | 2850 |
| SVLIARDQLE | QALNCEIYGA | CYSIEPLDLP | PIIQRLHGLS | AFSLHSYSPG | 2900 |
| EINRVAACLR | KLGVPPLRAW | RHRARSVRAR | LLSRGGRAAI | CGKYLFNWAV | 2950 |
| RTKLKLTPIA | AAGRLDLSGW | FTAGYSGGDI | YHSVSHARPR | WFWFCLLLLA | 3000 |
| AGVGIYLLPN | R | | | | 3011 |

FIG. 16H

#1a. 3' Deletion mutants of pCV-H77C

Sequence of 3' untranslated region of pCV-H77C

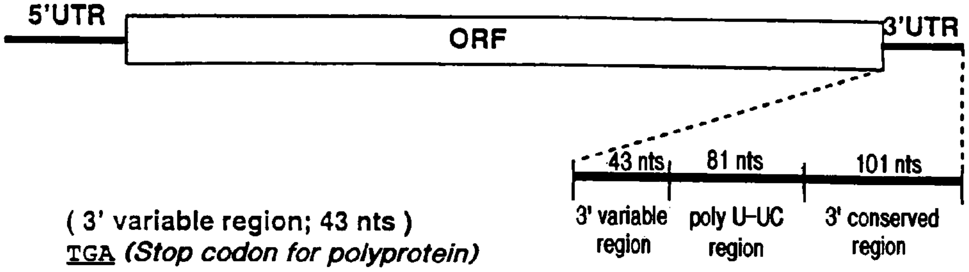

( 3' variable region; 43 nts )
TGA *(Stop codon for polyprotein)*

AGGTTGGGGT AAACACTCCG GCCTCTTAAG CCATTTCCTG
*Afl II*

(poly U-UC region; 81 nts)
TTTTTTTTTT TTTTTTTTTT TTTTTTTTCT TTTTTTTTTT CTTTCCTTTC
CTTCTTTTTT TCCTTTCTTT TTCCCTTCTT T (3' conserved region; 101 nts)
AATGGTGGCT CCATCTTAGC CCTAGTCACG GCTAGCTGTG AAAGGTCCGT
GAGCCGCATG ACTGCAGAGA GTGCTGATAC TGGCCTCTCT GCAGATCATG
T

#1a -1. pCV-H77C(-98X) ; 3' 98 nucleotides removed from pCV-H77C

TGAAGGTTGG GGTAAACACT CCGGCCTCTT AAGCCATTTC CTGTTTTTTT
TTTTTTTTTT TTTTTTTTTT TCTTTTTTTT TTTCTTTCCT TTCCTTCTTT
TTTTCCTTTC TTTTTCCCTT CTTTAAT

#1a -2. pCV-H77C(-42X) ; 3' 42 nucleotides removed from pCV-H77C

TGAAGGTTGG GGTAAACACT CCGGCCTCTT AAGCCATTTC CTGTTTTTTT
TTTTTTTTTT TTTTTTTTTT TCTTTTTTTT TTTCTTTCCT TTCCTTCTTT
TTTTCCTTTC TTTTTCCCTT CTTTAATGGT GGCTCCATCT TAGCCCTAGT
CACGGCTAGC TGTGAAAGGT CCGTGAGCCG CAT

#1a -3. pCV-H77C(X-52) ; All of the 3' UTR sequence, except 3' 49 nucleotides, removed from pCV-H77C

TGAGCCGCAT GACTGCAGAG AGTGCTGATA CTGGCCTCTC TGCAGATCAT
GT

FIG. 17A

#1a -4. pCV-H77C(X) ; All of the 3' UTR sequence, except 3' 101 nucleotides, removed from pCV-H77C TGAAATGGTG GCTCCATCTT AGCCCTAGTC ACGGCTAGCT GTGAAAGGTC
CGTGAGCCGC ATGACTGCAG AGAGTGCTGA TACTGGCCTC TCTGCAGATC
ATGT

#1a -5. pCV-H77C(+49X) ; The proximal 49 nucleotides of the 3' conserved region ( 98 nucleotides ; AAT not included) removed from pCV-H77C TGAAGGTTGG GGTAAACACT CCGGCCTCTT AAGCCATTTC CTGTTTTTTT
TTTTTTTTTT TTTTTTTTTT TCTTTTTTTT TTTCTTTCCT TTCCTTCTTT
TTTTCCTTTC TTTTTCCCTT CTTTAATGCC GCATGACTGC AGAGAGTGCT
GATACTGGCC TCTCTGCAGA TCATGT

#1a -6. pCV-H77C(VR-24) ; First 24 nucleotides of the 3' variable region removed from pCV-H77C TGACTTAAGC CATTTCCTGT TTTTTTTTTT TTTTTTTTTT TTTTTTTCTT
TTTTTTTTTC TTTCCTTTCC TTCTTTTTTT CCTTTCTTTT TCCCTTCTTT
AATGGTGGCT CCATCTTAGC CCTAGTCACG GCTAGCTGTG AAAGGTCCGT
GAGCCGCATG ACTGCAGAGA GTGCTGATAC TGGCCTCTCT GCAGATCATG
T

#1a -7. pCV-H77C(-U/UC) ; Poly U-UC region removed from pCV-H77C

TGAAGGTTGG GGTAAACACT CCGGCCTCTT AAGCCATTTC CTGAATGGTG
GCTCCATCTT AGCCCTAGTC ACGGCTAGCT GTGAAAGGTC CGTGAGCCGC
ATGACTGCAG AGAGTGCTGA TACTGGCCTC TCTGCAGATC ATGT

FIG. 17B

#1b. Strategy of 3' Deletion mutants

#1b -1. pCV-H77C(-98X)

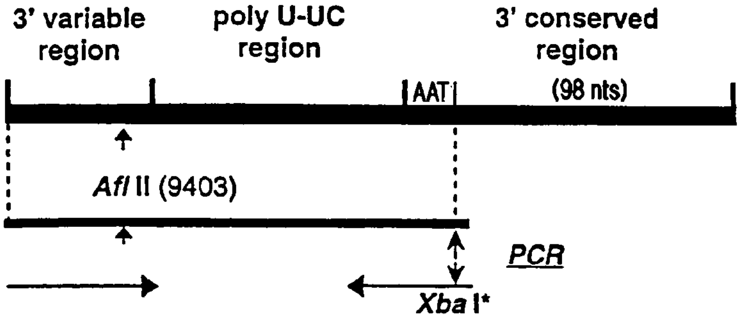

1. PCR Amplification
2. Purification of PCR products
3. Digestion with *Afl* II and *Xba* I
4. Cloning of *Afl* II /*Xba* I fragment into pCV-H77C
5. Complete sequence analysis
6. in vitro transcription (within 24 hours of inoculation)
7. Percutaneous intrahepatic transfection into chimpanzee ; 11/26/97 and 12/17/97
8. Result : Negative ( No replication)

#1b -2. pCV-H77C(-42X)

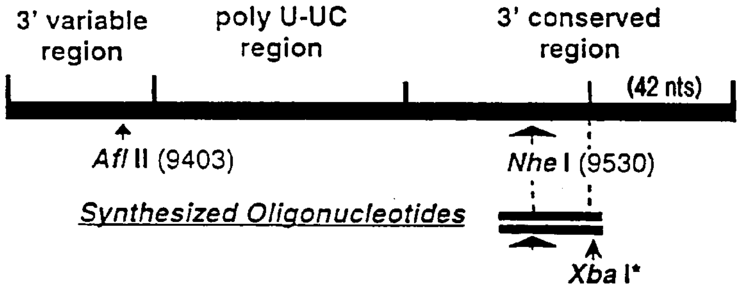

1. Synthesis of oligonucleotides ( sense and anti-sense )
2. Hybridization of oligonucleotides
3. Digestion with *Nhe* I and *Xba* I
4. Cloning of *Nhe* I /*Xba* I fragment into pG9-KL26 (3' UTR of H77C)
5. Sequence analysis
6. Cloning of 3' UTR ( -42X ) [*Afl* II /*Xba* I fragment] into pCV-H77C
7. Complete sequence analysis
8. in vitro transcription (within 24 hours of inoculation)
9. Percutaneous intrahepatic transfection into chimpanzee (Schedule; 1/22/98, 2/5/98 )

FIG. 17C

#1b -3. pCV-H77C(X-52)

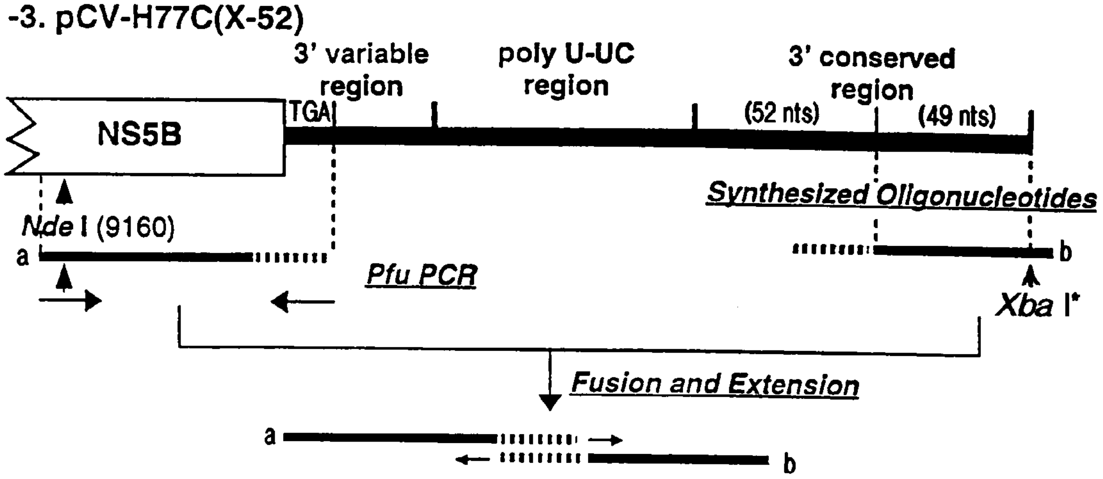

1. Fragment a ; *Pfu* PCR amplification and purification
2. Fragment b ; Synthesized oligonucleotides (anti-sense)
3. Fusion and extension
4. TA cloning
5. Sequence analysis
6. Cloning *Nde* I-*Xba* I fragment with correct sequence into pCV-H77C
7. Complete sequence analysis
8. *In vitro* transcription (within 24 hours of inoculation)
9. Percutaneous intrahepatic transfection into chimpanzee

FIG. 17D

#1b -4. pCV-H77C(X)

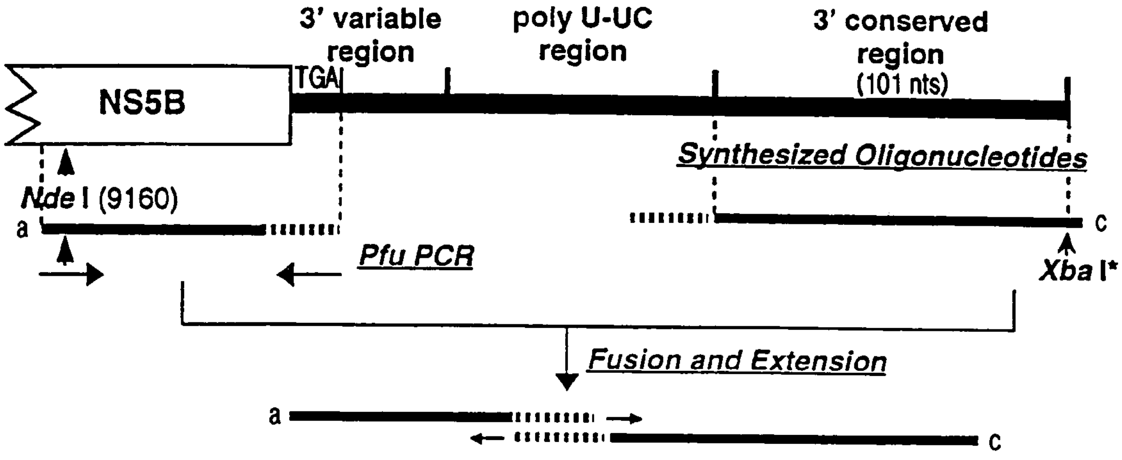

1. Fragment a ; *Pfu* PCR amplification and purification
2. Fragment c ; Synthesized oligonucleotides (anti-sense)
3. Fusion and extension
4. TA cloning
5. Sequence analysis
6. Cloning *Nde* I-*Xba* I fragment with correct sequence into pCV-H77C
7. Complete sequence analysis
8. *In vitro* transcription (within 24 hours of inoculation)
9. Percutaneous intrahepatic transfection into chimpanzee

FIG. 17E

#1b -5. pCV-H77C(+49X)

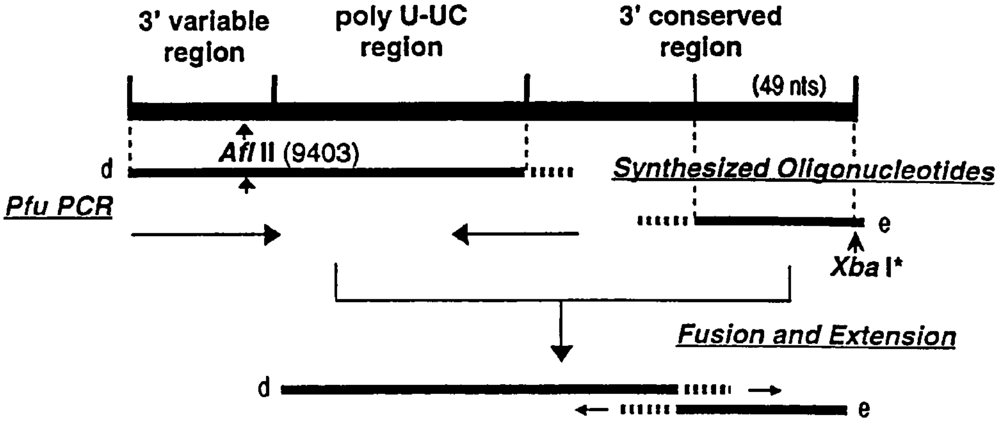

1. Fragment d ; *Pfu* PCR amplification and purification
2. Fragment e ; Synthesized oligonucleotides (anti-sense)
3. Fusion and extension
4. TA cloning
5. Sequence analysis
6. Cloning *Afl* II-*Xba* I fragment with correct sequence into pCV-H77C
7. Complete sequence analysis
8. *In vitro* transcription (within 24 hours of inoculation)
9. Percutaneous intrahepatic transfection into chimpanzee

FIG. 17F

#1b -6. pCV-H77C(VR-24)

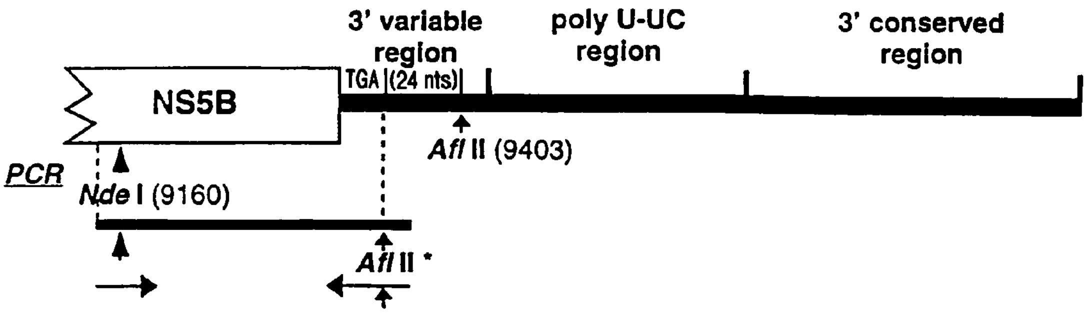

1. PCR Amplification
2. Purification of PCR products
3. Digestion with *Nde* I and *Afl* I
4. Cloning of *Nde* I /*Afl* II fragment into pCV-H77C
5. Complete sequence analysis
6. in vitro transcription (within 24 hours of inoculation)
7. Percutaneous intrahepatic transfection into chimpanzee

#1b -7. pCV-H77C(-U/UC)

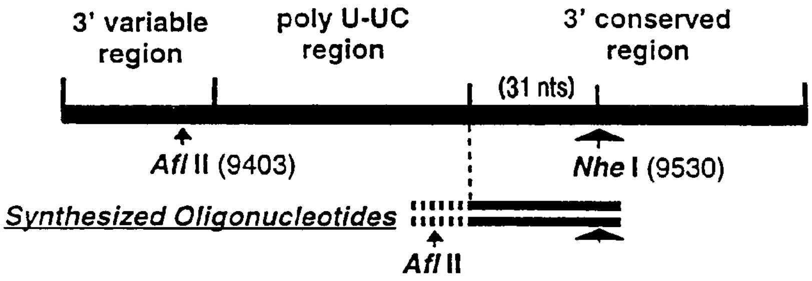

1. Synthesis of oligonucleotides ( sense and anti-sense )
2. Hybridization of oligonucleotides
3. Digestion with *Afl* II and *Nhe* I
4. Cloning of *Afl* II and *Nhe* I fragment into pG9-KL26
5. Sequence analysis
6. Cloning of 3' UTR ( -poly U-UC ) [*Afl* II /*Xba* I fragment] into pCV-H77C
7. Complete sequence analysis
8. in vitro transcription (within 24 hours of inoculation)
9. Percutaneous intrahepatic transfection into chimpanzee

FIG. 17G

CLONED GENOMES OF INFECTIOUS HEPATITIS C VIRUSES AND USES THEREOF

This application is a divisional of U.S. Ser. No. 09/014,416 filed Jan. 27, 1998 now U.S. Pat. No. 6,153,421, which claims the benefit of U.S. Provisional Application No. 60/053,062 filed Jul. 18, 1997

FIELD OF INVENTION

The present invention relates to molecular approaches to the production of nucleic acid sequences which comprise the genome of infectious hepatitis C viruses. In particular, the invention provides nucleic acid sequences which comprise the genomes of infectious hepatitis C viruses of genotype 1a and 1b strains. The invention therefore relates to the use of these sequences, and polypeptides encoded by all or part of these sequences, in the development of vaccines and diagnostic assays for HCV and in the development of screening assays for the identification of antiviral agents for HCV.

BACKGROUND OF INVENTION

Hepatitis C virus (HCV) has a positive-sense single-strand RNA genome and is a member of the virus family Flaviviridae (Choo et al., 1991; Rice, 1996). As for all positive-stranded RNA viruses, the genome of HCV functions as mRNA from which all viral proteins necessary for propagation are translated.

The viral genome of HCV is approximately 9600 nucleotides (nts) and consists of a highly conserved 5' untranslated region (UTR), a single long open reading frame (ORF) of approximately 9,000 nts and a complex 3' UTR. The 5' UTR contains an internal ribosomal entry site (Tsukiyama-Kohara et al., 1992; Honda et al., 1996). The 3' UTR consists of a short variable region, a polypyrimidine tract of variable length and, at the 3' end, a highly conserved region of approximately 100 nts (Kolykhalov et al., 1996; Tanaka et al., 1995; Tanaka et al., 1996; Yamada et al., 1996). The last 46 nucleotides of this conserved region were predicted to form a stable stem-loop structure thought to be critical for viral replication (Blight and Rice, 1997; Ito and Lai, 1997; Tsuchihara et al., 1997). The ORF encodes a large polypeptide precursor that is cleaved into at least 10 proteins by host and viral proteinases (Rice, 1996). The predicted envelope proteins contain several conserved N-linked glycosylation sites and cysteine residues (Okamoto et al., 1992a). The NS3 gene encodes a serine protease and an RNA helicase and the NS5B gene encodes an RNA-dependent RNA polymerase.

Globally, six major HCV genotypes (genotypes 1–6) and multiple subtypes (a, b, c, etc.) have been identified (Bukh et al., 1993; Simmonds et al., 1993). The most divergent HCV isolates differ from each other by more than 30% over the entire genome (Okamoto et al., 1992a) and HCV circulates in an infected individual as a quasispecies of closely related genomes (Bukh et al., 1995; Farci et al., 1997).

At present, more than 80% of individuals infected with HCV become chronically infected and these chronically infected individuals have a relatively high risk of developing chronic hepatitis, liver cirrhosis and hepatocellular carcinoma (Hoofnagle, 1997). In the U.S., HCV genotypes 1a and 1b constitute the majority of infections while in many other areas, especially in Europe and Japan, genotype 1b predominates.

The only effective therapy for chronic hepatitis C, interferon (IFN), induces a sustained response in less than 25% of treated patients (Fried and Hoofnagle, 1995). Consequently, HCV is currently the most common cause of end stage liver failure and the reason for about 30% of liver transplants performed in the U.S. (Hoofnagle, 1997). In addition, a number of recent studies suggested that the severity of liver disease and the outcome of therapy may be genotype-dependent (reviewed in Bukh et al., 1997). In particular, these studies suggested that infection with HCV genotype 1b was associated with more severe liver disease (Brechot, 1997) and a poorer response to IFN therapy (Fried and Hoofnagle, 1995). As a result of the inability to develop a universally effective therapy against HCV infection, it is estimated that there are still more than 25,000 new infections yearly in the U.S. (Alter 1997) Moreover, since there is no vaccine for HCV, HCV remains a serious public health problem.

However, despite the intense interest in the development of vaccines and therapies for HCV, progress has been hindered by the absence of a useful cell culture system and the lack of any small animal model for laboratory study. For example, while replication of HCV in several cell lines has been reported, such observations have turned out not to be highly reproducible. In addition, the chimpanzee is the only animal model, other than man, for this disease. Consequently, HCV has been able to be studied only by using clinical materials obtained from patients or experimentally infected chimpanzees (an animal model whose availability is very limited).

However, several researchers have recently reported the construction of infectious cDNA clones of HCV, the identification of which would permit a more effective search for susceptible cell lines and facilitate molecular analysis of the viral genes and their function. For example, Dash et al., (1997) and Yoo et al., (1995) reported that RNA transcripts from cDNA clones of HCV-1 (genotype 1a) and HCV-N (genotype 1b), respectively, resulted in viral replication after transfection into human hepatoma cell lines. Unfortunately, the viability of these clones was not tested in vivo and concerns were raised about the infectivity of these cDNA clones in vitro (Fausto, 1997). In addition, both clones did not contain the terminal 98 conserved nucleotides at the very 3' end of the UTR.

Kolykhalov et al., (1997) and Yanagi et al. (1997) reported the derivation from HCV strain H77 (which is genotype 1a) of cDNA clones of HCV that are infectious for chimpanzees. However, while these infectious clones will aid in studying HCV replication and pathogenesis and will provide an important tool for development of in vitro replication and propagation systems, it is important to have infectious clones of more than one genotype given the extensive genetic heterogeneity of HCV and the potential impact of such heterogeneity on the development of effective therapies and vaccines for HCV.

SUMMARY OF THE INVENTION

The present invention relates to nucleic acid sequences which comprise the genome of infectious hepatitis C viruses and in particular, nucleic acid sequences which comprise the genome of infectious hepatitis C viruses of genotype 1a and 1b strains. It is therefore an object of the invention to provide nucleic acid sequences which encode infectious hepatitis C viruses. Such nucleic acid sequences are referred to throughout the application as "infectious nucleic acid sequences".

For the purposes of this application, nucleic acid sequence refers to RNA, DNA, cDNA or any variant thereof capable of directing host organism synthesis of a hepatitis C virus polypeptide. It is understood that nucleic acid sequence encompasses nucleic acid sequences, which due to degeneracy, encode the same polypeptide sequence as the nucleic acid sequences described herein.

The invention also relates to the use of the infectious nucleic acid sequences to produce chimeric genomes consisting of portions of the open reading frames of infectious nucleic acid sequences of other genotypes (including, but not limited to, genotypes 1, 2, 3, 4, 5 and 6) and subtypes (including, but not limited to, subtypes 1a, 1b, 2a, 2b, 2c, 3a 4a–4f, 5a and 6a) of HCV. For example infectious nucleic acid sequence of the 1a and 1b strains H77 and HC-J4, respectively, described herein can be used to produce chimeras with sequences from the genomes of other strains of HCV from different genotypes or subtypes. Nucleic acid sequences which comprise sequence from the open-reading frames of 2 or more HCV genotypes or subtypes are designated "chimeric nucleic acid sequences".

The invention further relates to mutations of the infectious nucleic acid sequences of the invention where mutation includes, but is not limited to, point mutations, deletions and insertions. In one embodiment, a gene or fragment thereof can be deleted to determine the effect of the deleted gene or genes on the properties of the encoded virus such as its virulence and its ability to replicate. In an alternative embodiment, a mutation may be introduced into the infectious nucleic acid sequences to examine the effect of the mutation on the properties of the virus in the host cell.

The invention also relates to the introduction of mutations or deletions into the infectious nucleic acid sequences in order to produce an attenuated hepatitis C virus suitable for vaccine development.

The invention further relates to the use of the infectious nucleic acid sequences to produce attenuated viruses via passage in vitro or in vivo of the viruses produced by transfection of a host cell with the infectious nucleic acid sequence.

The present invention also relates to the use of the nucleic acid sequences of the invention or fragments thereof in the production of polypeptides where "nucleic acid sequences of the invention" refers to infectious nucleic acid sequences, mutations of infectious nucleic acid sequences, chimeric nucleic acid sequences and sequences which comprise the genome of attenuated viruses produced from the infectious nucleic acid sequences of the invention. The polypeptides of the invention, especially structural polypeptides, can serve as immunogens in the development of vaccines or as antigens in the development of diagnostic assays for detecting the presence of HCV in biological samples.

The invention therefore also relates to vaccines for use in immunizing mammals especially humans against hepatitis C. In one embodiment, the vaccine comprises one or more polypeptides made from a nucleic acid sequence of the invention or fragment thereof. In a second embodiment, the vaccine comprises a hepatitis C virus produced by transfection of host cells with the nucleic acid sequences of the invention.

The present invention therefore relates to methods for preventing hepatitis C in a mammal. In one embodiment the method comprises administering to a mammal a polypeptide or polypeptides encoded by a nucleic acid sequence of the invention in an amount effective to induce protective immunity to hepatitis C. In another embodiment, the method of prevention comprises administering to a mammal a hepatitis C virus of the invention in an amount effective to induce protective immunity against hepatitis C.

In yet another embodiment, the method of protection comprises administering to a mammal a nucleic acid sequence of the invention or a fragment thereof in an amount effective to induce protective immunity against hepatitis C.

The invention also relates to hepatitis C viruses produced by host cells transfected with the nucleic acid sequences of the present invention.

The invention therefore also provides pharmaceutical compositions comprising the nucleic acid sequences of the invention and/or their encoded hepatitis C viruses. The invention further provides pharmaceutical compositions comprising polypeptides encoded by the nucleic acid sequences of the invention or fragments thereof. The pharmaceutical compositions of the invention may be used prophylactically or therapeutically.

The invention also relates to antibodies to the hepatitis C viruses of the invention or their encoded polypeptides and to pharmaceutical compositions comprising these antibodies.

The present invention further relates to polypeptides encoded by the nucleic acid sequences of the invention fragments thereof. In one embodiment, said polypeptide or polypeptides are fully or partially purified from hepatitis C virus produced by cells transfected with nucleic acid sequence of the invention. In another embodiment, the polypeptide or polypeptides are produced recombinantly from a fragment of the nucleic acid sequences of the invention. In yet another embodiment, the polypeptides are chemically synthesized.

The invention also relates to the use of the nucleic acid sequences of the invention to identify cell lines capable of supporting the replication of HCV in vitro.

The invention further relates to the use of the nucleic acid sequences of the invention or their encoded proteases (e.g. NS3 protease) to develop screening assays to identify antiviral agents for HCV.

BRIEF DESCRIPTION OF FIGURES

FIGS. 4A–4F show the complete nucleotide (SEQ ID NO:2) of a H77C clone produced according to the present invention and FIGS. 4G–4H show the amino acid (SEQ ID NO:1) encoded by the H77C clone.

FIGS. 7A through 7D shows amino acid positions with a quasispecies of HC-J4 in the acute phase plasma pool obtained from an experimentally infected chimpanzee. Cons-p9: consensus amino acid sequence deduced from analysis of nine L fragments and nine S fragments (see FIG. 6). Cons-D: consensus sequence derived from direct sequencing of the PCR product. A, B, C: groups of similar viral species. Dot: amino acid identical to that in Cons-p 9. Capital letter: amino acid different from that in Cons-p9. Cons-F: composite consensus amino acid sequence combining Cons-p9 and Cons-D. Boxed amino acid: different from that in Cons-F. Shaded amino acid: different from that in all species A sequences. An *: defective ORF due to a nucleotide deletion (clone L1, aa 1097) or insertion (clone L7, aa 2770). Diagonal lines: fragments used to construct the infectious clone.

FIG. 8 shows comparisons (percent difference) of nucleotide (nts. 156–8935) and predicted amino acid sequences (aa 1–2864) of L clones (species A, B, and C, this study), HC-J4/91 (Okamoto et al., 1992b) and HC-J4/83 (Okamoto et al., 1992b). Differences among species A sequences and among species B sequences are shaded.

FIG. 10 shows the alignment of the HVR 1 SEQ ID NOS:28, 30, 32, 34, 36–38, 41, 43 and 45 and HVR2 SEQ ID NOS: 29, 31, 33, 35, 39, 40, 42, 44 and 46 amino acid sequences of the E2 sequences of nine L clones of HC-J4 (species A, B, and C) obtained from an early acute phase plasma pool of an experimentally infected chimpanzee compared with the sequences of eight clones (HC-J4/91-20 through HC-J4/91-27, Okamoto et al., 1992b) derived from the inoculum. Dot: an amino acid identical to that in the top line. Capital letters: amino acid different from that in the top line.

FIG. 11 shows the alignment of the 5' UTR and the 3' UTR sequences of infectious clones of genotype 1a pCV-H77C) and 1b (pCV-J4L6S). 5' UTR for HC-J4 is SEQ ID NO:47, 5' UTR for pCV-J4L6S is SEQ ID NO:48, 5' UTR for pCV-H77C is SEQ ID NO: 49, 3' UTR-3' variable region for HC-J4 is SEQ ID NO 50 and 53, 3' UTR-3' variable region for pCV-J4L6S is SEQ ID NO:51 and 54, 3' UTR-3' variable region for pCV-H77C is SEQ ID NO:52 and 54; 3' UTR-3' conserved region for H77, pCV-J4L6S and pCV-H77C is SEQ ID NO 55. Top line: consensus sequence of the indicated strain. Dot: identity with consensus sequence. Capital letter: different from the consensus sequence. Dash: deletion. Underlined: PinAI and BfrI cleavage site. Numbering corresponds to the HCV sequence of pCV-J4L6S.

FIGS. 14A–14F show the nucleotide sequence of the infectious clone of genotype 1b strain HC-J4 (SEQ ID NO:4) FIGS. 14G–14H show the amino acid (SEQ ID NO:3) encoded by the HC-J4 clone.

FIG. 15 shows the strategy for constructing a chimeric HCV clone designated pH77CV-J4 which contains the nonstructural region of the infectious clone of genotype 1a strain H77 and the structural region of the infectious clone of genotype 1b strain HC-J4.

FIGS. 16A–16F show the nucleotide sequence of the chimeric 1a/1b clone pH77CV-J4 (SEQ ID NO:6) of FIG. 15 and FIGS. 16G–16H show the amino acid sequence encoded by the chimeric 1a/1b (SEQ ID NO:5).

FIGS. 17A and 17B show the sequence of the 3' untranslated region remaining in various 3' deletion mutants of the 1a infectious clone pCV-H77C, (pCV-H77C has SEQ ID NOS:56, 57 and 58; pCV-H77C (−98X) has SEQ ID NO:59; pCV-H77C (−42X) has SEQ ID NO:60; pCV-H77C (X-52) has SEQ ID NO:61; pCV-H77C(X) has SEQ ID NO:62; pCV-H77C(+49X) has SEQ ID NO:63; pCV-H77C (VR-24) has SEQ ID NO:64; and pCV-H77C (−U/UC) has SEQ ID NO:65). and the strategy utilized in constructing each 3' deletion mutant (FIGS. 17C–17G).

Of the seven deletion mutants shown, two (pCV-H77C(−98X) and (−42X)) have been constructed and tested for infectivity in chimpanzees (see FIGS. 17A and 17C) and the other six are to be constructed and tested for infectivity as described in FIGS. 17D–17G.

Figure 18A:
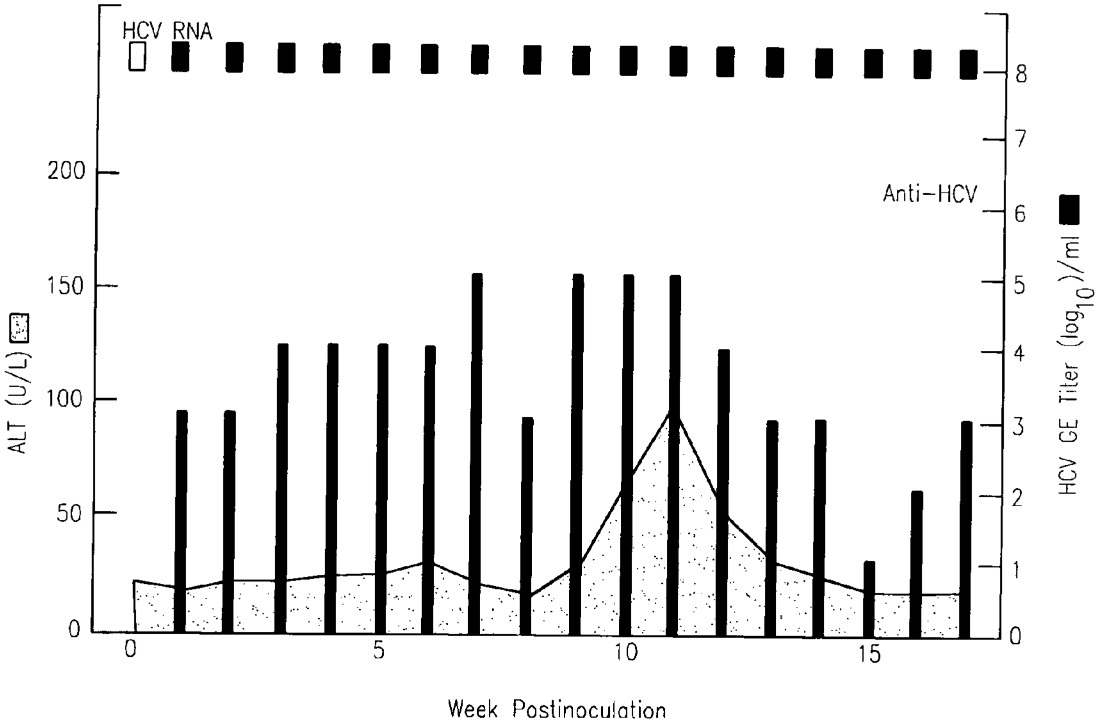
Figure 18B:
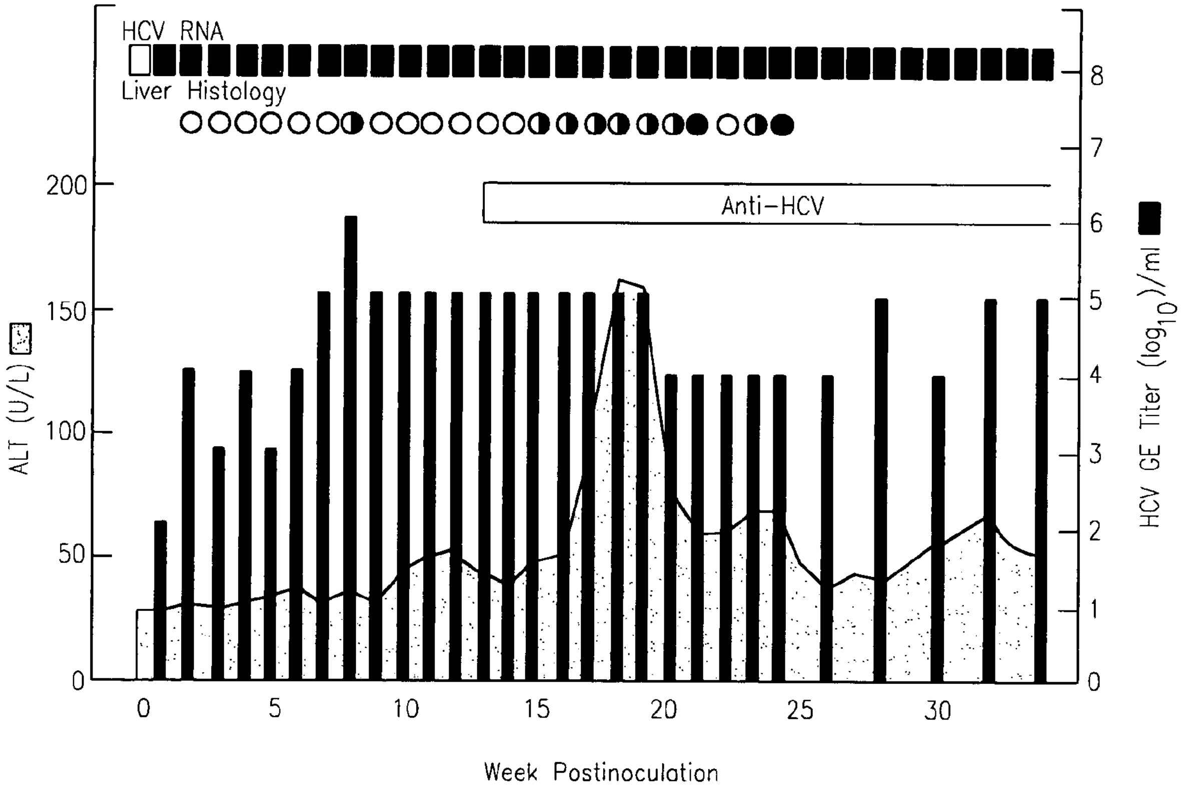

FIGS. 18A and 18B show biochemical (ALT levels), PCR(HCV RNA and HCV GE titer), serological (anti-HCV) and histopathological (FIG. 18B only) analyses of chimpanzees 1494 (FIG. 18A) and 1530 (FIG. 18B) following transfection with the infectious cDNA clone pCV-H77C.

The ALT serum enzyme levels were measured in units per ml (u/l). For the PCR analysis, "HCV RNA" represented by an open rectangle indicates a serum sample that was negative for HCV after nested PCR; "HCV RNA" represented by a closed rectangle indicates that the serum sample was positive for HCV; and HCV GE titer on the right-hand y-axis represents genome equivalents.

The bar marked "anti-HCV" indicates samples that were positive for anti-HCV antibodies as determined by commercial assays. The histopathology scores in FIG. 18B correspond to no histopathology (○), mild hepatitis (⊖) and moderate to severe hepatitis (●).

DESCRIPTION OF THE INVENTION

The present invention relates to nucleic acid sequences which comprise the genome of an infectious hepatitis C virus. More specifically, the invention relates to nucleic acid sequences which encode infectious hepatitis C viruses of genotype 1a and 1b strains. In one embodiment, the infectious nucleic acid sequence of the invention has the sequence shown in FIGS. 4A–4F of this application. In another embodiment, the infectious nucleic acid sequence has the sequence shown in FIGS. 14A–14F and is contained in a plasmid construct deposited with the American Type Culture Collection (ATCC) on Jan. 26, 1998 and having ATCC accession number 209596.

The invention also relates to "chimeric nucleic acid sequences" where the chimeric nucleic acid sequences consist of open-reading frame sequences taken from infectious nucleic acid sequences of hepatitis C viruses of different genotypes or subtypes.

In one embodiment, the chimeric nucleic acid sequence consists of sequence from the genome of an HCV strain belonging to one genotype or subtype which encodes structural polypeptides and sequence of an HCV strain belonging to another genotype strain or subtype which encodes nonstructural polypeptides. Such chimeras can be produced by standard techniques of restriction digestion, PCR amplification and subcloning known to those of ordinary skill in the art.

In a preferred embodiment, the sequence encoding nonstructural polypeptides is from an infectious nucleic acid sequence encoding a genotype 1a strain where the construction of a chimeric 1a/1b nucleic acid sequence is described in Example 9 and the chimeric 1a/1b nucleic acid sequence is shown in FIGS. 16A–16F. It is believed that the construction of such chimeric nucleic acid sequences will be of importance in studying the growth and virulence properties of hepatitis C virus and in the production of hepatitis C viruses suitable to confer protection against multiple genotypes of HCV. For example, one might produce a "multivalent" vaccine by putting epitopes from several genotypes or subtypes into one clone. Alternatively one might replace just a single gene from an infectious sequence with the corresponding gene from the genomic sequence of a strain from another genotype or subtype or create a chimeric gene which contains portions of a gene from two genotypes or subtypes. Examples of genes which could be replaced or which could be made chimeric, include, but are not limited to, the E1, E2 and NS4 genes.

The invention further relates to mutations of the infectious nucleic acid sequences where "mutations" includes, but is not limited to, point mutations, deletions and insertions. Of course, one of ordinary skill in the art would recognize that the size of the insertions would be limited by the ability of the resultant nucleic acid sequence to be properly packaged within the virion. Such mutation could be produced by techniques known to those of skill in the art such as site-directed mutagenesis, fusion PCR, and restriction digestion followed by religation.

In one embodiment, mutagenesis might be undertaken to determine sequences that are important for viral properties such as replication or virulence. For example, one may introduce a mutation into the infectious nucleic acid sequence which eliminates the cleavage site between the NS4A and NS4B polypeptides to examine the effects on viral replication and processing of the polypeptide. Alternatively, one or more of the 3 amino acids encoded by the infectious 1b nucleic acid sequence shown in FIGS. 14A–14F which differ from the HC-J4 consensus sequence may be back mutated to the corresponding amino acid in the HC-J4 consensus sequence to determine the importance of these three amino acid changes to infectivity or virulence. In yet another embodiment, one or more of the amino acids from the noninfectious 1b clones pCV-J4L2S and pCV-J4L4S which differ from the consensus sequence may be introduced into the infectious 1b sequence shown in FIGS. 14A–14F.

In yet another example, one may delete all or part of a gene or of the 5' or 3' nontranslated region contained in an infectious nucleic acid sequence and then transfect a host cell (animal or cell culture) with the mutated sequence and measure viral replication in the host by methods known in the art such as RT-PCR. Preferred genes include, but are not limited to, the P7, NS4B and NS5A genes. Of course, those of ordinary skill in the art will understand that deletion of part of a gene, preferably the central portion of the gene, may be preferable to deletion of the entire gene in order to conserve the cleavage site boundaries which exist between proteins in the HCV polyprotein and which are necessary for proper processing of the polyprotein.

In the alternative, if the transfection is into a host animal such as a chimpanzee, one can monitor the virulence phenotype of the virus produced by transfection of the mutated infectious nucleic acid sequence by methods known in the art such as measurement of liver enzyme levels (alanine aminotransferase (ALT) or isocitrate dehydrogenase (ICD)) or by histopathology of liver biopsies. Thus, mutations of the infectious nucleic acid sequences may be useful in the production of attenuated HCV strains suitable for vaccine use.

The invention also relates to the use of the infectious nucleic acid sequences of the present invention to produce attenuated viral strains via passage in vitro or in vivo of the virus produced by transfection with the infectious nucleic acid sequences.

The present invention therefore relates to the use of the nucleic acid sequences of the invention to identify cell lines capable of supporting the replication of HCV.

In particular, it is contemplated that the mutations of the infectious nucleic acid sequences of the invention and the production of chimeric sequences as discussed above may be useful in identifying sequences critical for cell culture adaptation of HCV and hence, may be useful in identifying cell lines capable of supporting HCV replication.

Transfection of tissue culture cells with the nucleic acid sequences of the invention may be done by methods of transfection known in the art such as electroporation, precipitation with DEAE-Dextran or calcium phosphate or liposomes.

In one such embodiment, the method comprises the growing of animal cells, especially human cells, in vitro and transfecting the cells with the nucleic acid of the invention, then determining if the cells show indicia of HCV infection. Such indicia include the detection of viral antigens in the cell, for example, by immunofluorescent procedures well known in the art; the detection of viral polypeptides by Western blotting using antibodies specific therefor; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the symptoms of HCV infection.

Suitable cells or cell lines for culturing HCV include, but are not limited to, lymphocyte and hepatocyte cell lines known in the art.

Alternatively, primary hepatocytes can be cultured, and then infected with HCV; or, the hepatocyte cultures could be derived from the livers of infected chimpanzees. In addition, various immortalization methods known to those of ordinary skill in the art can be used to obtain cell-lines derived from hepatocyte cultures. For example, primary hepatocyte cultures may be fused to a variety of cells to maintain stability.

The present invention further relates to the in vitro and in vivo production of hepatitis C viruses from the nucleic acid sequences of the invention.

In one embodiment, the sequences of the invention can be inserted into an expression vector that functions in eukaryotic cells. Eukaryotic expression vectors suitable for producing high efficiency gene transfer in vivo are well known to those of ordinary skill in the art and include, but are not limited to, plasmids, vaccinia viruses, retroviruses, adenoviruses and adeno-associated viruses.

In another embodiment, the sequences contained in the recombinant expression vector can be transcribed in vitro by methods known to those of ordinary skill in the art in order to produce RNA transcripts which encode the hepatitis C viruses of the invention. The hepatitis C viruses of the invention may then be produced by transfecting cells by methods known to those of ordinary skill in the art with either the in vitro transcription mixture containing the RNA transcripts (see Example 4) or with the recombinant expression vectors containing the nucleic acid sequences described herein.

The present invention also relates to the construction of cassette vectors useful in the cloning of viral genomes wherein said vectors comprise a nucleic acid sequence to be cloned, and said vector reading in the correct phase for the expression of the viral nucleic acid to be cloned. Such a cassette vector will, of course, also possess a promoter sequence, advantageously placed upstream of the sequence to be expressed. Cassette vectors according to the present invention are constructed according to the procedure described in FIG. 1, for example, starting with plasmid pCv. Of course, the DNA to be inserted into said cassette vector can be derived from any virus, advantageously from HCV, and most advantageously from the H77 strain of HCV. The nucleic acid to be inserted according to the present invention can, for example, contain one or more open reading frames of the virus, for example, HCV. The cassette vectors of the present invention may also contain, optionally, one or more expressible marker genes for expression as an indication of successful transfection and expression of the nucleic acid sequences of the vector. To insure expression, the cassette vectors of the present invention will contain a promoter sequence for binding of the appropriate cellular RNA polymerase, which will depend on the cell into which the vector has been introduced. For example, if the host cell is a bacterial cell, then said promoter will be a bacterial promoter sequence to which the bacterial RNA polymerases will bind.

The hepatitis C viruses produced from the sequences of the invention may be purified or partially purified from the transfected cells by methods known to those of ordinary skill in the art. In a preferred embodiment, the viruses are partially purified prior to their use as immunogens in the pharmaceutical compositions and vaccines of the present invention.

The present invention therefore relates to the use of the hepatitis C viruses produced from the nucleic acid sequences of the invention as immunogens in live or killed (e.g., formalin inactivated) vaccines to prevent hepatitis C in a mammal.

In an alternative embodiment, the immunogen of the present invention may be an infectious nucleic acid sequence, a chimeric nucleic acid sequence, or a mutated infectious nucleic acid sequence which encodes a hepatitis C virus. Where the sequence is a cDNA sequence, the cDNAs and their RNA transcripts may be used to transfect a mammal by direct injection into the liver tissue of the mammal as described in the Examples.

Alternatively, direct gene transfer may be accomplished via administration of a eukaryotic expression vector containing a nucleic acid sequence of the invention.

In yet another embodiment, the immunogen may be a polypeptide encoded by the nucleic acid sequences of the invention. The present invention therefore also relates to polypeptides produced from the nucleic acid sequences of the invention or fragments thereof. In one embodiment, polypeptides of the present invention can be recombinantly produced by synthesis from the nucleic acid sequences of the invention or isolated fragments thereof, and purified, or partially purified, from transfected cells using methods already known in the art. In an alternative embodiment, the polypeptides may be purified or partially purified from viral particles produced via transfection of a host cell with the nucleic acid sequences of the invention. Such polypeptides might, for example, include either capsid or envelope polypeptides prepared from the sequences of the present invention.

When used as immunogens, the nucleic acid sequences of the invention, or the polypeptides or viruses produced therefrom, are preferably partially purified prior to use as immunogens in pharmaceutical compositions and vaccines of the present invention. When used as a vaccine, the sequences and the polypeptide and virus products thereof, can be administered alone or in a suitable diluent, including, but not limited to, water, saline, or some type of buffered medium. The vaccine according to the present invention may be administered to an animal, especially a mammal, and most especially a human, by a variety of routes, including, but not limited to, intradermally, intramuscularly, subcutaneously, or in any combination thereof.

Suitable amounts of material to administer for prophylactic and therapeutic purposes will vary depending on the route selected and the immunogen (nucleic acid, virus, polypeptide) administered. One skilled in the art will appreciate that the amounts to be administered for any particular treatment protocol can be readily determined without undue experimentation. The vaccines of the present invention may be administered once or periodically until a suitable titer of anti-HCV antibodies appear in the blood. For an immunogen consisting of a nucleic acid sequence, a suitable amount of nucleic acid sequence to be used for prophylactic purposes might be expected to fall in the range of from about 100 μg to about 5 mg and most preferably in the range of from about 500 μg to about 2 mg. For a polypeptide, a suitable amount to use for prophylactic purposes is preferably 100 ng to 100 μg and for a virus $10^2$ to $10^6$ infectious doses. Such administration will, of course, occur prior to any sign of HCV infection.

A vaccine of the present invention may be employed in such forms as capsules, liquid solutions, suspensions or elixirs for oral administration, or sterile liquid forms such as solutions or suspensions. Any inert carrier is preferably used, such as saline or phosphate-buffered saline, or any such carrier in which the HCV of the present invention can be suitably suspended. The vaccines may be in the form of single dose preparations or in multi-dose flasks which can be utilized for mass-vaccination programs of both animals and humans. For purposes of using the vaccines of the present invention reference is made to Remington's *Pharmaceutical Sciences*, Mack Publishing Co., Easton, Pa., Osol (Ed.) (1980); and *New Trends and Developments in Vaccines*, Voller et al. (Eds.), University Park Press, Baltimore, Md. (1978), both of which provide much useful information for preparing and using vaccines. Of course, the polypeptides of the present invention, when used as vaccines, can include, as part of the composition or emulsion, a suitable adjuvant, such as alum (or aluminum hydroxide) when humans are to be vaccinated, to further stimulate production of antibodies by immune cells. When nucleic acids or viruses are used for vaccination purposes, other specific adjuvants such as CpG motifs (Krieg, A. K. et al. (1995) and (1996)), may prove useful.

When the nucleic acids, viruses and polypeptides of the present invention are used as vaccines or inocula, they will normally exist as physically discrete units suitable as a unitary dosage for animals, especially mammals, and most especially humans, wherein each unit will contain a predetermined quantity of active material calculated to produce the desired immunogenic effect in association with the required diluent. The dose of said vaccine or inoculum according to the present invention is administered at least once. In order to increase the antibody level, a second or booster dose may be administered at some time after the initial dose. The need for, and timing of, such booster dose will, of course, be determined within the sound judgment of the administrator of such vaccine or inoculum and according to sound principles well known in the art. For example, such booster dose could reasonably be expected to be advantageous at some time between about 2 weeks to about 6 months following the initial vaccination. Subsequent doses may be administered as indicated.

The nucleic acid sequences, viruses and polypeptides of the present invention can also be administered for purposes of therapy, where a mammal, especially a primate, and most especially a human, is already infected, as shown by well known diagnostic measures. When the nucleic acid sequences, viruses or polypeptides of the present invention are used for such therapeutic purposes, much of the same criteria will apply as when it is used as a vaccine, except that inoculation will occur post-infection. Thus, when the nucleic acid sequences, viruses or polypeptides of the present invention are used as therapeutic agents in the treatment of infection, the therapeutic agent comprises a pharmaceutical composition containing a sufficient amount of said nucleic acid sequences, viruses or polypeptides so as to elicit a therapeutically effective response in the organism to be treated. Of course, the amount of pharmaceutical composition to be administered will, as for vaccines, vary depending on the immunogen contained therein (nucleic acid, polypeptide, virus) and on the route of administration.

The therapeutic agent according to the present invention can thus be administered by, subcutaneous, intramuscular or intradermal routes. One skilled in the art will certainly appreciate that the amounts to be administered for any particular treatment protocol can be readily determined without undue experimentation. Of course, the actual amounts will vary depending on the route of administration as well as the sex, age, and clinical status of the subject which, in the case of human patients, is to be determined with the sound judgment of the clinician.

The therapeutic agent of the present invention can be employed in such forms as capsules, liquid solutions, suspensions or elixirs, or sterile liquid forms such as solutions or suspensions. Any inert carrier is preferably used, such as saline, phosphate-buffered saline, or any such carrier in which the HCV of the present invention can be suitably suspended. The therapeutic agents may be in the form of single dose preparations or in the multi-dose flasks which can be utilized for mass-treatment programs of both animals and humans. Of course, when the nucleic acid sequences, viruses or polypeptides of the present invention are used as therapeutic agents they may be administered as a single dose or as a series of doses, depending on the situation as determined by the person conducting the treatment.

The nucleic acids, polypeptides and viruses of the present invention can also be utilized in the production of antibodies against HCV. The term "antibody" is herein used to refer to immunoglobulin molecules and immunologically active portions of immunoglobulin molecules. Examples of antibody molecules are intact immunoglobulin molecules, substantially intact immunoglobulin molecules and portions of an immunoglobulin molecule, including those portions known in the art as Fab, $F(ab')_2$ and F(v) as well as chimeric antibody molecules.

Thus, the polypeptides, viruses and nucleic acid sequences of the present invention can be used in the generation of antibodies that immunoreact (i.e., specific binding between an antigenic determinant-containing molecule and a molecule containing an antibody combining site such as a whole antibody molecule or an active portion thereof) with antigenic determinants on the surface of hepatitis C virus particles.

The present invention therefore also relates to antibodies produced following immunization with the nucleic acid sequences, viruses or polypeptides of the present invention. These antibodies are typically produced by immunizing a mammal with an immunogen or vaccine to induce antibody molecules having immunospecificity for polypeptides or viruses produced in response to infection with the nucleic acid sequences of the present invention. When used in generating such antibodies, the nucleic acid sequences, viruses, or polypeptides of the present invention may be linked to some type of carrier molecule. The resulting antibody molecules are then collected from said mammal. Antibodies produced according to the present invention have the unique advantage of being generated in response to authentic, functional polypeptides produced according to the actual cloned HCV genome.

The antibody molecules of the present invention may be polyclonal or monoclonal. Monoclonal antibodies are readily produced by methods well known in the art. Portions of immunoglobin molecules, such as Fabs, as well as chimeric antibodies, may also be produced by methods well known to those of ordinary skill in the art of generating such antibodies.

The antibodies according to the present invention may also be contained in blood plasma, serum, hybridoma supernatants, and the like. Alternatively, the antibody of the present invention is isolated to the extent desired by well known techniques such as, for example, using DEAE Sephadex. The antibodies produced according to the present invention may be further purified so as to obtain specific classes or subclasses of antibody such as IgM, IgG, IgA, and the like. Antibodies of the IgG class are preferred for purposes of passive protection.

The antibodies of the present invention are useful in the prevention and treatment of diseases caused by hepatitis C virus in animals, especially mammals, and most especially humans.

In providing the antibodies of the present invention to a recipient mammal, preferably a human, the dosage of administered antibodies will vary depending on such factors as the mammal's age, weight, height, sex, general medical condition, previous medical history, and the like.

In general, it will be advantageous to provide the recipient mammal with a dosage of antibodies in the range of from about 1 mg/kg body weight to about 10 mg/kg body weight of the mammal, although a lower or higher dose may be administered if found desirable. Such antibodies will normally be administered by intravenous or intramuscular route as an inoculum. The antibodies of the present invention are intended to be provided to the recipient subject in an amount sufficient to prevent, lessen or attenuate the severity, extent or duration of any existing infection.

The antibodies prepared by use of the nucleic acid sequences, viruses or polypeptides of the present invention are also highly useful for diagnostic purposes. For example, the antibodies can be used as in vitro diagnostic agents to test for the presence of HCV in biological samples taken from animals, especially humans. Such assays include, but are not limited to, radioimmunoassays, EIA, fluorescence, Western blot analysis and ELISAs. In one such embodiment, the biological sample is contacted with antibodies of the present invention and a labeled second antibody is used to detect the presence of HCV to which the antibodies are bound.

Such assays may be, for example, a direct protocol (where the labeled first antibody is immunoreactive with the antigen, such as, for example, a polypeptide on the surface of the virus), an indirect protocol (where a labeled second antibody is reactive with the first antibody), a competitive protocol (such as would involve the addition of a labeled antigen), or a sandwich protocol (where both labeled and unlabeled antibody are used), as well as other protocols well known and described in the art.

In one embodiment, an immunoassay method would utilize an antibody specific for HCV envelope determinants and would further comprise the steps of contacting a biological sample with the HCV-specific antibody and then detecting the presence of HCV material in the test sample using one of the types of assay protocols as described above. Polypeptides and antibodies produced according to the present invention may also be supplied in the form of a kit, either present in vials as purified material, or present in compositions and suspended in suitable diluents as previously described.

In a preferred embodiment, such a diagnostic test kit for detection of HCV antigens in a test sample comprises in combination a series of containers, each container a reagent needed for such assay. Thus, one such container would contain a specific amount of HCV-specific antibody as already described, a second container would contain a diluent for suspension of the sample to be tested, a third container would contain a positive control and an additional container would contain a negative control. An additional container could contain a blank.

For all prophylactic, therapeutic and diagnostic uses, the antibodies of the invention and other reagents, plus appropriate devices and accessories, may be provided in the form of a kit so as to facilitate ready availability and ease of use.

The present invention also relates to the use of nucleic acid sequences and polypeptides of the present invention to screen potential antiviral agents for antiviral activity against HCV. Such screening methods are known by those of skill in the art. Generally, the antiviral agents are tested at a variety of concentrations, for their effect on preventing viral replication in cell culture systems which support viral replication, and then for an inhibition of infectivity or of viral pathogenicity (and a low level of toxicity) in an animal model system.

In one embodiment, animal cells (especially human cells) transfected with the nucleic acid sequences of the invention are cultured in vitro and the cells are treated with a candidate antiviral agent (a chemical, peptide etc.) for antiviral activity by adding the candidate agent to the medium. The treated cells are then exposed, possibly under transfecting or fusing conditions known in the art, to the nucleic acid sequences of the present invention. A sufficient period of time would then be allowed to pass for infection to occur, following which the presence or absence of viral replication would be determined versus untreated control cells by methods known to those of ordinary skill in the art. Such methods include, but are not limited to, the detection of viral antigens in the cell, for example, by immunofluorescent procedures well known in the art; the detection of viral polypeptides by Western blotting using antibodies specific therefor; the detection of newly transcribed viral RNA within the cells by RT-PCR; and the detection of the presence of live, infectious virus particles by injection of cell culture medium or cell lysates into healthy, susceptible animals, with subsequent exhibition of the symptoms of HCV infection. A comparison of results obtained for control cells (treated only with nucleic acid sequence) with those obtained for treated cells (nucleic acid sequence and antiviral agent) would indicate, the degree, if any, of antiviral activity of the candidate antiviral agent. Of course, one of ordinary skill in the art would readily understand that such cells can be treated with the candidate antiviral agent either before or after exposure to the nucleic acid sequence of the present invention so as to determine what stage, or stages, of viral infection and replication said agent is effective against.

In an alternative embodiment, a protease such as NS3 protease produced from a nucleic acid sequence of the invention may be used to screen for protease inhibitors which may act as antiviral agents. The structural and nonstructural regions of the HCV genome, including nucleotide and amino acid locations, have been determined, for example, as depicted in Houghton, M. (1996), FIG. 1; and Major, M. E. et al. (1997), Table 1.

Such above-mentioned protease inhibitors may take the form of chemical compounds or peptides which mimic the known cleavage sites of the protease and may be screened using methods known to those of skill in the art (Houghton, M. (1996) and Major, M. E. et al. (1997)). For example, a substrate may be employed which mimics the protease's natural substrate, but which provides a detectable signal (e.g. by fluorimetric or calorimetric methods) when cleaved. This substrate is then incubated with the protease and the candidate protease inhibitor under conditions of suitable pH, temperature etc. to detect protease activity. The proteolytic activities of the protease in the presence or absence of the candidate inhibitor are then determined.

In yet another embodiment, a candidate antiviral agent (such as a protease inhibitor) may be directly assayed in vivo for antiviral activity by administering the candidate antiviral agent to a chimpanzee transfected with a nucleic acid sequence of the invention and then measuring viral replication in vivo via methods such as RT-PCR. Of course, the chimpanzee may be treated with the candidate agent either before or after transfection with the infectious nucleic acid sequence so as to determine what stage, or stages, of viral infection and replication the agent is effective against.

The invention also provides that the nucleic acid sequences, viruses and polypeptides of the invention may be supplied in the form of a kit, alone or in the form of a pharmaceutical composition.

All scientific publication and/or patents cited herein are specifically incorporated by reference. The following examples illustrate various aspects of the invention but are in no way intended to limit the scope thereof.

EXAMPLES

Materials and Methods For Examples 1–4

Collection of Virus

Hepatitis C virus was collected and used as a source for the RNA used in generating the cDNA clones according to the present invention. Plasma containing strain H77 of HCV was obtained from a patient in the acute phase of transfusion-associated non-A, non-B hepatitis (Feinstone et al (1981)). Strain H77 belongs to genotype 1a of HCV (Ogata et al (1991), Inchauspe et al (1991)). The consensus sequence for most of its genome has been determined (Kolyakov et al (1996), Ogata et al (1991), Inchauspe et al (1991) and Farci et al (1996)).

RNA Purification

Viral RNA was collected and purified by conventional means. In general, total RNA from 10 μl of H77 plasma was extracted with the TRIzol system (GIBCO BRL). The RNA pellet was resuspended in 100 μl of 10 mM dithiothreitol (DTT) with 5% (vol/vol) RNasin (20–40 units/μl) (available from Promega) and 10 μl aliquots were stored at −80° C. In subsequent experiments RT-PCR was performed on RNA equivalent to 1 μl of H77 plasma, which contained an estimated $10^5$ genome equivalents (GE) of HCV (Yanagi et al (1996)).

Primers used in the RT-PCR process were deduced from the genomic sequences of strain H77 according to procedures already known in the art (see above) or else were determined specifically for use herein. The primers generated for this purpose are listed in Table 1.

TABLE 1

| Oligonucleotides used for PCR amplification of strain H77 of HCV | |
|---|---|
| Designation | Sequence (5' → 3')* |
| SEQ ID NO:7 | |
| H9261F | GGCTACAGCGGGGGGAGACATTTATCACAGC |
| SEQ ID NO:8 | |
| H3'X58R | TCATGCGGCTCACGGACCTTTCACAGCTAG |
| SEQ ID NO:9 | |
| H9282F | **GTCC**AAGCTTATCACAGCGTGTCTCATGCCCGGCCCCG |
| SEQ ID NO:10 | |
| H3'X45R | **CGTC**TCTAGAGGACCTTTCACAGCTAGCCGTGACTAGGG |
| SEQ ID NO:11 | |
| H9375F | TGAAGGTTGGGGTAAACACTCCGGCCTCTTAGGCCATT |
| SEQ ID NO:12 | |
| H3'X-35R | ACATGATCTGCAGAGAGGCCAGTATCAGCACTCTC |
| SEQ ID NO:13 | |
| H9386F | **GTCC**AAGCTTACGCGTAAACACTCCGGCCTC CTTAAGCCATTCCTG |
| SEQ ID NO:14 | |
| H3'X-38R | **CGTC** TCTAGACATGATCTGCAGAGAGGCCAGTATCAGCACTCTCTGC |
| SEQ ID NO:15 | |
| H1 | **TTTTTTTT**GCGGCCGC ***TAATACGACTCACTATA***GCCAGC-CCCCTGAT-GGGGGCGACACTCCACCATG |

TABLE 1-continued

| Oligonucleotides used for PCR amplification of strain H77 of HCV | |
|---|---|
| Designation | Sequence (5' → 3')* |
| A1 SEQ ID NO:17 | ACTGTCTTCACGCAGAAAGCGTCTAGCCAT |
| H9417R | **CGTC**TCTAGACAGGAAATGGCTTAAGAGGCCGGAGTGTTTACC |

*HCV sequences are shown in plain text, non-HCV-specific sequences are shown in boldface and artificial cleavage sites used for cDNA cloning are underlined. The core sequence of the T7 promoter in primer H1 is shown in italics.

Primers for long RT-PCR were size-purified.

cDNA Synthesis

The RNA was denatured at 65° C. for 2 min, and cDNA synthesis was performed in a 20 μl reaction volume with Superscript II reverse transcriptase (from GIBCO/BRL) at 42° C. for 1 hour using specific antisense primers as described previously (Tellier et al (1996)). The cDNA mixture was treated with RNase H and RNase Ti (GIBCO/BRL) for 20 min at 37° C.

Amplification and Cloning of the 3' UTR

The 3' UTR of strain H77 was amplified by PCR in two different assays. In both of these nested PCR reactions the first round of PCR was performed in a total volume of 50 μl in 1× buffer, 250 μmol of each deoxynucleoside triphosphate (dNTP; Pharmacia), 20 pmol each of external sense and antisense primers, 1 μl of the Advantage KlenTaq polymerase mix (from Clontech) and 2 μl of the final cDNA reaction mixture. In the second round of PCR, 5 μl of the first round PCR mixture was added to 45 μl of PCR mixture prepared as already described. Each round of PCR (35 cycles), which was performed in a Perkin Elmer DNA thermal cycler 480, consisted of denaturation at 94° C. for 1 min (in 1st cycle 1 min 30 sec), annealing at 60° C. for 1 min and elongation at 68° C. for 2 min. In one experiment a region from NS5B to the conserved region of the 3' UTR was amplified with the external primers H9261F and H3'X58R, and the internal primers H9282F and H3'X45R (Table 1). In another experiment, a segment of the variable region to the very end of the 3' UTR was amplified with the external primers H9375F and H3'X-35R, and the internal primers H9386F and H3'X-38R (Table 1, FIG. 1). Amplified products were purified with QIAquick PCR purification kit (from QIAGEN), digested with Hind III and Xba I (from Promega), purified by either gel electrophoresis or phenol/chloroform extraction, and then cloned into the multiple cloning site of plasmid PGEM-9zf(−) (Promega) or pUC19 (Pharmacia). Cloning of cDNA into the vector was performed with T4 DNA ligase (Promega) by standard procedures.

Amplification of Near Full-Length H77 Genomes by Long PCR

The reactions were performed in a total volume of 50 μl in 1× buffer, 250 μmol of each dNTP, 10 pmol each of sense and antisense primers, 1 μl of the Advantage KlenTaq polymerase mix and 2 μl of the cDNA reaction mixture (Tellier et al (1996)). A single PCR round of 35 cycles was performed in a Robocycler thermal cycler (from Stratagene), and consisted of denaturation at 99° C. for 35 sec, annealing at 67° C. for 30 sec and elongation at 6° C. for 10 min during the first 5 cycles, 11 min during the next 10 cycles, 12 min during the following 10 cycles and 13 min during the last 10 cycles. To amplify the complete ORF of HCV by long RT-PCR we used the sense primers H1 or A1 deduced from the 5' UTR and the antisense primer H9417R deduced from the variable region of the 3' UTR (Table 1, FIG. 1).

Construction of Full-Length H77 cDNA Clones

Figure 1:
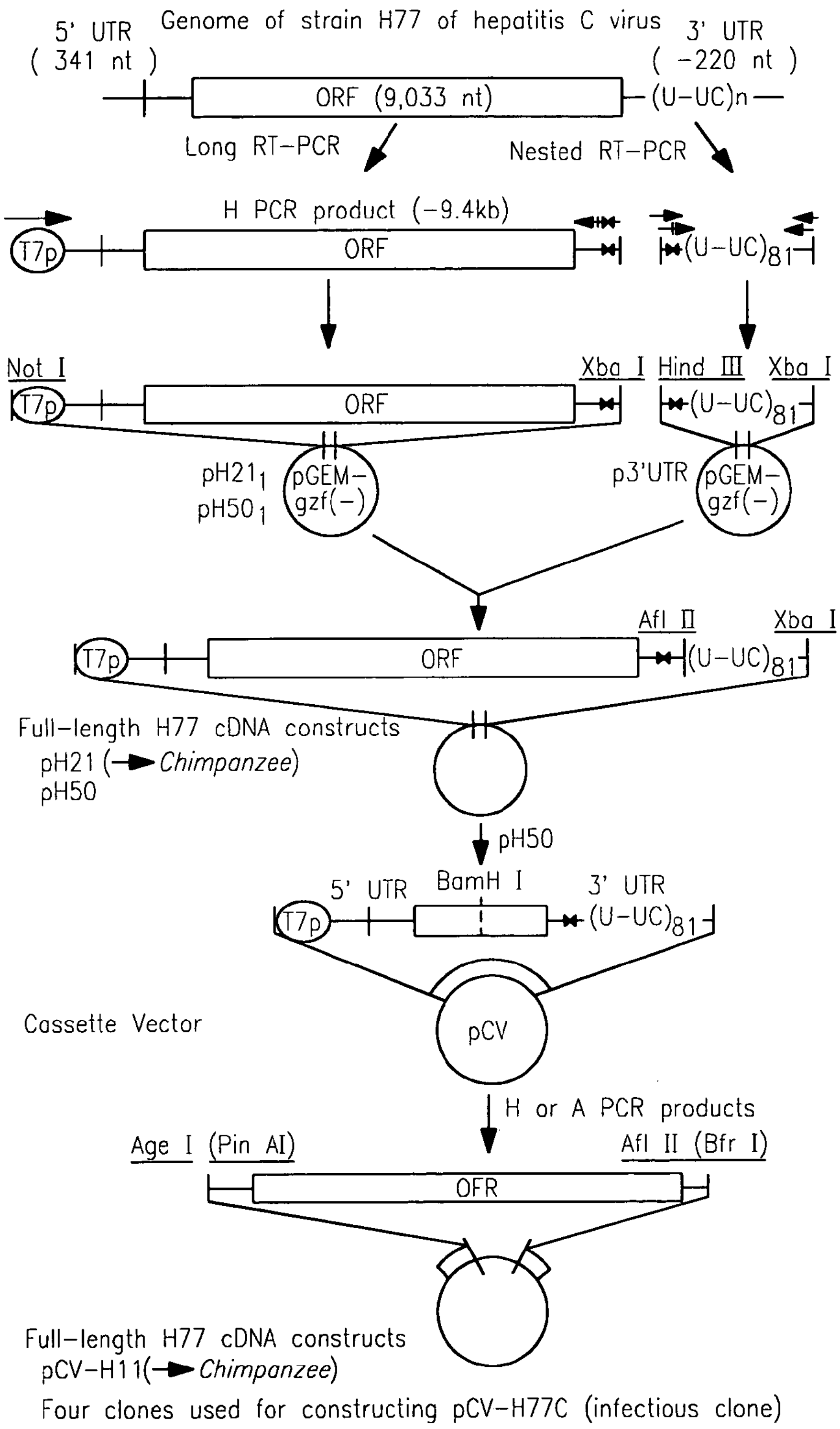
FIG. 1 shows a strategy for constructing full-length cDNA clones of HCV strain H77. The long PCR products amplified with H1 and H9417R primers were cloned directly into pGEM-9zf(−) after digestion with Not I and Xba I ($pH21_1$ and $pHSO_1$). Next, the 3' UTR was cloned into both $pH21_1$ and $pH50_1$ after digestion with Afl II and Xba I (pH21 and pH50). pH21 was tested for infectivity in a chimpanzee. To improve the efficiency of cloning, we constructed a cassette vector with consensus 5' and 3' termini of H77. This cassette vector (pCV) was obtained by cutting out the BamHI fragment (nts 1358–7530 of the H77 genome) from pH50, followed by religation. Finally, the long PCR products of H77 amplified with primers H1 and H9417R(H product) or primers A1 and H9417R (A product) were cloned into pCV after digestion with Age I and Afl II or with Pin AI and Bfr I. The latter procedure yielded multiple complete cDNA clones of strain H77 of HCV.

The long PCR products amplified with H1 and H9417R primers were cloned directly into pGEM-9zf(−) after digestion with Not I and Xba I (from Promega) (as per FIG. 1). Two clones were obtained with inserts of the expected size, $pH21_1$ and $pH50_1$. Next, the chosen 3' UTR was cloned into both $pH21_1$ and $pH50_1$ after digestion with Afl II and Xba I (New England Biolabs). DH5α competent cells (GIBCO/BRL) were transformed and selected with LB agar plates containing 100 μg/ml ampicillin (from SIGMA). Then the selected colonies were cultured in LB liquid containing ampicillin at 30° C. for ~18–20 hrs (transformants containing full-length or near full-length cDNA of H77 produced a very low yield of plasmid when cultured at 37° C. or for more than 24 hrs). After small scale preparation (Wizard Plus Minipreps DNA Purification Systems, Promega) each plasmid was retransformed to select a single clone, and large scale preparation of plasmid DNA was performed with a QIAGEN plasmid Maxi kit.

Cloning of Long RT-PCR Products into a Cassette Vector

To improve the efficiency of cloning, a vector with consensus 5' and 3' termini of HCV strain H77 was constructed (FIG. 1). This cassette vector (pCV) was obtained by cutting out the BamHI fragment (nts 1358-7530 of the H77 genome) from pH50, followed by religation. Next, the long PCR products of H77 amplified with H1 and H9417R or A1 and H9417R primers were purified (Geneclean spin kit; BIO 101) and cloned into pCV after digestion with Age I and Afl II (New England Biolabs) or with Pin AI (isoschizomer of Age I) and Bfr I (isoschizomer of Afl II) (Boehringer Mannheim). Large scale preparations of the plasmids containing full-length cDNA of H77 were performed as described above.

Construction of H77Consensus Chimeric cDNA Clone

A full-length cDNA clone of H77 with an ORF encoding the consensus amino acid sequence was constructed by making a chimera from four of the cDNA clones obtained above. This consensus chimera, pCV-H77C, was constructed in two ligation steps by using standard molecular procedures and convenient cleavage sites and involved first a two piece ligation and then a three piece ligation. Large scale preparation of pCV-H77C was performed as already described.

In Vitro Transcription

Plasmids containing the full-length HCV cDNA were linearized with Xba I (from Promega), and purified by phenol/chloroform extraction and ethanol precipitation. A 100 μl reaction mixture containing 10 μg of linearized plasmid DNA, 1× transcription buffer, 1 mM ATP, CTP, GTP and UTP, 10 mM DTT, 4% (v/v) RNasin (20–40 units/μl) and 2 μl of T7 RNA polymerase (Promega) was incubated at 3° C. for 2 hrs. Five μl of the reaction mixture was analyzed by agarose gel electrophoresis followed by ethidium bromide staining. The transcription reaction mixture was diluted with 400 μl of ice-cold phosphate-buffered saline without calcium or magnesium, immediately frozen on dry ice and stored at −8° C. The final nucleic acid mixture was injected into chimpanzees within 24 hrs.

Intrahepatic Transfection of Chimpanzees

Laparotomy was performed and aliquots from two transcription reactions were injected into 6 sites of the exposed liver (Emerson et al (1992). Serum samples were collected weekly from chimpanzees and monitored for liver enzyme levels and anti-HCV antibodies. Weekly samples of 100 μl of serum were tested for HCV RNA in a highly sensitive nested RT-PCR assay with AmpliTaq Gold (Perkin Elmer) (Yanagi et al (1996); Bukh et al (1992)). The genome titer of HCV was estimated by testing 10-fold serial dilutions of the extracted RNA in the RT-PCR assay (Yanagi et al (1996)). The two chimpanzees used in this study were maintained under conditions that met all requirements for their use in an approved facility.

The consensus sequence of the complete ORF from HCV genomes recovered at week 2 post inoculation (p.i) was determined by direct sequencing of PCR products obtained in long RT-PCR with primers A1 and H9417R followed by nested PCR of 10 overlapping fragments. The consensus sequence of the variable region of the 3' UTR was determined by direct sequencing of an amplicon obtained in nested RT-PCR as described above. Finally, we amplified selected regions independently by nested RT-PCR with AmpliTaq Gold.

Sequence Analysis

Both strands of DNA from PCR products, as well as plasmids, were sequenced with the ABI PRISM Dye Termination Cycle Sequencing Ready Reaction Kit using Taq DNA polymerase (Perkin Elmer) and about 100 specific sense and antisense sequence primers.

The consensus sequence of HCV strain H77 was determined in two different ways. In one approach, overlapping PCR products were directly sequenced, and amplified in nested RT-PCR from the H77 plasma sample. The sequence analyzed (nucleotides (nts) 35–9417) included the entire genome except the very 5' and 3' termini. In the second approach, the consensus sequence of nts 157–9384 was deduced from the sequences of 18 full-length cDNA clones.

Example 1

Variability in the Sequence of the 3' UTR of HCV Strain H77

The heterogeneity of the 3' UTR was analyzed by cloning and sequencing of DNA amplicons obtained in nested RT-PCR. 19 clones containing sequences of the entire variable region, the poly U-UC region and the adjacent 19 nt of the conserved region, and 65 clones containing sequences of the entire poly U-UC region and the first 63 nts of the conserved region were analyzed. This analysis confirmed that the variable region consisted of 43 nts, including two conserved termination codons (Han et al (1992)). The sequence of the variable region was highly conserved within H77 since only 3 point mutations were found among the 19 clones analyzed. A poly U-UC region was present in all 84 clones analyzed. However, its length varied from 71–141 nts. The length of the poly U region was 9–103 nts, and that of the poly UC region was 35–85 nts. The number of C residues increased towards the 3' end of the poly UC region but the sequence of this region is not conserved. The first 63 nts of the conserved region were highly conserved among the clones analyzed, with a total of only 14 point mutations. To confirm the validity of the analysis, the 3' UTR was reamplified directly from a full-length cDNA clone of HCV (see below) by the nested-PCR procedure with the primers in the variable region and at the very 3' end of the HCV genome and cloned the PCR product. Eight clones had 1–7 nt deletions in the poly U region. Furthermore, although the C residues of the poly UC region were maintained, the spacing of these varied because of 1–2 nt deletions of U residues. These deletions must be artifacts introduced by PCR and such mistakes may have contributed to the heterogeneity originally observed in this region. However, the conserved region of the 3' UTR was amplified correctly, suggesting that the deletions were due to difficulties in transcribing a highly repetitive sequence.

One of the 3' UTR clones was selected for engineering of full-length cDNA clones of H77. This clone had the consensus variable sequence except for a single point mutation introduced to create an Afl II cleavage site, a poly U-UC stretch of 81 nts with the most commonly observed UC pattern and the consensus sequence of the complete conserved region of 101 nts, including the distal 38 nts which originated from the antisense primer used in the amplification. After linearization with Xba I, the DNA template of this clone had the authentic 3' end.

Example 2

The Entire Open Reading Frame of H77 Amplified in One Round of Long RT-PCR

Figure 2:
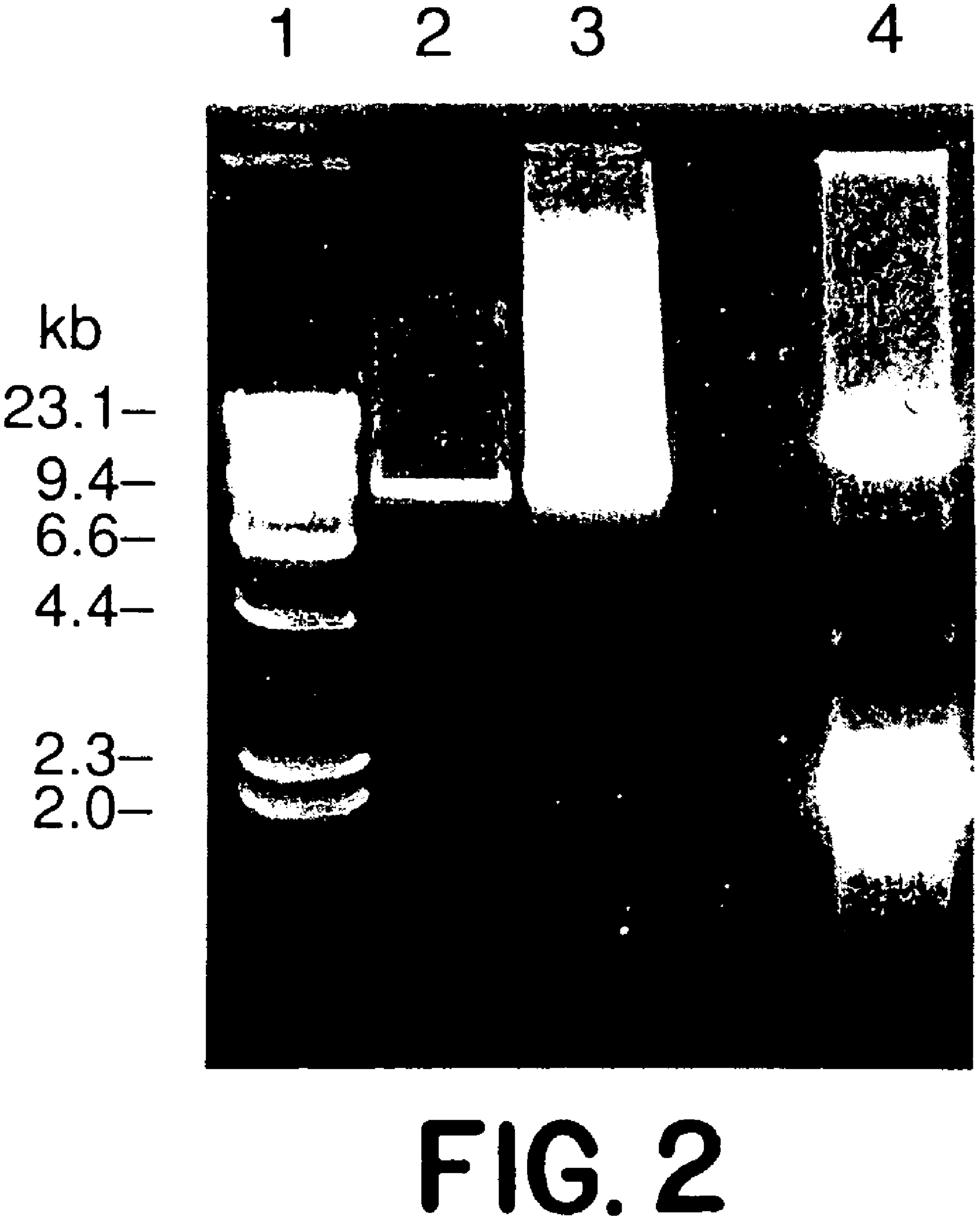
FIG. 2 shows the results of gel electrophoresis of long RT-PCR amplicons of the entire ORF of H77 and the transcription mixture of the infectious clone of H77. The complete ORF was amplified by long RT-PCR with the primers H1 or A1 and H9417R from $10^5$ GE of H77. A total of 10 μg of the consensus chimeric clone (pCV-H77C) linearized with Xba I was transcribed in a 100 μl reaction with T7 RNA polymerase. Five μl of the transcription mixture was analyzed by gel electrophoresis and the remainder of the mixture was injected into a chimpanzee. Lane 1, molecular weight marker; lane 2, products amplified with primers H1 and H9417R; lane 3, products amplified with primers A1 and H9417R; lane 4, transcription mixture containing the RNA transcripts and linearized clone pCV-H77C (12.5 kb).

It had been previously demonstrated that a 9.25 kb fragment of the HCV genome from the 5' UTR to the 3' end of NS5B could be amplified from $10^4$ GE (genome equivalents) of H77 by a single round of long RT-PCR (Tellier et al (1996a)). In the current study, by optimizing primers and cycling conditions, the entire ORF of H77 was amplified in a single round of long RT-PCR with primers from the 5' UTR and the variable region of the 3' UTR. In fact, 9.4 kb of the H77 genome (H product: from the very 5' end to the variable region of the 3' UTR) could be amplified from $10^5$ GE or 9.3 kb (A product: from within the 5' UTR to the variable region of the 3' UTR) from $10^4$ GE or $10^5$ GE, in a single round of long RT-PCR (FIG. 2). The PCR products amplified from $10^5$ GE of H77 were used for engineering full-length cDNA clones (see below).

Example 3

Construction of Multiple Full-Length cDNA Clones of H77 in a Single Step by Cloning of Long RT-PCR Amplicons Directly into a Cassette Vector with Fixed 5' and 3' Termini Direct cloning of the long PCR products (H), which contained a 5' T7 promoter, the authentic 5' end, the entire ORF of H77 and a short region of the 3' UTR, into pGEM-9zf(−) vector by Not I and Xba I digestion was first attempted. However, among the 70 clones examined all but two had inserts that were shorter than predicted. Sequence analysis identified a second Not I site in the majority of clones, which resulted in deletion of the nts past position 9221. Only two clones ($pH21_1$ and $pH50_1$) were missing the second Not I site and had the expected 5' and 3' sequences of the PCR product. Therefore, full-length cDNA clones (pH21 and pH50) were constructed by inserting the chosen 3' UTR into $pH21_1$ and $pH50_1$, respectively. Sequence analysis revealed that clone pH21 had a complete full-length sequence of H77; this clone was tested for infectivity. The second clone, pH50, had one nt deletion in the ORF at position 6365; this clone was used to make a cassette vector.

The complete ORF was amplified by constructing a cassette vector with fixed 5' and 3' termini as an intermediate of the full-length cDNA clones. This vector (pCV) was constructed by digestion of clone pH50 with BamHI, followed by religation, to give a shortened plasmid readily distinguished from plasmids containing the full-length insert. Attempts to clone long RT-PCR products (H) into pCV by Age I and Afl II yielded only 1 of 23 clones with an insert of the expected size. In order to increase the efficiency of cloning, we repeated the procedure but used Pin A I and Bfr I instead of the respective isoschizomers Age I and Afl II. By this protocol, 24 of 31 H clones and 30 of 35 A clones had the full-length cDNA of H77 as evaluated by restriction enzyme digestion. A total of 16 clones, selected at random, were each retransformed, and individual plasmids were purified and completely sequenced.

Example 4

Demonstration of Infectious Nature of Transcripts of a cDNA Clone Representing the Consensus Sequence of Strain H77

Figure 3:
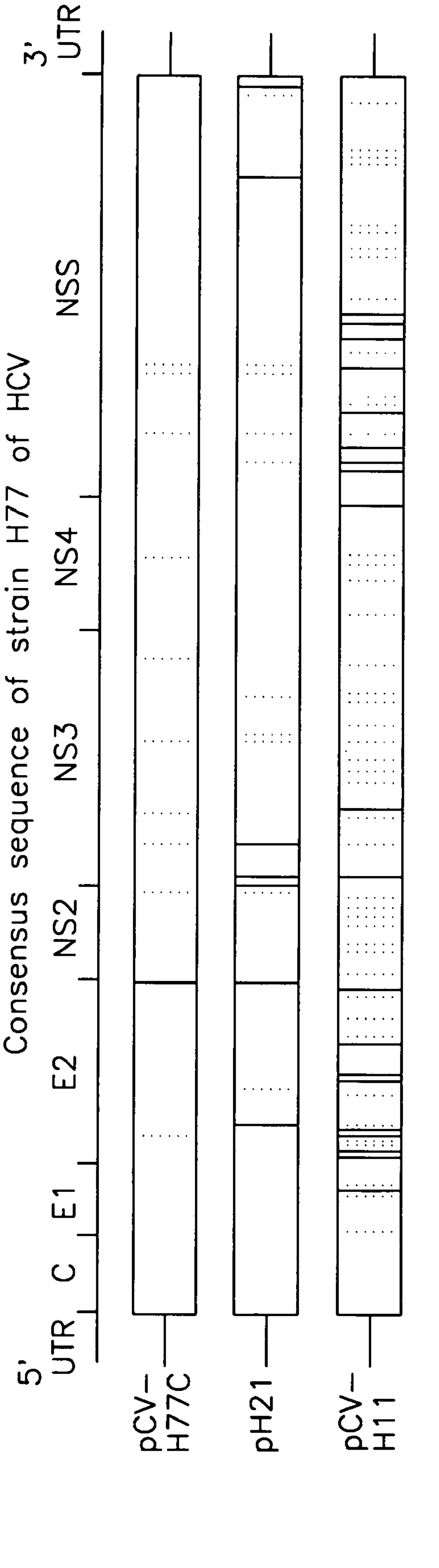
FIG. 3 is a diagram of the genome organization of HCV strain H77 and the genetic heterogeneity of individual full-length clones compared with the consensus sequence of H77. Solid lines represent aa changes. Dashed lines represent silent mutations. A * in pH21 represents a point mutation at nt 58 in the 5' UTR. In the ORF, the consensus chimeric clone pCV-H77C had 11 nt differences [at positions 1625 (C→T), 2709 (T→C), 3380 (A→G), 3710 (C→T), 3914 (G→A), 4463 (T→C), 5058 (C→T), 5834 (C→T), 6734 (T→C), 7154 (C→T), and 7202 (T→C)] and one aa change (F→L at aa 790) compared with the consensus sequence of H77. This clone was infectious. Clone pH21 and pCV-H11 had 19 nts (7 aa) and 64 nts (21 aa) differences respectively, compared with the consensus sequence of H77. These two clones were not infectious. A single point mutation in the 3' UTR at nucleotide 9406 (G→A) introduced to create an Afl II cleavage site is not shown.

A consensus chimera was constructed from 4 of the full-length cDNA clones with just 2 ligation steps. The final construct, pCV-H77C, had 11 nt differences from the consensus sequence of H77 in the ORF (FIG. 3). However, 10 of these nucleotide differences represented silent mutations. The chimeric clone differed from the consensus sequence at only one amino acid [L instead of F at position 790]. Among the 18 ORFs analyzed above, the F residue was found in 11 clones and the L residue in 7 clones. However, the L residue was dominant in other isolates of genotype 1a, including a first passage of H77 in a chimpanzee (Inchauspe et al (1991)).

To test the infectivity of the consensus chimeric clone of H77 intrahepatic transfection of a chimpanzee was performed. The pCV-H77C clone was linearized with Xba I and transcribed in vitro by T7 RNA polymerase (FIG. 2). The transcription mixture was next injected into 6 sites of the liver of chimpanzee 1530. The chimpanzee became infected with HCV as measured by detection of $10^2$ GE/ml of viral genome at week 1 p.i. Furthermore, the HCV titer increased to $10^4$ GE/ml at week 2 p.i., and reached $10^6$ GE/ml by week 8 p.i. The viremic pattern observed in the early phase of the infection with the recombinant virus was similar to that observed in chimpanzees inoculated intravenously with strain H77 or other strains of HCV (Shimizu (1990)).

The sequence of the HCV genomes from the serum sample collected at week 2 p.i. was analyzed. The consensus sequence of nts 298–9375 of the recovered genomes was determined by direct sequencing of PCR products obtained in long RT-PCR followed by nested PCR of 10 overlapping fragments. The identity to clone pCV-H77C sequence was 100%. The consensus sequence of nts 96–291, 1328–1848, 3585–4106, 4763–5113 and 9322–9445 was determined from PCR products obtained in different nested RT-PCR assays. The identity of these sequences with pCV-H77C was also 100%. These latter regions contained 4 mutations unique to the consensus chimera, including the artificial Afl II cleavage site in the 3' UTR. Therefore, RNA transcripts of this clone of HCV were infectious.

The infectious nature of the consensus chimera indicates that the regions of the 5' and 3' UTRs incorporated into the cassette vector do not destroy viability. This makes it highly advantageous to use the cassette vector to construct infectious cDNA clones of a other HCV strains when the consensus sequence for each ORF is inserted.

In addition, two complete full-length clones (dubbed pH21 and pCV-H11) constructed were not infectious, as shown by intrahepatic injection of chimpanzees with the corresponding RNA transcripts. Thus, injection of the transcription mixture into 3 sites of the exposed liver resulted in no observable HCV replication and weekly serum samples were negative for HCV RNA at weeks 1–17 p.i. in a highly sensitive nested RT-PCR assay. The cDNA template injected along with the RNA transcripts was also not detected in this assay.

Moreover, the chimpanzee remained negative for antibodies to HCV throughout the follow-up. Subsequent sequence analysis revealed that 7 of 16 additional clones were defective for polyprotein synthesis and all clones had multiple amino acid mutations compared with the consensus sequence of the parent strain. For example, clone pH21, which was not infectious, had 7 amino acid substitutions in the entire predicted polyprotein compared with the consensus sequence of H77 (FIG. 3). The most notable mutation was at position 1026, which changed L to Q, altering the cleavage site between NS2 and NS3 (Reed (1995)). Clone pCV-H11, also non-infectious, had 21 amino acid substitutions in the predicted polyprotein compared with the consensus sequence of H77 (FIG. 3). The amino acid mutation at position 564 eliminated a highly conserved C residue in the E2 protein (Okamoto (1992a)).

Example 4A

The chimpanzee of Example 4, designated 1530, was monitored out to 32 weeks p.i. for serum enzyme levels (ALT) and the presence of anti-HCV antibodies, HCV RNA, and liver histopathology. The results are shown in FIG. 18B.

A second chimp, designated 1494, was also transfected with RNA transcripts of the pCV-H77C clone and monitored out to 17 weeks p.i. for the presence of anti-HCV antibodies, HCV RNA and elevated serum enzyme levels. The results are shown in FIG. 18A.

Materials and Methods for Examples 5–10

Source Of HCV Genotype 1b

An infectious plasma pool (second chimpanzee passage) containing strain HC-J4, genotype 1b, was prepared from acute phase plasma of a chimpanzee experimentally infected with serum containing HC-J4/91 (Okamoto et al., 1992b). The HC-J4/91 sample was obtained from a first chimpanzee passage during the chronic phase of hepatitis C about 8 years after experimental infection. The consensus sequence of the entire genome, except for the very 3' end, was determined previously for HC-J4/91 (Okamoto et al., 1992b).

Preparation Of HCV RNA

Viral RNA was extracted from 100 µl aliquots of the HC-J4 plasma pool with the TRIzol system (GIBCO BRL).

The RNA pellets were each resuspended in 10 μl of 10 mM dithiothreitol (DTT) with 5% (vol/vol) RNasin (20–40 units/μl) (Promega) and stored at −8° C. or immediately used for cDNA synthesis.

Amplification and Cloning of the 3' UTR

A region spanning from NS5B to the conserved region of the 3' UTR was amplified in nested RT-PCR using the procedure of Yanagi et al., (1997).

In brief, the RNA was denatured at 65° C. for 2 minutes, and cDNA was synthesized at 42° C. for 1 hour with Superscript II reverse transcriptase (GIBCO BRL) and primer H3X58R (Table 1) in a 20 μl reaction volume. The cDNA mixture was treated with RNase H and RNase T1 (GIBCO BRL) at 37° C. for 20 minutes. The first round of PCR was performed on 2 μl of the final cDNA mixture in a total volume of 50 μl with the Advantage cDNA polymerase mix (Clontech) and external primers H9261F (Table 1) and H3'X58R (Table 1). In the second round of PCR [internal primers H9282F (Table 1) and H3'X45R (Table 1)], 5 μl of the first round PCR mixture was added to 45 μl of the PCR reaction mixture. Each round of PCR (35 cycles), was performed in a DNA thermal cycler 480 (Perkin Elmer) and consisted of denaturation at 94° C. for 1 minute (1st cycle: 1 minute 30 sec), annealing at 60° C. for 1 minute and elongation at 68° C. for 2 minutes. After purification with QIAquick PCR purification kit (QIAGEN), digestion with HindIII and XbaI (Promega), and phenol/chloroform extraction, the amplified products were cloned into pGEM-9zf(−) (Promega) (Yanagi et al., 1997).

Amplification and Cloning of the Entire ORF

A region from within the 5' UTR to the variable region of the 3' UTR of strain HC-J4 was amplified by long RT-PCR (FIG. 1) (Yanagi et al., 1997). The cDNA was synthesized at 42° C. for 1 hour in a 20 μl reaction volume with Superscript II reverse transcriptase and primer J4-9405R (5'-GCCTATTGGCCTGGAGTGGTTAGCTC-3') SEQ ID NO:18, and treated with RNases as above. The cDNA mixture (2 μl) was amplified by long PCR with the Advantage cDNA polymerase mix and primers A1 (Table 1) (Bukh et al., 1992; Yanagi et al., 1997) and J4-9398R (5'AGGATGGC <u>CTTAAG</u>GCCTGGAGTGGTTAGCTCCCCGTTCA-3') NO:19. Primer J4-9398R contained extra bases (bold) and an artificial AflII cleavage site (underlined). A single PCR round was performed in a Robocycler thermal cycler (Stratagene), and consisted of denaturation at 99° C. for 35 seconds, annealing at 6° C. for 30 seconds and elongation at 68° C. for 10 minutes during the first 5 cycles, 11 minutes during the next 10 cycles, 12 minutes during the following 10 cycles and 13 minutes during the last 10 cycles.

Figure 6:
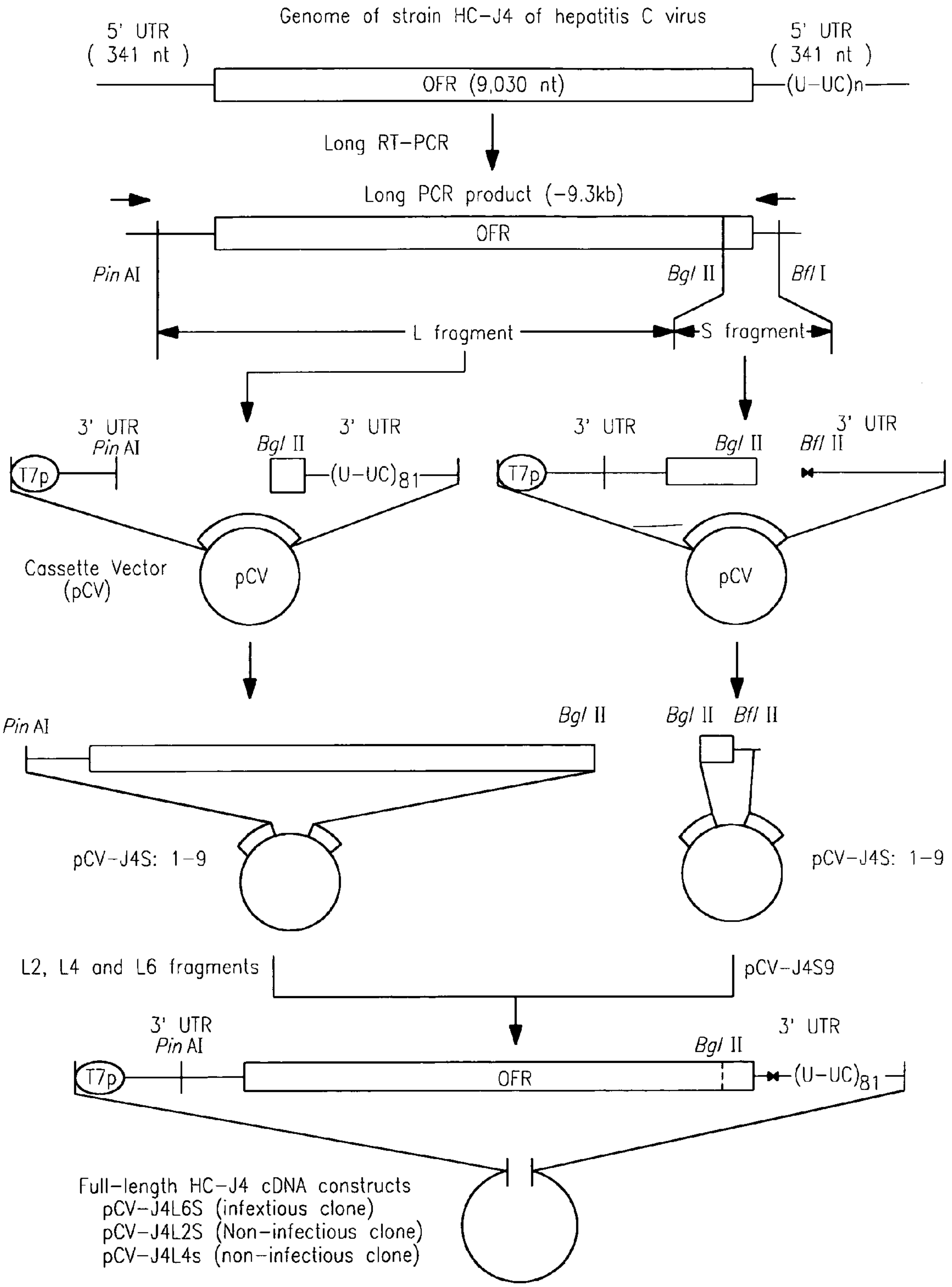
FIG. 6 shows the strategy utilized for the construction of full-length cDNA clones of HCV strain HC-J4. The long PCR products were cloned as two separate fragments (L and S) into a cassette vector (pCV) with fixed 5' and 3' termini of HCV (Yanagi et al., 1997). Full-length cDNA clones of HC-J4 were obtained by inserting the L fragment from three pCV-J4L clones into three identical pCV-J4S9 clones after digestion with PinAI (isoschizomer of AgeI) and BfrI (isoschizomer of AflII).

After digesting the long PCR products obtained from strain HC-J4 with PinAI (isoschizomer of AgeI) and BfrI (isoschizomer of AflII) (Boehringer Mannheim), attempts were made to clone them directly into a cassette vector (pCV), which contained the 5' and 3' termini of strain H77 (FIG. 1) but no full-length clones were obtained. Accordingly, to improve the efficiency of cloning, the PCR product was further digested with BglII (Boehringer Mannheim) and the two resultant genome fragments [L fragment: PinAI/BglII, nts 156–8935; S fragment: BglII/BrfI, nts 8936–9398] were separately cloned into pCV (FIG. 6).

DH5α competent cells (GIBCO BRL) were transformed and selected on LB agar plates containing 100 μg/ml ampicillin (SIGMA) and amplified in LB liquid cultures at 30° C. for 18–20 hours.

Sequence analysis of 9 plasmids containing the S fragment (miniprep samples) and 9 plasmids containing the L fragment (maxiprep samples) were performed as described previously (Yanagi et al., 1997). Three L fragments, each encoding a distinct polypeptide, were cloned into pCV-J4S9 (which contained an S fragment encoding the consensus amino acid sequence of HC-J4) to construct three chimeric full-length HCV cDNAs (pCV-J4L2S, pCV-J4L4S and pCV-J4L6S) (FIG. 6). Large scale preparation of each clone was performed as described previously with a QIAGEN plasmid Maxi kit (Yanagi et al., 1997) and the authenticity of each clone was confirmed by sequence analysis.

Sequence Analysis

Both strands of DNA were sequenced with the ABI PRISM Dye Termination Cycle Sequencing Ready Reaction Kit using Taq DNA polymerase (Perkin Elmer) and about 90 specific sense and antisense primers. Analyses of genomic sequences, including multiple sequence alignments and tree analyses, were performed with GeneWorks (Oxford Molecular Group) (Bukh et al., 1995).

The consensus sequence of strain HC-J4 was determined by direct sequencing of PCR products (nts 11–9412) and by sequence analysis of multiple cloned L and S fragments (nts 156–9371). The consensus sequence of the 3' UTR (3' variable region, polypyrimidine tract and the first 16 nucleotides of the conserved region) was determined by analysis of 24 cDNA clones.

Intrahepatic Transfection of a Chimpanzee with Transcribed RNA

Figure 5:
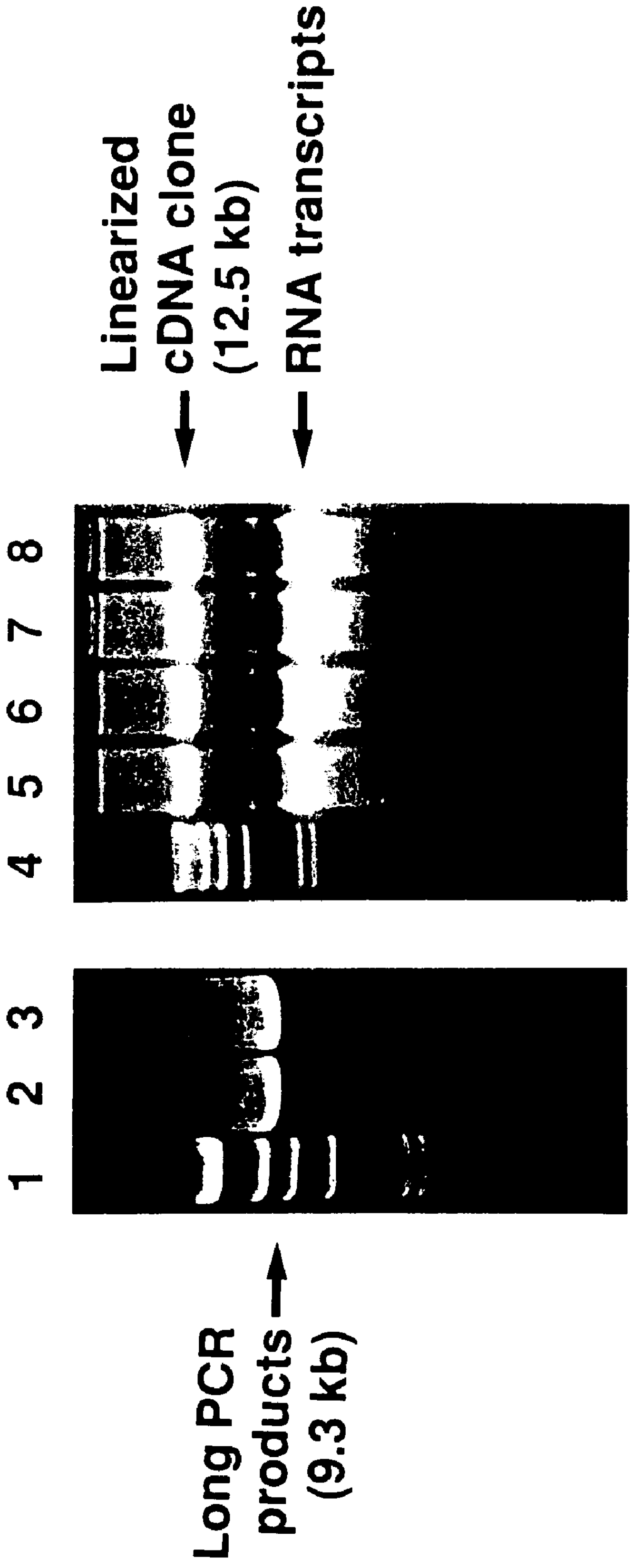
FIG. 5 shows an agarose gel of long RT-PCR amplicons and transcription mixtures. Lanes 1 and 4: Molecular weight marker (Lambda/HindIII digest). Lanes 2 and 3: RT-PCR amplicons of the entire ORF of HC-J4. Lane 5: pCV-H77C transcription control (Yanagi et al., 1997). Lanes 6, 7, and 8: 1/40 of each transcription mixture of pCV-J4L2S, pCV-J4L4S and pCV-J4L6S, respectively, which was injected into the chimpanzee.

Two in vitro transcription reactions were performed with each of the three full-length clones. In each reaction 10 μg of plasmid DNA linearized with Xba I (Promega) was transcribed in a 100 μl reaction volume with T7 RNA polymerase (Promega) at 37° C. for 2 hours as described previously (Yanagi et al., 1997). Five μl of the final reaction mixture was analyzed by agarose gel electrophoresis and ethidium bromide staining (FIG. 5). Each transcription mixture was diluted with 400 μl of ice-cold phosphate-buffered saline without calcium or magnesium and then the two aliquots from the same cDNA clone were combined, immediately frozen on dry ice and stored at −80° C. Within 24 hours after freezing the transcription mixtures were injected into the chimpanzee by percutaneous intrahepatic injection that was guided by ultrasound. Each inoculum was individually injected (5–6 sites) into a separate area of the liver to prevent complementation or recombination. The chimpanzee was maintained under conditions that met all requirements for its use in an approved facility.

Serum samples were collected weekly from the chimpanzee and monitored for liver enzyme levels and anti-HCV antibodies. Weekly samples of 100 μl of serum were tested for HCV RNA in a sensitive nested RT-PCR assay (Bukh et al., 1992, Yanagi et al., 1996) with AmpliTaq Gold DNA polymerase. The genome equivalent (GE) titer of HCV was determined by testing 10-fold serial dilutions of the extracted RNA in the RT-PCR assay (Yanagi et al., 1996) with 1 GE defined as the number of HCV genomes present in the highest dilution which was positive in the RT-nested PCR assay.

To identify which of the three clones was infectious in vivo, the NS3 region (nts 3659–4110) from the chimpanzee serum was amplified in a highly sensitive and specific nested RT-PCR assay with AmpliTaq Gold DNA polymerase and the PCR products were cloned with a TA cloning kit (Invitrogen). In addition, the consensus sequence of the nearly complete genome (nts 11–9441) was determined by direct sequencing of overlapping PCR products.

Example 5

Sequence Analysis of Infectious Plasma Pool of Strain HC-J4 Used as the Cloning Source As an infectious cDNA clone of a genotype 1a strain of HCV had been obtained only after the ORF was engineered to encode the consensus polypeptide (Kolykhalov et al., 1997; Yanagi et al., 1997), a detailed sequence analysis of the cloning source was performed to determine the consensus sequence prior to constructing an infectious cDNA clone of a 1b genotype.

A plasma pool of strain HC-J4 was prepared from acute phase plasmapheresis units collected from a chimpanzee experimentally infected with HC-J4/91 (Okamoto et al., 1992b). This HCV pool had a PCR titer of $10^4$–$10^5$ GE/ml and an infectivity titer of approximately $10^3$ chimpanzee infectious doses per ml.

The heterogeneity of the 3' UTR of strain HC-J4 was determined by analyzing 24 clones of nested RT-PCR product. The consensus sequence was identical to that previously published for HC-J4/91 (Okamoto et al., 1992b), except at position 9407 (see below). The variable region consisted of 41 nucleotides (nts. 9372–9412), including two in-frame termination codons. Furthermore, its sequence was highly conserved except at positions 9399 (19 A and 5 T clones) and 9407 (17 T and 7 A clones). The poly U-UC region varied slightly in composition and greatly in length (31–162 nucleotides). In the conserved region, the first 16 nucleotides of 22 clones were identical to those previously published for other genotype 1 strains, whereas two clones each had a single point mutation. These data suggested that the structural organization at the 3' end of HC-J4 was similar to that of the infectious clone of a genotype 1a strain of Yanagi et al (1997).

Next, the entire ORF of HC-J4 was amplified in a single round of long RT-PCR (FIG. 5). The original plan was to clone the resulting PCR products into the PinAI and BrfI site of a HCV cassette vector (pCV), which had fixed 5' and 3' termini of genotype 1a (Yanagi et al., 1997) but since full-length clones were not obtained, two genome fragments (L and S) derived from the long RT-PCR products (FIG. 6) were separately subcloned into pCV.

To determine the consensus sequence of the ORF, the sequence of 9 clones each of the L fragment (pCV-J4L) and of the S fragment (pCV-J4S) was determined and quasispecies were found at 275 nucleotide (3.05%) and 78 amino acid (2.59%) positions, scattered throughout the 9030 nts (3010 aa) of the ORF (FIG. 7). Of the 161 nucleotide substitutions unique to a single clone, 71% were at the third position of the codon and 72% were silent.

Figure 9:
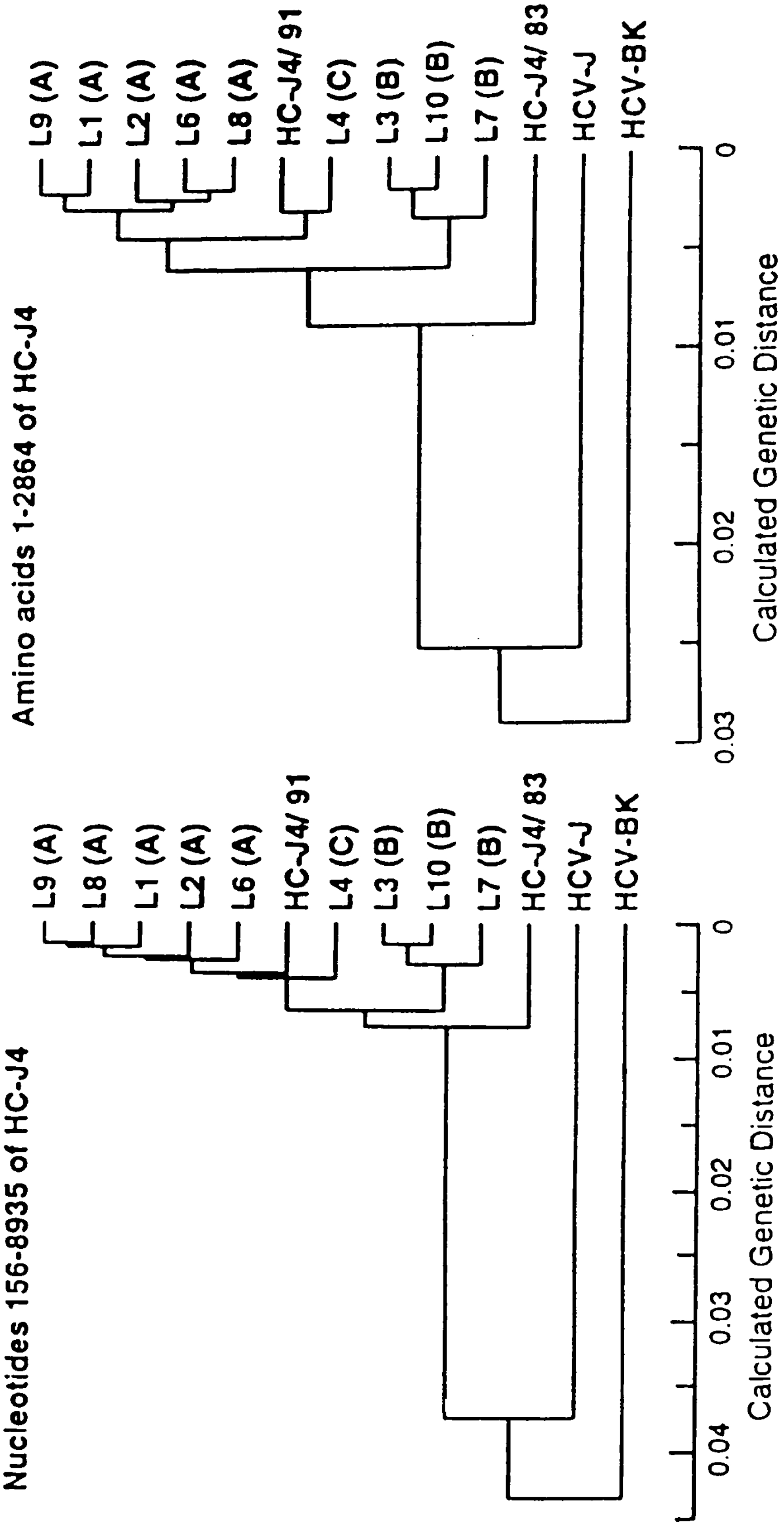
FIG. 9 shows UPGMA ("unweighted pair group method with arithmetic mean") trees of HC-J4/91 (Okamoto et al., 1992b), HC-J4/83 (Okamoto et al., 1992b), two prototype strains of genotype 1b (HCV-J, Kato et al., 1990; HCV-BK, Takamizawa et al., 1991), and L clones (this study)

Each of the nine L clones represented the near complete ORF of an individual genome. The differences among the L clones were 0.30–1.53% at the nucleotide and 0.31–1.47% at the amino acid level (FIG. 8). Two clones, L1 and L7, had a defective ORF due to a single nucleotide deletion and a single nucleotide insertion, respectively. Even though the HC-J4 plasma pool was obtained in the early acute phase, it appeared to contain at least three viral species (FIG. 9). Species A contained the L1, L2, L6, L8 and L9 clones, species B the L3, L7 and L10 clones and species C the L4 clone. Although each species A clone was unique all A clones differed from all B clones at the same 20 amino acid sites and at these positions, species C had the species A sequence at 14 positions and the species B sequence at 6 positions (FIG. 7).

Okamoto and coworkers (Okamoto et al., 1992b) previously determined the nearly complete genome consensus sequence of strain HC-J4 in acute phase serum of the first chimpanzee passage (HC-J4/83) as well as in chronic phase serum collected 8.2 years later (HC-J4/91). In addition, they determined the sequence of amino acids 379 to 413 (including HVR1) and amino acids 468 to 486 (including HVR2) of multiple individual clones (Okamoto et al., 1992b).

It was found by the present inventors that the sequences of individual genomes in the plasma pool collected from a chimpanzee inoculated with HC-J4/91 were all more closely related to HC-J4/91 than to HC-J4/83 (FIGS. 8, 9) and contained HVR amino acid sequences closely related to three of the four viral species previously found in HC-J4/91 (FIG. 10).

Thus, the data presented herein demonstrate the occurrence of the simultaneous transmission of multiple species to a single chimpanzee and clearly illustrates the difficulties in accurately determining the evolution of HCV over time since multiple species with significant changes throughout the HCV genome can be present from the onset of the infection. Accordingly, infection of chimpanzees with monoclonal viruses derived from the infectious clones described herein will make it possible to perform more detailed studies of the evolution of HCV in vivo and its importance for viral persistence and pathogenesis.

Example 6

Determination of the Consensus Sequence of HC-J4 in the Plasma Pool

The consensus sequence of nucleotides 156–9371 of HC-J4 was determined by two approaches. In one approach, the consensus sequence was deduced from 9 clones of the long RT-PCR product. In the other approach the long RT-PCR product was reamplified by PCR as overlapping fragments which were sequenced directly. The two "consensus" sequences differed at 31 (0.34k) of 9216 nucleotide positions and at 11 (0.37%) of 3010 deduced amino acid positions (FIG. 7). At all of these positions a major quasispecies of strain HC-J4 was found in the plasma pool. At 9 additional amino acid positions the cloned sequences displayed heterogeneity and the direct sequence was ambiguous (FIG. 7). Finally, it should be noted that there were multiple amino acid positions at which the consensus sequence obtained by direct sequencing was identical to that obtained by cloning and sequencing even though a major quasispecies was detected (FIG. 7).

For positions at which the two "consensus" sequences of HC-J4 differed, both amino acids were included in a composite consensus sequence (FIG. 7). However, even with this allowance, none of the 9 L clones analyzed (aa 1–2864) had the composite consensus sequence: two clones did not encode the complete polypeptide and the remaining 7 clones differed from the consensus sequence by 3–13 amino acids (FIG. 7).

Example 7

Construction of Chimeric Full-Length cDNA Clones Containing the Entire ORF Of HC-J4

The cassette vector used to clone strain H77 was used to construct an infectious cDNA clone containing the ORF of a second subtype.

In brief, three full-length cDNA clones were constructed by cloning different L fragments into the PinAI/BglII site of pCV-J4S9, the cassette vector for genotype 1a (FIG. 6), which also contained an S fragment encoding the consensus amino acid sequence of HC-J4. Therefore, although the ORF was from strain HC-J4, most of the 5' and 3' terminal sequences originated from strain H77. As a result, the 5' and 3' UTR were chimeras of genotypes 1a and 1b (FIG. 11).

The first 155 nucleotides of the 5' UTR were from strain H77 (genotype 1a), and differed from the authentic sequence of HC-J4 (genotype 1b) at nucleotides 11, 12, 13, 34 and 35. In two clones (pCV-J4L2S, pCV-J4L6S) the rest of the 5' UTR had the consensus sequence of HC-J4, whereas the third clone (pCV-J4L4S) had a single nucleotide insertion at position 207. In all 3 clones the first 27 nucleotides of the 3' variable region of the 3' UTR were identical with the consensus sequence of HC-J4. The remaining 15 nucleotides of the variable region, the poly U-UC region and the 3' conserved region of the 3' UTR had the same sequence as an infectious clone of strain H77 (FIG. 11).

Figure 12:
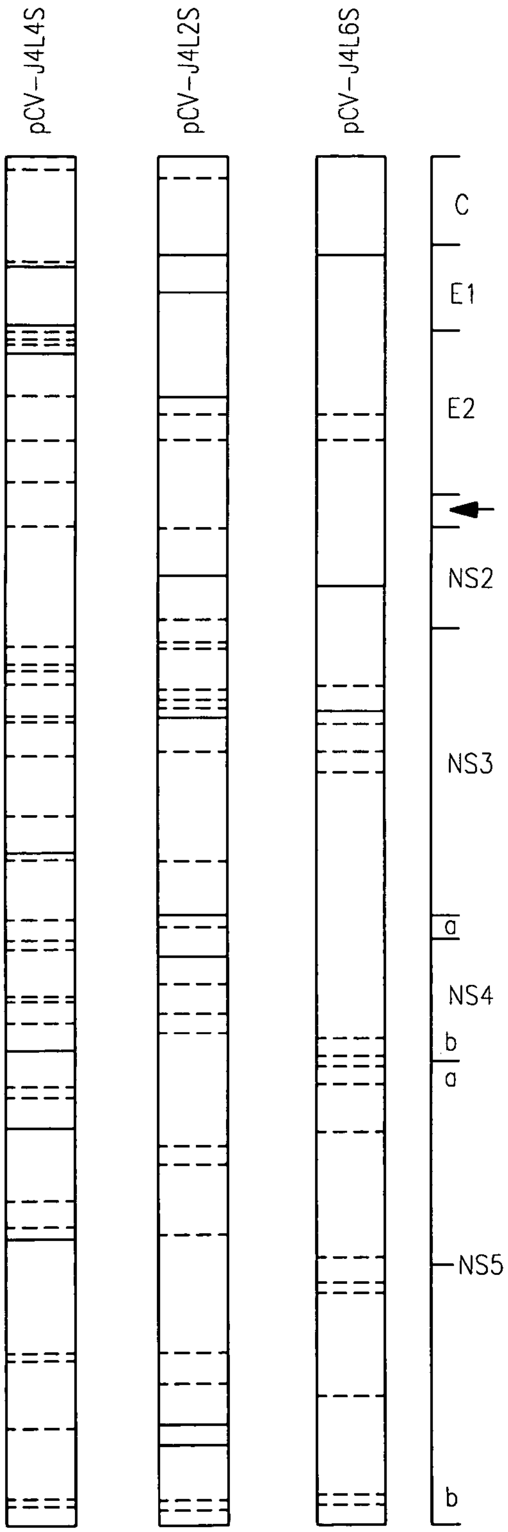
FIG. 12 shows a comparison of individual full-length cDNA clones of the ORF of HCV strain HC-J4 with the consensus sequence (see FIG. 7). Solid lines: amino acid changes. Dashed lines: silent mutations. Clone pCv-J4L6S was infectious in vivo whereas clones pCV-J4L2S and pCV-J4L4S were not.

None of the three full-length clones of HC-J4 had the ORF composite consensus sequence (FIGS. 7, 12). The pCV-J4L6S clone had only three amino acid changes: Q for R at position 231 (E1), V for A at position 937 (NS2) and T for S at position 1215 (NS3). The pCV-J4L4S clone had 7 amino acid changes, including a change at position 450 (E2) that eliminated a highly conserved N-linked glycosylation site (Okamoto et al., 1992a). Finally, the pCV-J4L2S clone had 9 amino acid changes compared with the consensus sequence of HC-J4. A change at position 304 (E1) mutated a highly conserved cysteine residue (Bukh et al., 1993; Okamoto et al., 1992a).

Example 8

Transfection of a Chimpanzee by in Vitro Transcripts of a Chimeric cDNA

The infectivity of the three chimeric HCV clones was determined by ultra-sound-guided percutaneous intrahepatic injection into the liver of a chimpanzee of the same amount of cDNA and transcription mixture for each of the clones (FIG. 5). This procedure is a less invasive procedure than the laparotomy procedure utilized by Kolykhalov et al. (1997) and Yanagi et al. (1997) and should facilitate in vivo studies of cDNA clones of HCV in chimpanzees since percutaneous procedures, unlike laparotomy, can be performed repeatedly.

Figure 13:
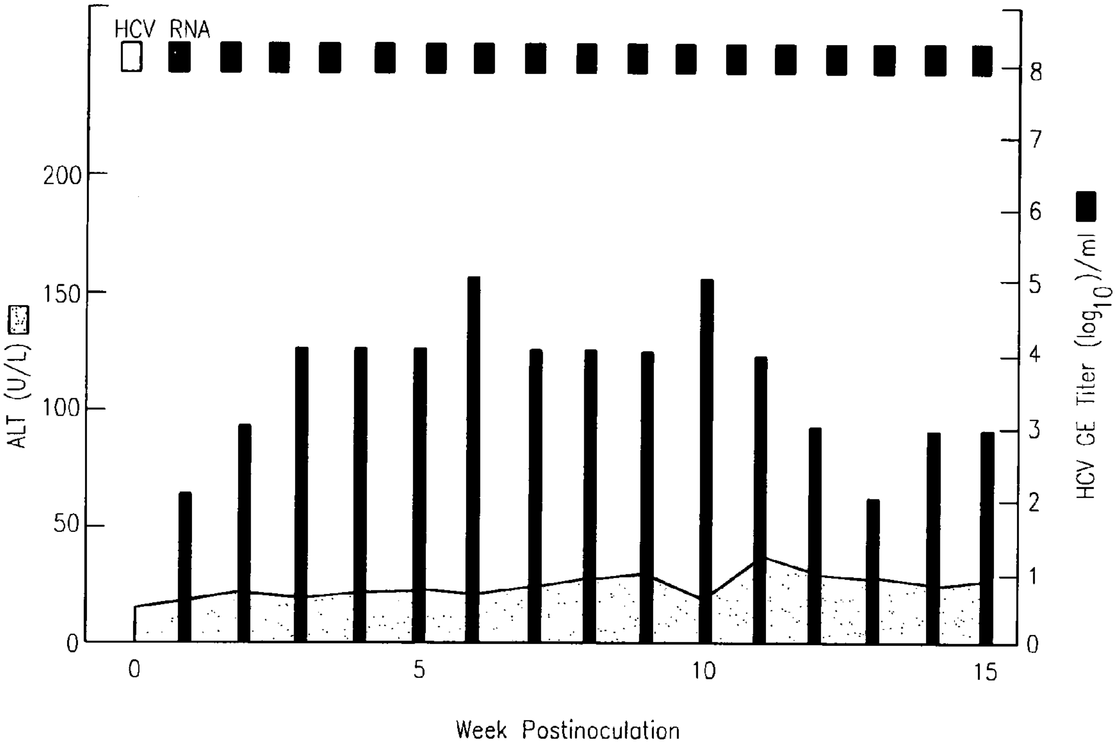
FIG. 13 shows biochemical (ALT levels) and PCR analyses of a chimpanzee following percutaneous intrahepatic transfection with RNA transcripts of the infectious clone of pCV-J4L2S, pCV-J4L4S and pCV-J4L6S. The ALT serum enzyme levels were measured in units per liter (u/l). For the PCR analysis, "HCV RNA" represented by an open rectangle indicates a serum sample that was negative for HCV after nested PCR; "HCV RNA" represented by a closed rectangle indicates that the serum sample was positive for HCV and HCV GE titer on the right-hand y-axis represents genome equivalents.

As shown in FIG. 13, the chimpanzee became infected with HCV as measured by increasing titers of $10^2$ GE/ml at week 1 p.i., $10^3$ GE/ml at week 2 p.i. and $10^4$–$10^5$ GE/ml during weeks 3 to 10 p.i.

The viremic pattern found in the early phase of the infection was similar to that observed for the recombinant H77 virus in chimpanzees (Bukh et al., unpublished data; Kolykhalov et al., 1997; Yanagi et al., 1997). The chimpanzee transfected in the present study was chronically infected with hepatitis G virus (HGV/GBV-C) (Bukh et al., 1998) and had a titer of $10^6$ GE/ml at the time of HCV transfection. Although HGV/GBV-C was originally believed to be a hepatitis virus, it does not cause hepatitis in chimpanzees (Bukh et al., 1998) and may not replicate in the liver (Laskus et al., 1997). The present study demonstrated that an ongoing infection of HGV/GBV-C did not prevent acute HCV infection in the chimpanzee model.

However, to identify which of the three full-length HC-J4 clones were infectious, the NS3 region (nts. 3659–4110) of HCV genomes amplified by RT-PCR from serum samples taken from the infected chimpanzee during weeks 2 and 4 post-infection (p.i.) were cloned and sequenced. As the PCR primers were a complete match with each of the original three clones, this assay should not have preferentially amplified one virus over another. Sequence analysis of 26 and 24 clones obtained at weeks 2 and 4 p.i., respectively, demonstrated that all originated from the transcripts of pCV-J4L6S.

Moreover, the consensus sequence of PCR products of the nearly complete genome (nts. 11–9441), amplified from serum obtained during week 2 p.i., was identical to the sequence of pCV-J4L6S and there was no evidence of quasispecies. Thus, RNA transcripts of pCV-J4L6S, but not of pCV-J4L2S or pCV-J4L4S, were infectious in vivo. The data in FIG. 13 is therefore the product of the transfection of RNA transcripts of pCV-J4L6S.

In addition, the chimeric sequences of genotypes 1a and 1b in the UTRs were maintained in the infected chimpanzee. The consensus sequence of nucleotides 11–341 of the 5' UTR and the variable region of the 3' UTR, amplified from serum obtained during weeks 2 and 4 p.i., had the expected chimeric sequence of genotypes 1a and 1b (FIG. 11). Also three of four clones of the 3' UTR obtained at week 2 p.i. had the chimeric sequence of the variable region, whereas a single substitution was noted in the fourth clone. However, in all four clones the poly U region was longer (2–12 nts) than expected. Also, extra C and G residues were observed in this region. For the most part, the number of C residues in the poly UC region was maintained in all clones although the spacing varied. As shown previously, variations in the number of U residues can reflect artifacts introduced during PCR amplification (Yanagi et al., 1997). The sequence of the first 19 nucleotides of the conserved region was maintained in all four clones. Thus, with the exception of the poly U-UC region, the genomic sequences recovered from the infected chimpanzee were exactly those of the chimeric infectious clone pCV-J4BL6S.

The results presented in FIG. 13 therefore demonstrate that HCV polypeptide sequences other than the consensus sequence can be infectious and that a chimeric genome containing portions of the H77 termini could produce an infectious virus. In addition, these results showed for the first time that it is possible to make infectious viruses containing 5' and 3' terminal sequences specific for two different subtypes of the same major genotype of HCV.

Example 9

Construction of a Chimeric 1a/1b Infectious Clone

A chimeric 1a/1b infectious clone in which the structural region of the genotype 1b infectious clone is inserted into the 1a clone of Yanagi et al. (1997) is constructed by following the protocol shown in FIG. 15. The resultant chimera contains nucleotides 156–2763 of the 1b clone described herein inserted into the 1a clone of FIGS. 4A–4F. The sequences of the primers shown in FIG. 15 which are used in constructing this chimeric clone, designated pH77CV-J4, are presented below.

1. H2751S (Cla I/Nde I) SEQ ID NO:20
   CGT CAT CGA TCC TCA GCG GGC ATA TGC ACT GGA CAC GGA
2. H2870R SEQ ID NO:21
   CAT GCA CCA GCT GAT ATA GCG CTT GTA ATA TG
3. H7851S SEQ ID NO:22
   TCC GTA GAG GAA GCT TGC AGC CTG ACG CCC

4. H9173 R (P-M) SEQ ID NO:23
GTA CTT GCC ACA TAT AGC AGC CCT GCC TCC TCT G
5. H9140S (P-M) SEQ ID NO:24
CAG AGG AGG CAG GGC TGC TAT ATG TGG CAA GTA C
6. H9417R SEQ ID NO:25
CGT CTC TAG ACA GGA AAT GGC TTA AGA GGC CGG AGT GTT TAC C
7. J4-2271S SEQ ID NO:26
TGC AAT TGG ACT CGA GGA GAG CGC TGT AAC TTG GAG
8. J4-2776R (Nde I) SEQ ID NO:27
CGG TCC AAG GCA TAT GCT CGT GGT GGT AAC GCC AG

Transcripts of the chimeric 1a/1b clone (whose sequence is shown in FIGS. 16A–16F) are then produced and transfected into chimpanzees by the methods described in the Materials and Methods section herein and the transfected animals are then be subjected to biochemical (ALT levels), histopathological and PCR analyses to determine the infectivity of the chimeric clone.

Example 10

Construction of 3' Deletion Mutants of the 1a Infectious Clone DCV-H77C

Seven constructs having various deletions in the 3' untranslated region (UTR) of the 1a infectious clone pCV-H77C were constructed as described in FIGS. 17A–17B. The 3' untranslated sequence remaining in each of the seven constructs following their respective deletions is shown in FIGS. 17A–17B.

Construct pCV-H77C(−98X) containing a deletion of the 3'-most 98 nucleotide sequences in the 3'-UTR was transcribed in vitro according to the methods described herein and 1 ml of the diluted transcription mixture was percutaneously transfected into the liver of a chimpanzee with the aid of ultrasound. After three weeks, the transfection was repeated. The chimpanzee was observed to be negative for hepatitis C virus replication as measured by RT-PCR assay for 5 weeks after transfection. These results demonstrate that the deleted 98 nucleotide 3'-UTR sequence was critical for production of infectious HCV and appear to contradict the reports of Dash et al. (1996) and Yoo et al. (1995) who reported that RNA transcripts from cDNA clones of HCV-1 and HCV-N lacking the terminal 98 conserved nucleotides at the very 3' end of the 3'-UTR resulted in viral replication after transfection into human hematoma cell lines.

Transcripts of the (−42X) mutant (FIG. 17C) were also produced and transfected into a chimpanzee and transcripts of the other five deletion mutants shown in FIGS. 17D–17G) are to be produced and transfected into chimpanzees by the methods described herein. All transfected animals are to then be assayed for viral replication via RT-PCR.

Discussion

In two recent reports on transfection of chimpanzees, only those clones engineered to have the independently determined and slightly different consensus amino acid sequence of the polypeptide of strain H77 were infectious (Kolykhalov et al., 1997; Yanagi et al., 1997). Although the two infectious clones differed at four amino acid positions, these differences were represented in a major component of the quasispecies of the cloning source. In the present study, a single consensus sequence of strain HC-J4 could not be defined because the consensus sequence obtained by two different approaches (direct sequencing and sequencing of cloned products) differed at 20 amino acid positions, even though the same genomic PCR product was analyzed. The infectious clone differed at two positions from the composite amino acid consensus sequence, from the sequence of the 8 additional HC-J4 clones analyzed in this study and from published sequences of earlier passage samples. An additional amino acid differed from the composite consensus sequence but was found in two other HC-J4 clones analyzed in this study. The two non-infectious full-length clones of HC-J4 differed from the composite consensus sequence by only 7 and 9 amino acid differences. However, since these clones had the same termini as the infectious clone (except for a single nucleotide insertion in the 5' UTR of pCV-J4L4S), one or more of these amino acid changes in each clone was apparently deleterious for the virus.

It was also found in the present study that HC-J4, like other strains of genotype 1b (Kolykhalov et al., 1996; Tanaka et al., 1996; Yamada et al., 1996), had a poly U-UC region followed by a terminal conserved element. The poly U-UC region appears to vary considerably so it was not clear whether changes in this region would have a significant effect on virus replication. On the other hand, the 3' 98 nucleotides of the HCV genome were previously shown to be identical among other strains of genotypes 1a and 1b (Kolykhalov et al., 1996; Tanaka et al., 1996). Thus, use of the cassette vector would not alter this region except for addition of 3 nucleotides found in strain H77 between the poly UC region and the 3' 98 conserved nucleotides.

In conclusion, an infectious clone representing a genotype 1b strain of HCV has been constructed. Thus, it has been demonstrated that it was possible to obtain an infectious clone of a second strain of HCV. In addition, it has been shown that a consensus amino acid sequence was not absolutely required for infectivity and that chimeras between the UTRs of two different genotypes could be viable.

REFERENCES

Alter, M. J. (1997). *Hepatolocy* 26, 62S–65S.
Blight, K. J. and Rice, C. M. (1997). *J. Virol.* 71, 7345–7352.
Brechot, C. (1997). *Helatolocy* 25, 772–774.
Bukh, J., et al. (1992). *Proc. Natl. Acad. Sci. USA* 89, 187–191.
Bukh, J., et al. (1993). *Proc. Natl. Acad. Sci. USA* 90, 8234–8238.
Bukh, J., et al. (1995). *Semin. Liver Dis.* 15, 41–63.
Bukh, J., et al. (1997). Genetic heterogeneity of hepatitis C virus and related viruses. In "Viral Hepatitis and Liver Disease, Proceedings of IX Triennial International Symposium on Viral Hepatitis and Liver Disease, Rome, Italy, 1996" (M. Rizzetto, R. H. Purcell, J. L. Gerin and G. Verme, Eds.), pp. 167–175. Edizioni Minerva Medica, Turin.
Bukh, J., et al. (1998). Experimental infection of chimpanzees with hepatitis G virus and genetic analysis of the virus. *J. Infect. Dis.* (in press).
Choo, Q.-L., et al. (1991). Diversity of the hepatitis C virus. Proc. Natl. Acad. Sci. USA 88, 2451–2455.
Dash, S., et al. (1997). *Am. J. Pathol.* 151, 363–373.
Emerson, S. U. et al (1992) *J. Virol.,* 66:6649–6654.
Farci, P. and Purcell, R. H. (1993). Natural history and experimental models. In "Viral Hepatitis: Scientific Basis and Clinical Management". (A. J. Zuckerman and H. C. Thomas, Eds.). pp. 241–267. Churchill Livingstone, Edinburgh.

Farci, P., et al. (1994). Prevention of hepatitis C virus infection in chimpanzees after antibody-mediated in vitro neutralization. *Proc. Natl. Acad. Sci. USA* 91, 7792–7796.

Farci, P., et al. (1996). *Proc. Natl. Acad. Sci. USA* 93, 15394–15399.

Farci, P., et al. (1997). *Springer Semin. Immunopathol.* 19, 5–26.

Fausto, N. (1997). *Am. J. Pathol.* 151, 361.

Feinstone, S. M. et al (1981) *J. Infect. Dis.* 144:588–598.

Fried, M. W. and Hoofnagle, J. H. (1995). *Semin. Liver Dis.* 15, 82–91.

Han, J. M. et al (1992) *Nuc. Acids Res.,* 20:3250.

Hijikata, M., et al. (1991). *Biochem. Biophys. Res. Commun.* 175, 220–228.

Honda, M., et al. (1996). *RNA* 2, 955–968.

Hoofnagle, J. H. (1997). *Hepatolocy* 26, 15S–20S.

Houghton, M. (1996). Hepatitis C viruses. In "Fields Virology" (B. N. Fields, D. M. Knipe, P. M. Howley, et al., Eds.), Third ed., Lippincott-Raven Publishers, Philadelphia.

Inchauspe, G. et al. (1991) *Proc. Natl. Acad. Sci. U.S.A.,* 88:10292–10296.

Ito, T. and Lai, M. M. C. (1997). *J. Virol.* 71, 8698–8706.

Kato, N., et al. (1990). *Proc. Natl. Acad. Sci. USA* 87, 9524–9528.

Kolykhalov, A. A., Feinstone, S. M. and Rice, C. M. (1996). *J. Virol.* 70, 3363–3371.

Kolykhalov, A. A., et al. (1997). *Science* 277, 570–574.

Krieg, A. M. et al. (1995) *Nature,* 374:546.

Krieg, A. M. et al. (1996) *J. Lab. Clin. Med.,* 128:128.

Laskus, T., et al. (1997). *J. Virol.* 71, 7804–7806.

Major, M. E. and Feinstone, S. M. (1997) *Heptology* 25:1527–1538.

Ogata, N. et al (1991) *Proc. Natl. Acad. Sci. U.S.A.,* 88:3392–3396.

Okamoto, H., et al. (1992a). *Virolocy* 188, 331–341.

Okamoto, H., et al. (1992b) *Virology* 190, 894–899.

Reed, K. E., et al. (1995) *J. Virol.,* 69:4127–4136.

Rice, C. M. (1996). Flaviviridae: The viruses and their replication, In "Fields Virology". (B. N. Fields, D. M. Knipe, P. M. Howley, et al., Eds.), Third ed., Lippincott-Raven Publishers, Philadelphia.

Shimizu, Y. K., et al. (1990) *Proc. Natl. Acad. Sci. U.S.A.,* 87:6441–6444.

Shimizu, Y. K., et al. (1992). *Proc. Natl. Acad. Sci. USA* 89, 5477–5481.

Shimizu, Y. K., et al. (1996). *Virology* 223, 409–412.

Simmonds, P., et al. (1993). *J. Gen. Virol.* 74, 2391–2399.

Takamizawa, A., et al. (1991). *J. Virol.* 65, 1105–1113.

Tanaka, T., et al. (1995). *Biochem. Biophys. Res. Commun.* 215, 744–749.

Tanaka, T., et al. (1996). Structure of the 3' terminus of the hepatitis C virus genome. *J. Virol.* 70, 3307–3312.

Tellier, R. et al (1996) *Proc. Natl. Acad. Sic. U.S.A.,* 93:4370–4373.

Tellier, R., et al (1996a) *J. Clin. Microbiol,* 34:3085–3091.

Tsuchihara, K., et al. *J. Virol.* 71, 6720–6726.

Tsukiyama-Kohara, K., et al. *J. Virol.* 66, 1476–1483.

What is claimed is:

1. A composition comprising a purified and isolated nucleic acid molecule, which encodes human hepatitis C virus (HCV), wherein expression of said molecule in transfected cells results in production of virus when transfected into cells, wherein said molecule encodes the amino acid sequence of SEQ ID NO: 3.

2. The composition of claim 1, wherein said molecule comprises the nucleic acid sequence of SEQ ID NO: 4.

3. A composition comprising a purified and isolated nucleic acid molecule, which encodes a chimeric human hepatitis C virus (HCV), wherein expression of said molecule in transfected cells results in production of virus when transfected into cells, wherein said molecule is producible by the process comprising, with reference to the nucleic acid sequence encoding the amino acid sequence of SEQ ID NO: 3, replacing a nucleic acid sequence of a HCV 1b genome that encodes the structural region of hepatitis C virus of said SEQ ID NO: 3 with a nucleic acid sequence that encodes the structural region from the genome of another strain of hepatitis C virus from a different genotype or subtype, to produce said molecule.

4. A composition comprising a purified and isolated nucleic acid molecule, which encodes a chimeric human hepatitis C virus (HCV), wherein expression of said molecule in transfected cells results in production of virus when transfected into cells, wherein said molecule is producible by the process comprising, with reference to the nucleic acid sequence encoding the amino acid sequence of SEQ ID NO: 3, replacing a nucleic acid sequence of a HCV 1b genome that encodes at least one HCV protein of said SEQ ID NO: 3 with a nucleic acid sequence that encodes the corresponding HCV protein from the genome of another strain of hepatitis C virus from a different genotype or subtype, to produce said molecule.

5. The composition of claim 4, wherein the HCV protein is selected from the group consisting of: NS3 protease, E1, E2 and NS4 proteins.

6. A method for inducing an immune response comprising the administration to a mammal an effective amount of the composition of claim 1, 3, or 4 to induce an immune response.

7. The method according to claim 6, wherein the composition is provided to a mammal not infected with a hepatitis C virus.

8. The method according to claim 6, wherein the composition is provided to a mammal infected with a hepatitis C virus.

* * * * *

SEQUENCE LISTING

```
<160> NUMBER OF SEQ ID NOS:  65

<210> SEQ ID NO 1
<211> LENGTH: 3011
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140
```

-continued

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Tyr
180 185 190

Gln Val Arg Asn Ser Ser Gly Leu Tyr His Val Thr Asn Asp Cys Pro
195 200 205

Asn Ser Ser Ile Val Tyr Glu Ala Ala Asp Ala Ile Leu His Thr Pro
210 215 220

Gly Cys Val Pro Cys Val Arg Glu Gly Asn Ala Ser Arg Cys Trp Val
225 230 235 240

Ala Val Thr Pro Thr Val Ala Thr Arg Asp Gly Lys Leu Pro Thr Thr
245 250 255

Gln Leu Arg Arg His Ile Asp Leu Leu Val Gly Ser Ala Thr Leu Cys
260 265 270

Ser Ala Leu Tyr Val Gly Asp Leu Cys Gly Ser Val Phe Leu Val Gly
275 280 285

Gln Leu Phe Thr Phe Ser Pro Arg Arg His Trp Thr Thr Gln Asp Cys
290 295 300

Asn Cys Ser Ile Tyr Pro Gly His Ile Thr Gly His Arg Met Ala Trp
305 310 315 320

Asp Met Met Met Asn Trp Ser Pro Thr Ala Ala Leu Val Val Ala Gln
325 330 335

Leu Leu Arg Ile Pro Gln Ala Ile Met Asp Met Ile Ala Gly Ala His
340 345 350

Trp Gly Val Leu Ala Gly Ile Ala Tyr Phe Ser Met Val Gly Asn Trp
355 360 365

Ala Lys Val Leu Val Val Leu Leu Leu Phe Ala Gly Val Asp Ala Glu
370 375 380

Thr His Val Thr Gly Gly Asn Ala Gly Arg Thr Thr Ala Gly Leu Val
385 390 395 400

Gly Leu Leu Thr Pro Gly Ala Lys Gln Asn Ile Gln Leu Ile Asn Thr
405 410 415

Asn Gly Ser Trp His Ile Asn Ser Thr Ala Leu Asn Cys Asn Glu Ser
420 425 430

Leu Asn Thr Gly Trp Leu Ala Gly Leu Phe Tyr Gln His Lys Phe Asn
435 440 445

Ser Ser Gly Cys Pro Glu Arg Leu Ala Ser Cys Arg Arg Leu Thr Asp
450 455 460

Phe Ala Gln Gly Trp Gly Pro Ile Ser Tyr Ala Asn Gly Ser Gly Leu
465 470 475 480

Asp Glu Arg Pro Tyr Cys Trp His Tyr Pro Pro Arg Pro Cys Gly Ile
485 490 495

Val Pro Ala Lys Ser Val Cys Gly Pro Val Tyr Cys Phe Thr Pro Ser
500 505 510

Pro Val Val Val Gly Thr Thr Asp Arg Ser Gly Ala Pro Thr Tyr Ser
515 520 525

Trp Gly Ala Asn Asp Thr Asp Val Phe Val Leu Asn Asn Thr Arg Pro
530 535 540

Pro Leu Gly Asn Trp Phe Gly Cys Thr Trp Met Asn Ser Thr Gly Phe
545 550 555 560

Thr Lys Val Cys Gly Ala Pro Pro Cys Val Ile Gly Gly Val Gly Asn

-continued

```
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990
```

-continued

Cys Gly Asp Ile Ile Asn Gly Leu Pro Val Ser Ala Arg Arg Gly Gln
995 1000 1005

Glu Ile Leu Leu Gly Pro Ala Asp Gly Met Val Ser Lys Gly Trp Arg
1010 1015 1020

Leu Leu Ala Pro Ile Thr Ala Tyr Ala Gln Gln Thr Arg Gly Leu Leu
1025 1030 1035 1040

Gly Cys Ile Ile Thr Ser Leu Thr Gly Arg Asp Lys Asn Gln Val Glu
1045 1050 1055

Gly Glu Val Gln Ile Val Ser Thr Ala Thr Gln Thr Phe Leu Ala Thr
1060 1065 1070

Cys Ile Asn Gly Val Cys Trp Thr Val Tyr His Gly Ala Gly Thr Arg
1075 1080 1085

Thr Ile Ala Ser Pro Lys Gly Pro Val Ile Gln Met Tyr Thr Asn Val
1090 1095 1100

Asp Gln Asp Leu Val Gly Trp Pro Ala Pro Gln Gly Ser Arg Ser Leu
1105 1110 1115 1120

Thr Pro Cys Thr Cys Gly Ser Ser Asp Leu Tyr Leu Val Thr Arg His
1125 1130 1135

Ala Asp Val Ile Pro Val Arg Arg Arg Gly Asp Ser Arg Gly Ser Leu
1140 1145 1150

Leu Ser Pro Arg Pro Ile Ser Tyr Leu Lys Gly Ser Ser Gly Gly Pro
1155 1160 1165

Leu Leu Cys Pro Ala Gly His Ala Val Gly Leu Phe Arg Ala Ala Val
1170 1175 1180

Cys Thr Arg Gly Val Ala Lys Ala Val Asp Phe Ile Pro Val Glu Asn
1185 1190 1195 1200

Leu Gly Thr Thr Met Arg Ser Pro Val Phe Thr Asp Asn Ser Ser Pro
1205 1210 1215

Pro Ala Val Pro Gln Ser Phe Gln Val Ala His Leu His Ala Pro Thr
1220 1225 1230

Gly Ser Gly Lys Ser Thr Lys Val Pro Ala Ala Tyr Ala Ala Gln Gly
1235 1240 1245

Tyr Lys Val Leu Val Leu Asn Pro Ser Val Ala Ala Thr Leu Gly Phe
1250 1255 1260

Gly Ala Tyr Met Ser Lys Ala His Gly Val Asp Pro Asn Ile Arg Thr
1265 1270 1275 1280

Gly Val Arg Thr Ile Thr Thr Gly Ser Pro Ile Thr Tyr Ser Thr Tyr
1285 1290 1295

Gly Lys Phe Leu Ala Asp Gly Gly Cys Ser Gly Gly Ala Tyr Asp Ile
1300 1305 1310

Ile Ile Cys Asp Glu Cys His Ser Thr Asp Ala Thr Ser Ile Leu Gly
1315 1320 1325

Ile Gly Thr Val Leu Asp Gln Ala Glu Thr Ala Gly Ala Arg Leu Val
1330 1335 1340

Val Leu Ala Thr Ala Thr Pro Pro Gly Ser Val Thr Val Ser His Pro
1345 1350 1355 1360

Asn Ile Glu Glu Val Ala Leu Ser Thr Thr Gly Glu Ile Pro Phe Tyr
1365 1370 1375

Gly Lys Ala Ile Pro Leu Glu Val Ile Lys Gly Gly Arg His Leu Ile
1380 1385 1390

Phe Cys His Ser Lys Lys Lys Cys Asp Glu Leu Ala Ala Lys Leu Val
1395 1400 1405

-continued

```
Ala Leu Gly Ile Asn Ala Val Ala Tyr Tyr Arg Gly Leu Asp Val Ser
   1410                1415                1420

Val Ile Pro Thr Ser Gly Asp Val Val Val Val Ser Thr Asp Ala Leu
1425                1430                1435                1440

Met Thr Gly Phe Thr Gly Asp Phe Asp Ser Val Ile Asp Cys Asn Thr
               1445                1450                1455

Cys Val Thr Gln Thr Val Asp Phe Ser Leu Asp Pro Thr Phe Thr Ile
           1460                1465                1470

Glu Thr Thr Thr Leu Pro Gln Asp Ala Val Ser Arg Thr Gln Arg Arg
       1475                1480                1485

Gly Arg Thr Gly Arg Gly Lys Pro Gly Ile Tyr Arg Phe Val Ala Pro
   1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
               1525                1530                1535

Val Arg Leu Arg Ala Tyr Met Asn Thr Pro Gly Leu Pro Val Cys Gln
           1540                1545                1550

Asp His Leu Glu Phe Trp Glu Gly Val Phe Thr Gly Leu Thr His Ile
       1555                1560                1565

Asp Ala His Phe Leu Ser Gln Thr Lys Gln Ser Gly Glu Asn Phe Pro
   1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
               1605                1610                1615

Thr Leu His Gly Pro Thr Pro Leu Leu Tyr Arg Leu Gly Ala Val Gln
           1620                1625                1630

Asn Glu Val Thr Leu Thr His Pro Ile Thr Lys Tyr Ile Met Thr Cys
       1635                1640                1645

Met Ser Ala Asp Leu Glu Val Val Thr Ser Thr Trp Val Leu Val Gly
   1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
               1685                1690                1695

Asp Arg Glu Val Leu Tyr Gln Glu Phe Asp Glu Met Glu Glu Cys Ser
           1700                1705                1710

Gln His Leu Pro Tyr Ile Glu Gln Gly Met Met Leu Ala Glu Gln Phe
       1715                1720                1725

Lys Gln Lys Ala Leu Gly Leu Leu Gln Thr Ala Ser Arg His Ala Glu
   1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
               1765                1770                1775

Gly Leu Ser Thr Leu Pro Gly Asn Pro Ala Ile Ala Ser Leu Met Ala
           1780                1785                1790

Phe Thr Ala Ala Val Thr Ser Pro Leu Thr Thr Gly Gln Thr Leu Leu
       1795                1800                1805

Phe Asn Ile Leu Gly Gly Trp Val Ala Ala Gln Leu Ala Ala Pro Gly
   1810                1815                1820

Ala Ala Thr Ala Phe Val Gly Ala Gly Leu Ala Gly Ala Ala Ile Gly
```

-continued

```
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
    2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
            2100                2105                2110

Pro Cys Gln Ile Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
            2180                2185                2190

Gly Ser Pro Pro Ser Met Ala Ser Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255
```

-continued

```
Asp Pro Leu Val Ala Glu Glu Asp Glu Arg Glu Val Ser Val Pro Ala
            2260                2265                2270

Glu Ile Leu Arg Lys Ser Arg Arg Phe Ala Arg Ala Leu Pro Val Trp
        2275                2280                2285

Ala Arg Pro Asp Tyr Asn Pro Pro Leu Val Glu Thr Trp Lys Lys Pro
    2290                2295                2300

Asp Tyr Glu Pro Pro Val Val His Gly Cys Pro Leu Pro Pro Pro Arg
2305                2310                2315                2320

Ser Pro Pro Val Pro Pro Pro Arg Lys Lys Arg Thr Val Val Leu Thr
                2325                2330                2335

Glu Ser Thr Leu Ser Thr Ala Leu Ala Glu Leu Ala Thr Lys Ser Phe
            2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Val Glu Ser
    2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Gly Ala Asp Thr Glu Asp
                2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
    2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
        2515                2520                2525

Arg Cys His Ala Arg Lys Ala Val Ala His Ile Asn Ser Val Trp Lys
    2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Ser Lys Leu Pro Leu Ala Val Met Gly
        2595                2600                2605

Ser Ser Tyr Gly Phe Gln Tyr Ser Pro Gly Gln Arg Val Glu Phe Leu
    2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
            2660                2665                2670
```

-continued

Ile Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly Val
2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
        2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
        2820                2825                2830

Ile Met Phe Ala Pro Thr Leu Trp Ala Arg Met Ile Leu Met Thr His
    2835                2840                2845

Phe Phe Ser Val Leu Ile Ala Arg Asp Gln Leu Glu Gln Ala Leu Asn
        2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
        2900                2905                2910

Gly Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys Tyr
        2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
        2980                2985                2990

Trp Phe Cys Leu Leu Leu Leu Ala Ala Gly Val Gly Ile Tyr Leu Leu
    2995                3000                3005

Pro Asn Arg
   3010

<210> SEQ ID NO 2
<211> LENGTH: 9599
<212> TYPE: DNA
<213> ORGANISM: Hepatitis C virus

<400> SEQUENCE: 2
gccagccccc tgatgggggc gacactccac catgaatcac tcccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180

-continued

```
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtacccttgg cccctctatg    600
gcaatgaggg ttgcgggtgg gcgggatggc tcctgtctcc ccgtggctct cggcctagct    660
ggggccccac agacccccgg cgtaggtcgc gcaatttggg taaggtcatc gataccctta    720
cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
```

-continued

```
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttcccccc ctcaacgtcc   2940
ggggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc acccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg ggacacgccg tgggcctatt cagggccgcg gtgtgcaccc   3900
gtggagtggc taaagcggtg gactttatcc ctgtggagaa cctagggaca accatgagat   3960
ccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc ccttttacg gcaaggctat ccccctcgag gtgatcaagg    4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccgggggagc   4860
gcccctccgg catgttcgac tcgtccgtcc tctgtgagtg ctatgacgcg ggctgtgctt   4920
```

-continued

```
ggtatgagct cacgcccgcc gagactacag ttaggctacg agcgtacatg aacaccccgg   4980
ggcttcccgt gtgccaggac catcttgaat tttgggaggg cgtctttacg ggcctcactc   5040
atatagatgc ccacttttta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
agttcaagca gaaggccctc ggcctcctgc agaccgcgtc ccgccatgca gaggttatca   5580
cccctgctgt ccagaccaac tggcagaaac tcgaggtctt ttgggcgaag cacatgtgga   5640
atttcatcag tgggatacaa tacttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ctgcctttgt gggtgctggc ctagctggcg ccgccatcgg cagcgttgga ctggggaagg   5880
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg ggtctggcg aggagacggc attatgcaca    6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga atttttcaca gaattggacg   6720
gggtgcgcct acacaggttt gcgcccccctt gcaagccctt gctgcgggag gaggtatcat  6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcacccccctt ctatggccag ctcctcggct agccagctgt  6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acctgcagaa attctgcgga agtctcggag attcgcccgg gccctgcccg   7200
tctgggcgcg gccggactac aaccccccgc tagtagagac gtggaaaaag cctgactacg   7260
```

-continued

```
aaccacctgt ggtccatggc tgcccgctac cacctccacg gtcccctcct gtgcctccgc   7320
ctcggaaaaa gcgtacggtg gtcctcaccg aatcaaccct atctactgcc ttggccgagc   7380
ttgccaccaa aagttttggc agctcctcaa cttccggcat tacgggcgac aatacgacaa   7440
catcctctga gcccgcccct tctggctgcc cccccgactc cgacgttgag tcctattctt   7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
caggcgcact cgtcaccccg tgcgctgcgg aagaacaaaa actgcccatc aacgcactga   7680
gcaactcgtt gctacgccat cacaatctgg tgtattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa aagtgaaggc taacttgcta tccgtagagg   7860
aagcttgcag cctgacgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga gaagggggt cgtaagccag ctcgtctcat cgtgttcccc gacctgggcg    8100
tgcgcgtgtg cgagaagatg gccctgtacg acgtggttag caagctcccc ctggccgtga   8160
tgggaagctc ctacggattc caatactcac caggacagcg ggttgaattc ctcgtgcaag   8220
cgtggaagtc caagaagacc ccgatggggt tctcgtatga tacccgctgt tttgactcca   8280
cagtcactga gagcgacatc cgtacggagg aggcaattta ccaatgttgt gacctggacc   8340
cccaagcccg cgtggccatc aagtccctca ctgagaggct ttatgttggg ggccctctta   8400
ccaattcaag gggggaaaac tgcggctacc gcaggtgccg cgcgagcggc gtactgacaa   8460
ctagctgtgg taacaccctc acttgctaca tcaaggcccg ggcagcctgt cgagccgcag   8520
ggctccagga ctgcaccatg ctcgtgtgtg gcgacgactt agtcgttatc tgtgaaagtg   8580
cgggggtcca ggaggacgcg gcgagcctga gagccttcac ggaggctatg accaggtact   8640
ccgccccccc cggggacccc ccacaaccag aatacgactt ggagcttata acatcatgct   8700
cctccaacgt gtcagtcgcc cacgacggcg ctggaaagag ggtctactac cttacccgtg   8760
accctacaac ccccctcgcg agagccgcgt gggagacagc aagacacact ccagtcaatt   8820
cctggctagg caacataatc atgtttgccc ccacactgtg ggcgaggatg atactgatga   8880
cccatttctt tagcgtcctc atagccaggg atcagcttga acaggctctt aactgtgaga   8940
tctacggagc ctgctactcc atagaaccac tggatctacc tccaatcatt caaagactcc   9000
atggcctcag cgcattttca ctccacagtt actctccagg tgaaatcaat agggtggccg   9060
catgcctcag aaaacttggg gtcccgccct tgcgagcttg gagacaccgg gcccggagcg   9120
tccgcgctag gcttctgtcc agaggaggca gggctgccat atgtggcaag tacctcttca   9180
actgggcagt aagaacaaag ctcaaactca ctccaatagc ggccgctggc cggctggact   9240
tgtccggttg gttcacggct ggctacagcg ggggagacat ttatcacagc gtgtctcatg   9300
cccggccccg ctggttctgg ttttgcctac tcctgctcgc tgcaggggta ggcatctacc   9360
tcctccccaa ccgatgaagg ttggggtaaa cactccggcc tcttaagcca tttcctgttt   9420
tttttttttt tttttttttt tttttctttt tttttttctt tcctttcctt ctttttttcc   9480
tttctttttc ccttctttaa tggtggctcc atcttagccc tagtcacggc tagctgtgaa   9540
aggtccgtga gccgcatgac tgcagagagt gctgatactg gcctctctgc agatcatgt    9599
```

-continued

<210> SEQ ID NO 3
<211> LENGTH: 3010
<212> TYPE: PRT
<213> ORGANISM: Hepatitis C virus

<400> SEQUENCE: 3

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Ala Ser Glu Arg Ser Gln Pro Arg Gly Arg Arg Gln Pro
     50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Val Ile Met His Thr Pro
    210                 215                 220

Gly Cys Val Pro Cys Val Gln Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Ile Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Ala Leu Leu Phe Ala Gly Val Asp Gly Glu
    370                 375                 380
```

-continued

```
Thr His Thr Thr Gly Arg Val Ala Gly His Thr Thr Ser Gly Phe Thr
385                 390                 395                 400

Ser Leu Phe Ser Ser Gly Ala Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Gln Thr Gly Phe Phe Ala Ala Leu Phe Tyr Ala His Lys Phe Asn
        435                 440                 445

Ser Ser Gly Cys Pro Glu Arg Met Ala Ser Cys Arg Pro Ile Asp Trp
    450                 455                 460

Phe Ala Gln Gly Trp Gly Pro Ile Thr Tyr Thr Lys Pro Asn Ser Ser
465                 470                 475                 480

Asp Gln Arg Pro Tyr Cys Trp His Tyr Ala Pro Arg Pro Cys Gly Val
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Val Pro Thr Tyr Ser
        515                 520                 525

Trp Gly Glu Asn Glu Thr Asp Val Met Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Arg Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Leu Asn Phe
    610                 615                 620

Ser Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ala Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ala Phe Val Ser Phe Ala Ile Lys Trp Glu Tyr Ile Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
        755                 760                 765

Leu Val Phe Phe Cys Ala Ala Trp Tyr Ile Lys Gly Arg Leu Ala Pro
    770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Leu Asp Arg Glu Met Ala Ala
```

-continued

```
                805                 810                 815

Ser Cys Gly Gly Ala Val Leu Val Gly Leu Val Phe Leu Thr Leu Ser
            820                 825                 830

Pro Tyr Tyr Lys Val Phe Leu Thr Arg Leu Ile Trp Trp Leu Gln Tyr
        835                 840                 845

Phe Ile Thr Arg Ala Glu Ala His Met Gln Val Trp Val Pro Pro Leu
    850                 855                 860

Asn Val Arg Gly Gly Arg Asp Ala Ile Ile Leu Leu Thr Cys Ala Val
865                 870                 875                 880

His Pro Glu Leu Ile Phe Asp Ile Thr Lys Leu Leu Leu Ala Ile Leu
                885                 890                 895

Gly Pro Leu Met Val Leu Gln Ala Gly Ile Thr Arg Val Pro Tyr Phe
            900                 905                 910

Val Arg Ala Gln Gly Leu Ile Arg Ala Cys Met Leu Val Arg Lys Val
        915                 920                 925

Ala Gly Gly His Tyr Val Gln Met Val Phe Met Lys Leu Gly Ala Leu
    930                 935                 940

Thr Gly Thr Tyr Val Tyr Asn His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Ala Met Glu Thr Lys Val Ile Thr Trp Gly Ala Asp Thr Ala Ala
            980                 985                 990

Cys Gly Asp Ile Ile Leu Gly Leu Pro Val Ser Ala Arg Arg Gly Lys
        995                 1000                1005

Glu Ile Phe Leu Gly Pro Ala Asp Ser Leu Glu Gly Gln Gly Trp Arg
   1010                1015                1020

Leu Leu Ala Pro Ile Thr Ala Tyr Ser Gln Gln Thr Arg Gly Val Leu
1025                1030                1035                1040

Gly Cys Ile Ile Thr Ser Leu Thr Gly Arg Asp Lys Asn Gln Val Glu
               1045                1050                1055

Gly Glu Val Gln Val Val Ser Thr Ala Thr Gln Ser Phe Leu Ala Thr
           1060                1065                1070

Cys Ile Asn Gly Val Cys Trp Thr Val Tyr His Gly Ala Gly Ser Lys
       1075                1080                1085

Thr Leu Ala Gly Pro Lys Gly Pro Ile Thr Gln Met Tyr Thr Asn Val
   1090                1095                1100

Asp Leu Asp Leu Val Gly Trp Gln Ala Pro Pro Gly Ala Arg Ser Met
1105                1110                1115                1120

Thr Pro Cys Ser Cys Gly Ser Ser Asp Leu Tyr Leu Val Thr Arg His
               1125                1130                1135

Ala Asp Val Ile Pro Val Arg Arg Arg Gly Asp Ser Arg Gly Ser Leu
           1140                1145                1150

Leu Ser Pro Arg Pro Val Ser Tyr Leu Lys Gly Ser Ser Gly Gly Pro
       1155                1160                1165

Leu Leu Cys Pro Ser Gly His Val Val Gly Val Phe Arg Ala Ala Val
   1170                1175                1180

Cys Thr Arg Gly Val Ala Lys Ala Val Asp Phe Ile Pro Val Glu Ser
1185                1190                1195                1200

Met Glu Thr Thr Met Arg Ser Pro Val Phe Thr Asp Asn Ser Thr Pro
               1205                1210                1215

Pro Ala Val Pro Gln Thr Phe Gln Val Ala His Leu His Ala Pro Thr
           1220                1225                1230
```

-continued

```
Gly Ser Gly Lys Ser Thr Lys Val Pro Ala Ala Tyr Ala Ala Gln Gly
       1235                1240                1245

Tyr Lys Val Leu Val Leu Asn Pro Ser Val Ala Ala Thr Leu Gly Phe
   1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Gly Ser Ile Thr Tyr Ser Thr Tyr
               1285                1290                1295

Gly Lys Phe Leu Ala Asp Gly Gly Cys Ser Gly Gly Ala Tyr Asp Ile
           1300                1305                1310

Ile Ile Cys Asp Glu Cys His Ser Thr Asp Ser Thr Thr Ile Leu Gly
       1315                1320                1325

Ile Gly Thr Val Leu Asp Gln Ala Glu Thr Ala Gly Ala Arg Leu Val
   1330                1335                1340

Val Leu Ala Thr Ala Thr Pro Pro Gly Ser Val Thr Val Pro His Pro
1345                1350                1355                1360

Asn Ile Glu Glu Ile Gly Leu Ser Asn Asn Gly Glu Ile Pro Phe Tyr
               1365                1370                1375

Gly Lys Ala Ile Pro Ile Glu Ala Ile Lys Gly Gly Arg His Leu Ile
           1380                1385                1390

Phe Cys His Ser Lys Lys Lys Cys Asp Glu Leu Ala Ala Lys Leu Thr
       1395                1400                1405

Gly Leu Gly Leu Asn Ala Val Ala Tyr Tyr Arg Gly Leu Asp Val Ser
   1410                1415                1420

Val Ile Pro Pro Ile Gly Asp Val Val Val Val Ala Thr Asp Ala Leu
1425                1430                1435                1440

Met Thr Gly Phe Thr Gly Asp Phe Asp Ser Val Ile Asp Cys Asn Thr
               1445                1450                1455

Cys Val Thr Gln Thr Val Asp Phe Ser Leu Asp Pro Thr Phe Thr Ile
           1460                1465                1470

Glu Thr Thr Thr Val Pro Gln Asp Ala Val Ser Arg Ser Gln Arg Arg
       1475                1480                1485

Gly Arg Thr Gly Arg Gly Arg Ser Gly Ile Tyr Arg Phe Val Thr Pro
   1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
               1525                1530                1535

Val Arg Leu Arg Ala Tyr Leu Asn Thr Pro Gly Leu Pro Val Cys Gln
           1540                1545                1550

Asp His Leu Glu Phe Trp Glu Ser Val Phe Thr Gly Leu Thr His Ile
       1555                1560                1565

Asp Ala His Phe Leu Ser Gln Thr Lys Gln Ala Gly Asp Asn Phe Pro
   1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
               1605                1610                1615

Thr Leu His Gly Pro Thr Pro Leu Leu Tyr Arg Leu Gly Ala Val Gln
           1620                1625                1630

Asn Glu Val Ile Leu Thr His Pro Ile Thr Lys Tyr Ile Met Ala Cys
       1635                1640                1645
```

-continued

```
Met Ser Ala Asp Leu Glu Val Val Thr Ser Thr Trp Val Leu Val Gly
   1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Lys Pro Ala Val Val Pro
               1685                1690                1695

Asp Arg Glu Val Leu Tyr Gln Glu Phe Asp Glu Met Glu Glu Cys Ala
           1700                1705                1710

Ser Gln Leu Pro Tyr Ile Glu Gln Gly Met Gln Leu Ala Glu Gln Phe
       1715                1720                1725

Lys Gln Lys Ala Leu Gly Leu Leu Gln Thr Ala Thr Lys Gln Ala Glu
   1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
               1765                1770                1775

Gly Leu Ser Thr Leu Pro Gly Asn Pro Ala Ile Ala Ser Leu Met Ala
           1780                1785                1790

Phe Thr Ala Ser Ile Thr Ser Pro Leu Thr Thr Gln Asn Thr Leu Leu
       1795                1800                1805

Phe Asn Ile Leu Gly Gly Trp Val Ala Ala Gln Leu Ala Pro Pro Ser
   1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
               1845                1850                1855

Ala Gly Val Ala Gly Ala Leu Val Ala Phe Lys Val Met Ser Gly Glu
           1860                1865                1870

Val Pro Ser Thr Glu Asp Leu Val Asn Leu Leu Pro Ala Ile Leu Ser
       1875                1880                1885

Pro Gly Ala Leu Val Val Gly Val Val Cys Ala Ala Ile Leu Arg Arg
   1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
               1925                1930                1935

Glu Ser Asp Ala Ala Ala Arg Val Thr Gln Ile Leu Ser Ser Leu Thr
           1940                1945                1950

Ile Thr Gln Leu Leu Lys Arg Leu His Gln Trp Ile Asn Glu Asp Cys
       1955                1960                1965

Ser Thr Pro Cys Ser Gly Ser Trp Leu Arg Asp Val Trp Asp Trp Ile
   1970                1975                1980

Cys Thr Val Leu Thr Asp Phe Lys Thr Trp Leu Gln Ser Lys Leu Leu
1985                1990                1995                2000

Pro Arg Leu Pro Gly Val Pro Phe Leu Ser Cys Gln Arg Gly Tyr Lys
               2005                2010                2015

Gly Val Trp Arg Gly Asp Gly Ile Met Gln Thr Thr Cys Pro Cys Gly
           2020                2025                2030

Ala Gln Ile Ala Gly His Val Lys Asn Gly Ser Met Arg Ile Val Gly
       2035                2040                2045

Pro Arg Thr Cys Ser Asn Thr Trp His Gly Thr Phe Pro Ile Asn Ala
   2050                2055                2060

Tyr Thr Thr Gly Pro Cys Thr Pro Ser Pro Ala Pro Asn Tyr Ser Arg
```

-continued 2065 2070 2075 2080

Ala Leu Trp Arg Val Ala Ala Glu Glu Tyr Val Glu Val Thr Arg Val
2085 2090 2095

Gly Asp Phe His Tyr Val Thr Gly Met Thr Thr Asp Asn Val Lys Cys
2100 2105 2110

Pro Cys Gln Val Pro Ala Pro Glu Phe Phe Thr Glu Val Asp Gly Val
2115 2120 2125

Arg Leu His Arg Tyr Ala Pro Ala Cys Lys Pro Leu Leu Arg Glu Asp
2130 2135 2140

Val Thr Phe Gln Val Gly Leu Asn Gln Tyr Leu Val Gly Ser Gln Leu
2145 2150 2155 2160

Pro Cys Glu Pro Glu Pro Asp Val Thr Val Leu Thr Ser Met Leu Thr
2165 2170 2175

Asp Pro Ser His Ile Thr Ala Glu Thr Ala Lys Arg Arg Leu Ala Arg
2180 2185 2190

Gly Ser Pro Pro Ser Leu Ala Ser Ser Ser Ala Ser Gln Leu Ser Ala
2195 2200 2205

Pro Ser Leu Lys Ala Thr Cys Thr Thr His His Asp Ser Pro Asp Ala
2210 2215 2220

Asp Leu Ile Glu Ala Asn Leu Leu Trp Arg Gln Glu Met Gly Gly Asn
2225 2230 2235 2240

Ile Thr Arg Val Glu Ser Glu Asn Lys Val Val Ile Leu Asp Ser Phe
2245 2250 2255

Glu Pro Leu His Ala Glu Gly Asp Glu Arg Glu Ile Ser Val Ala Ala
2260 2265 2270

Glu Ile Leu Arg Lys Ser Arg Lys Phe Pro Ser Ala Leu Pro Ile Trp
2275 2280 2285

Ala Arg Pro Asp Tyr Asn Pro Pro Leu Leu Glu Ser Trp Lys Asp Pro
2290 2295 2300

Asp Tyr Val Pro Pro Val Val His Gly Cys Pro Leu Pro Pro Thr Lys
2305 2310 2315 2320

Ala Pro Pro Ile Pro Pro Pro Arg Arg Lys Arg Thr Val Val Leu Thr
2325 2330 2335

Glu Ser Asn Val Ser Ser Ala Leu Ala Glu Leu Ala Thr Lys Thr Phe
2340 2345 2350

Gly Ser Ser Gly Ser Ser Ala Val Asp Ser Gly Thr Ala Thr Ala Leu
2355 2360 2365

Pro Asp Leu Ala Ser Asp Asp Gly Asp Lys Gly Ser Asp Val Glu Ser
2370 2375 2380

Tyr Ser Ser Met Pro Pro Leu Glu Gly Glu Pro Gly Asp Pro Asp Leu
2385 2390 2395 2400

Ser Asp Gly Ser Trp Ser Thr Val Ser Glu Glu Ala Ser Glu Asp Val
2405 2410 2415

Val Cys Cys Ser Met Ser Tyr Thr Trp Thr Gly Ala Leu Ile Thr Pro
2420 2425 2430

Cys Ala Ala Glu Glu Ser Lys Leu Pro Ile Asn Pro Leu Ser Asn Ser
2435 2440 2445

Leu Leu Arg His His Asn Met Val Tyr Ala Thr Thr Ser Arg Ser Ala
2450 2455 2460

Ser Leu Arg Gln Lys Lys Val Thr Phe Asp Arg Leu Gln Val Leu Asp
2465 2470 2475 2480

Asp His Tyr Arg Asp Val Leu Lys Glu Met Lys Ala Lys Ala Ser Thr
2485 2490 2495

-continued

```
Val Lys Ala Lys Leu Leu Ser Ile Glu Glu Ala Cys Lys Leu Thr Pro
            2500                2505                2510

Pro His Ser Ala Lys Ser Lys Phe Gly Tyr Gly Ala Lys Asp Val Arg
        2515                2520                2525

Asn Leu Ser Ser Arg Ala Val Asn His Ile Arg Ser Val Trp Glu Asp
    2530                2535                2540

Leu Leu Glu Asp Thr Glu Thr Pro Ile Asp Thr Thr Ile Met Ala Lys
2545                2550                2555                2560

Ser Glu Val Phe Cys Val Gln Pro Glu Lys Gly Gly Arg Lys Pro Ala
                2565                2570                2575

Arg Leu Ile Val Phe Pro Asp Leu Gly Val Arg Val Cys Glu Lys Met
            2580                2585                2590

Ala Leu Tyr Asp Val Val Ser Thr Leu Pro Gln Ala Val Met Gly Ser
        2595                2600                2605

Ser Tyr Gly Phe Gln Tyr Ser Pro Lys Gln Arg Val Glu Phe Leu Val
    2610                2615                2620

Asn Thr Trp Lys Ser Lys Lys Cys Pro Met Gly Phe Ser Tyr Asp Thr
2625                2630                2635                2640

Arg Cys Phe Asp Ser Thr Val Thr Glu Ser Asp Ile Arg Val Glu Glu
                2645                2650                2655

Ser Ile Tyr Gln Cys Cys Asp Leu Ala Pro Glu Ala Arg Gln Ala Ile
            2660                2665                2670

Arg Ser Leu Thr Glu Arg Leu Tyr Ile Gly Gly Pro Leu Thr Asn Ser
        2675                2680                2685

Lys Gly Gln Asn Cys Gly Tyr Arg Arg Cys Arg Ala Ser Gly Val Leu
    2690                2695                2700

Thr Thr Ser Cys Gly Asn Thr Leu Thr Cys Tyr Leu Lys Ala Thr Ala
2705                2710                2715                2720

Ala Cys Arg Ala Ala Lys Leu Gln Asp Cys Thr Met Leu Val Asn Gly
                2725                2730                2735

Asp Asp Leu Val Val Ile Cys Glu Ser Ala Gly Thr Gln Glu Asp Ala
            2740                2745                2750

Ala Ala Leu Arg Ala Phe Thr Glu Ala Met Thr Arg Tyr Ser Ala Pro
        2755                2760                2765

Pro Gly Asp Pro Pro Gln Pro Glu Tyr Asp Leu Glu Leu Ile Thr Ser
    2770                2775                2780

Cys Ser Ser Asn Val Ser Val Ala His Asp Ala Ser Gly Lys Arg Val
2785                2790                2795                2800

Tyr Tyr Leu Thr Arg Asp Pro Thr Thr Pro Leu Ala Arg Ala Ala Trp
                2805                2810                2815

Glu Thr Ala Arg His Thr Pro Ile Asn Ser Trp Leu Gly Asn Ile Ile
            2820                2825                2830

Met Tyr Ala Pro Thr Leu Trp Ala Arg Met Ile Leu Met Thr His Phe
        2835                2840                2845

Phe Ser Ile Leu Leu Ala Gln Glu Gln Leu Glu Lys Ala Leu Asp Cys
    2850                2855                2860

Gln Ile Tyr Gly Ala Cys Tyr Ser Ile Glu Pro Leu Asp Leu Pro Gln
2865                2870                2875                2880

Ile Ile Glu Arg Leu His Gly Leu Ser Ala Phe Thr Leu His Ser Tyr
                2885                2890                2895

Ser Pro Gly Glu Ile Asn Arg Val Ala Ser Cys Leu Arg Lys Leu Gly
            2900                2905                2910
```

-continued

```
Val Pro Pro Leu Arg Thr Trp Arg His Arg Ala Arg Ser Val Arg Ala
       2915                2920                2925

Lys Leu Leu Ser Gln Gly Gly Arg Ala Ala Thr Cys Gly Arg Tyr Leu
   2930                2935                2940

Phe Asn Trp Ala Val Arg Thr Lys Leu Lys Leu Thr Pro Ile Pro Ala
2945                2950                2955                2960

Ala Ser Gln Leu Asp Leu Ser Gly Trp Phe Val Ala Gly Tyr Ser Gly
               2965                2970                2975

Gly Asp Ile Tyr His Ser Leu Ser Arg Ala Arg Pro Arg Trp Phe Pro
           2980                2985                2990

Leu Cys Leu Leu Leu Leu Ser Val Gly Val Gly Ile Tyr Leu Leu Pro
       2995                3000                3005

Asn Arg
   3010
```

<210> SEQ ID NO 4
<211> LENGTH: 9595
<212> TYPE: DNA
<213> ORGANISM: Hepatitis C virus

<400> SEQUENCE: 4

```
gccagccccc tgatgggggc gacactccac catgaatcac tcccctgtga ggaactactg      60

tcttcacgca gaaagcgtct agccatggcg ttagtatgag tgtcgtgcag cctccaggac     120

ccccccctccc gggagagcca tagtggtctg cggaaccggt gagtacaccg gaattgccag    180

gacgaccggg tcctttcttg gatcaacccg ctcaatgcct ggagatttgg gcgtgccccc     240

gcgagactgc tagccgagta gtgttgggtc gcgaaaggcc ttgtggtact gcctgatagg     300

gtgcttgcga gtgccccggg aggtctcgta gaccgtgcac catgagcacg aatcctaaac     360

ctcaaagaaa aaccaaacgt aacaccaacc gccgcccaca ggacgtcaag ttcccgggcg     420

gtggtcagat cgttggtgga gtttacctgt tgccgcgcag gggccccagg ttgggtgtgc     480

gcgcgactag gaaggcttcc gagcggtcgc aacctcgtgg aaggcgacaa cctatcccaa     540

aggctcgccg acccgagggc agggcctggg ctcagcccgg gtacccttgg cccctctatg     600

gcaatgaggg cctggggtgg gcaggatggc tcctgtcacc ccgcggctcc cggcctagtt     660

ggggccccac ggaccccccgg cgtaggtcgc gtaacttggg taaggtcatc gataccctta    720

catgcggctt cgccgatctc atggggtaca ttccgctcgt cggcgccccc ctagggggcg     780

ctgccagggc cttggcacac ggtgtccggg ttctggagga cggcgtgaac tatgcaacag     840

ggaacttgcc cggttgctct ttctctatct tcctcttggc tctgctgtcc tgtttgacca     900

tcccagcttc cgcttatgaa gtgcgcaacg tgtccgggat ataccatgtc acgaacgact     960

gctccaactc aagcattgtg tatgaggcag cggacgtgat catgcatact cccgggtgcg    1020

tgccctgtgt tcaggagggt aacagctccc gttgctgggt agcgctcact cccacgctcg    1080

cggccaggaa tgccagcgtc cccactacga caatacgacg ccacgtcgac ttgctcgttg    1140

ggacggctgc tttctgctcc gctatgtacg tgggggatct ctgcggatct attttcctcg    1200

tctcccagct gttcaccttc tcgcctcgcc ggcatgagac agtgcaggac tgcaactgct    1260

caatctatcc cggccatgta tcaggtcacc gcatggcttg ggatatgatg atgaactggt    1320

cacctacaac agccctagtg gtgtcgcagt tgctccggat cccacaagct gtcgtggaca    1380

tggtggcggg ggcccactgg ggagtcctgg cgggccttgc ctactattcc atggtaggga    1440

actgggctaa ggttctgatt gtggcgctac tctttgccgg cgttgacggg gagacccaca    1500
```

-continued

```
cgacggggag ggtggccggc cacaccacct ccgggttcac gtcccttttc tcatctgggg   1560
cgtctcagaa aatccagctt gtgaatacca acggcagctg gcacatcaac aggactgccc   1620
taaattgcaa tgactccctc caaactgggt tctttgccgc gctgttttac gcacacaagt   1680
tcaactcgtc cgggtgcccg gagcgcatgg ccagctgccg ccccattgac tggttcgccc   1740
aggggtgggg ccccatcacc tatactaagc ctaacagctc ggatcagagg ccttattgct   1800
ggcattacgc gcctcgaccg tgtggtgtcg tacccgcgtc gcaggtgtgt ggtccagtgt   1860
attgtttcac cccaagccct gttgtggtgg ggaccaccga tcgttccggt gtccctacgt   1920
atagctgggg ggagaatgag acagacgtga tgctcctcaa caacacgcgt ccgccacaag   1980
gcaactggtt cggctgtaca tggatgaata gtactgggtt cactaagacg tgcggaggtc   2040
cccgtgtaa catcgggggg gtcggtaacc gcaccttgat ctgccccacg gactgcttcc    2100
ggaagcaccc cgaggctact tacacaaaat gtggctcggg gccctggttg acacctaggt   2160
gcctagtaga ctacccatac aggctttggc actacccctg cactctcaat ttttccatct   2220
ttaaggttag gatgtatgtg gggggcgtgg agcacaggct caatgccgca tgcaattgga   2280
ctcgaggaga gcgctgtaac ttggaggaca gggataggtc agaactcagc ccgctgctgc   2340
tgtctacaac agagtggcag atactgccct gtgctttcac caccctaccg gctttatcca   2400
ctggtttgat ccatctccat cagaacatcg tggacgtgca atacctgtac ggtgtagggt   2460
cagcgtttgt ctcctttgca atcaaatggg agtacatcct gttgcttttc cttctcctgg   2520
cagacgcgcg cgtgtgtgcc tgcttgtgga tgatgctgct gatagcccag gctgaggccg   2580
ccttagagaa cttggtggtc ctcaatgcgg cgtccgtggc cggagcgcat ggtattctct   2640
cctttcttgt gttcttctgc gccgcctggt acattaaggg caggctggct cctggggcgg   2700
cgtatgcttt ttatggcgta tggccgctgc tcctgctcct actggcgtta ccaccacgag   2760
cttacgcctt ggaccgggag atggctgcat cgtgcggggg tgcggttctt gtaggtctgg   2820
tattcttgac cttgtcacca tactacaaag tgtttctcac taggctcata tggtggttac   2880
aatactttat caccagagcc gaggcgcaca tgcaagtgtg ggtccccccc ctcaacgttc   2940
ggggaggccg cgatgccatc atcctcctca cgtgtgcggt tcatccagag ttaatttttg   3000
acatcaccaa actcctgctc gccatactcg gcccgctcat ggtgctccag gctggcataa   3060
cgagagtgcc gtacttcgtg cgcgctcaag ggctcattcg tgcatgcatg ttagtgcgaa   3120
aagtcgccgg gggtcattat gtccaaatgg tcttcatgaa gctgggcgcg ctgacaggta   3180
cgtacgttta taaccatctt accccactgc gggactgggc ccacgcgggc ctacgagacc   3240
ttgcggtggc ggtagagccc gtcgtcttct ccgccatgga gaccaaggtc atcacctggg   3300
gagcagacac cgctgcgtgt ggggacatca tcttgggtct acccgtctcc gcccgaaggg   3360
ggaaggagat atttttggga ccggctgata gtctcgaagg gcaagggtgg cgactccttg   3420
cgcccatcac ggcctactcc caacaaacgc ggggcgtact tggttgcatc atcactagcc   3480
tcacaggccg ggacaagaac caggtcgaag gggaggttca agtggtttct accgcaacac   3540
aatctttcct ggcgacctgc atcaacggcg tgtgctggac tgtctaccat ggcgctggct   3600
cgaagaccct agccggtcca aaaggtccaa tcacccaaat gtacaccaat gtagacctgg   3660
acctcgtcgg ctggcaggcg ccccccgggg cgcgctccat gacaccatgc agctgtggca   3720
gctcggacct ttacttggtc acgagacatg ctgatgtcat tccggtgcgc cggcgaggcg   3780
acagcagggg aagtctactc tcccccaggc ccgtctccta cctgaaaggc tcctcgggtg   3840
gtccattgct ttgcccttcg ggcacgtcgt tgggcgtctt ccgggctgct gtgtgcaccc   3900
```

-continued

```
ggggggtcgc gaaggcggtg gacttcatac ccgttgagtc tatggaaact accatgcggt   3960
ctccggtctt cacagacaac tcaacccccc cggctgtacc gcagacattc caagtggcac   4020
atctgcacgc tcctactggc agcggcaaga gcaccaaagt gccggctgcg tatgcagccc   4080
aagggtacaa ggtgctcgtc ctgaacccgt ccgttgccgc caccttaggg tttggggcgt   4140
atatgtccaa ggcacacggt atcgacccta acatcagaac tggggtaagg accattacca   4200
cgggcggctc cattacgtac tccacctatg gcaagttcct tgccgacggt ggctgttctg   4260
ggggcgccta tgacatcata atatgtgatg agtgccactc aactgactcg actaccatct   4320
tgggcatcgg cacagtcctg gaccaagcgg agacggctgg agcgcggctc gtcgtgctcg   4380
ccaccgctac acctccggga tcggttaccg tgccacaccc caatatcgag gaaataggcc   4440
tgtccaacaa tggagagatc cccttctatg gcaaagccat ccccattgag gccatcaagg   4500
gggggaggca tctcattttc tgccattcca agaagaaatg tgacgagctc gccgcaaagc   4560
tgacaggcct cggactgaac gctgtagcat attaccgggg ccttgatgtg tccgtcatac   4620
cgcctatcgg agacgtcgtt gtcgtggcaa cagacgctct aatgacgggt ttcaccggcg   4680
attttgactc agtgatcgac tgcaatacat gtgtcaccca gacagtcgac ttcagcttgg   4740
atcccacctt caccattgag acgacgaccg tgccccaaga cgcggtgtcg cgctcgcaac   4800
ggcgaggtag aactggcagg ggtaggagtg gcatctacag gtttgtgact ccaggagaac   4860
ggccctcggg catgttcgat tcttcggtcc tgtgtgagtg ctatgacgcg ggctgtgctt   4920
ggtatgagct cacgcccgct gagacctcgg ttaggttgcg ggcttaccta aatacaccag   4980
ggttgcccgt ctgccaggac catctggagt tctgggagag cgtcttcaca ggcctcaccc   5040
acatagatgc ccacttcctg tcccagacta aacaggcagg agacaacttt ccttacctgg   5100
tggcatatca agctacagtg tgcgccaggg ctcaagctcc acctccatcg tgggaccaaa   5160
tgtggaagtg tctcatacgg ctgaaaccta cactgcacgg gccaacaccc ctgctgtata   5220
ggctaggagc cgtccaaaat gaggtcatcc tcacacaccc cataactaaa tacatcatgg   5280
catgcatgtc ggctgacctg gaggtcgtca ctagcacctg ggtgctggta ggcggagtcc   5340
ttgcagcttt ggccgcatac tgcctgacga caggcagtgt ggtcattgtg ggcaggatca   5400
tcttgtccgg gaagccagct gtcgttcccg acagggaagt cctctaccag gagttcgatg   5460
agatggaaga gtgtgcctca caacttcctt acatcgagca gggaatgcag ctcgccgagc   5520
aattcaagca aaaggcgctc gggttgttgc aaacggccac caagcaagcg gaggctgctg   5580
ctcccgtggt ggagtccaag tggcgagccc ttgagacctt ctgggcgaag cacatgtgga   5640
atttcatcag cggaatacag tacctagcag gcttatccac tctgcctgga aaccccgcga   5700
tagcatcatt gatggcattt acagcttcta tcactagccc gctcaccacc caaaacaccc   5760
tcctgtttaa catcttgggg ggatgggtgg ctgcccaact cgctcctccc agcgctgcgt   5820
cagctttcgt gggcgccggc atcgccggag cggctgttgg cagcataggc cttgggaagg   5880
tgctcgtgga catcttggcg ggctatgggg caggggtagc cggcgcactc gtggccttta   5940
aggtcatgag cggcgaggtg ccctccaccg aggacctggt caacttactc cctgccatcc   6000
tctctcctgg tgccctggtc gtcggggtcg tgtgcgcagc aatactgcgt cggcacgtgg   6060
gcccgggaga gggggctgtg cagtggatga accggctgat agcgttcgct tcgcggggta   6120
accacgtctc ccctacgcac tatgtgcctg agagcgacgc tgcagcacgt gtcactcaga   6180
tcctctctag ccttaccatc actcaactgc tgaagcggct ccaccagtgg attaatgagg   6240
```

-continued actgctctac gccatgctcc ggctcgtggc taagggatgt ttgggattgg atatgcacgg 6300
tgttgactga cttcaagacc tggctccagt ccaaactcct gccgcggtta ccgggagtcc 6360
ctttcctgtc atgccaacgc gggtacaagg gagtctggcg gggggacggc atcatgcaaa 6420
ccacctgccc atgcggagca cagatcgccg gacatgtcaa aaacggttcc atgaggatcg 6480
tagggcctag aacctgcagc aacacgtggc acggaacgtt ccccatcaac gcatacacca 6540
cgggaccttg cacaccctcc ccggcgccca actattccag ggcgctatgg cgggtggctg 6600
ctgaggagta cgtggaggtt acgcgtgtgg gggatttcca ctacgtgacg ggcatgacca 6660
ctgacaacgt aaagtgccca tgccaggttc cggcccccga attcttcacg gaggtggatg 6720
gagtgcggtt gcacaggtac gctccggcgt gcaaacctct tctacgggag gacgtcacgt 6780
tccaggtcgg gctcaaccaa tacttggtcg ggtcgcagct cccatgcgag cccgaaccgg 6840
acgtaacagt gcttacttcc atgctcaccg atccctccca cattacagca gagacggcta 6900
agcgtaggct ggctagaggg tctccccct ctttagccag ctcatcagct agccagttgt 6960
ctgcgccttc tttgaaggcg acatgcacta cccaccatga ctccccggac gctgacctca 7020
tcgaggccaa cctcttgtgg cggcaggaga tgggcggaaa catcactcgc gtggagtcag 7080
agaataaggt agtaattctg gactctttcg aaccgcttca cgcggagggg gatgagaggg 7140
agatatccgt cgcggcggag atcctgcgaa aatccaggaa gttcccctca gcgttgccca 7200
tatgggcacg cccggactac aatcctccac tgctagagtc ctggaaggac ccggactacg 7260
tccctccggt ggtacacgga tgcccattgc cacctaccaa ggctcctcca ataccacctc 7320
cacggagaaa gaggacggtt gtcctgacag aatccaatgt gtcttctgcc ttggcggagc 7380
tcgccactaa gaccttcggt agctccggat cgtcggccgt tgatagcggc acggcgaccg 7440
cccttcctga cctggcctcc gacgacggtg acaaaggatc cgacgttgag tcgtactcct 7500
ccatgccccc ccttgaaggg gagccggggg accccgatct cagcgacggg tcttggtcta 7560
ccgtgagtga ggaggctagt gaggatgtcg tctgctgctc aatgtcctat acgtggacag 7620
gcgccctgat cacgccatgc gctgcggagg aaagtaagct gcccatcaac ccgttgagca 7680
actctttgct gcgtcaccac aacatggtct acgccacaac atcccgcagc gcaagcctcc 7740
ggcagaagaa ggtcaccttt gacagattgc aagtcctgga tgatcattac cgggacgtac 7800
tcaaggagat gaaggcgaag gcgtccacag ttaaggctaa gcttctatct atagaggagg 7860
cctgcaagct gacgccccca cattcggcca aatccaaatt tggctatggg gcaaaggacg 7920
tccggaacct atccagcagg gccgttaacc acatccgctc cgtgtgggag gacttgctgg 7980
aagacactga aacaccaatt gacaccacca tcatggcaaa aagtgaggtt ttctgcgtcc 8040
aaccagagaa gggaggccgc aagccagctc gccttatcgt attcccagac ctgggagttc 8100
gtgtatgcga gaagatggcc ctttacgacg tggtctccac ccttcctcag gccgtgatgg 8160
gctcctcata cggatttcaa tactccccca agcagcgggt cgagttcctg gtgaatacct 8220
ggaaatcaaa gaaatgccct atgggcttct catatgacac ccgctgtttt gactcaacgg 8280
tcactgagag tgacattcgt gttgaggagt caatttacca atgttgtgac ttggcccccg 8340
aggccagaca ggccataagg tcgctcacag agcggcttta catcgggggt cccctgacta 8400
actcaaaagg gcagaactgc ggttatcgcc ggtgccgcgc aagtggcgtg ctgacgacta 8460
gctgcggtaa taccctcaca tgttacttga aggccactgc agcctgtcga gctgcaaagc 8520
tccaggactg cacgatgctc gtgaacggag acgaccttgt cgttatctgt gaaagcgcgg 8580
gaacccagga ggatgcggcg gccctacgag ccttcacgga ggctatgact aggtattccg 8640

-continued

```
ccccccccgg ggatccgccc caaccagaat acgacctgga gctgataaca tcatgttcct   8700

ccaatgtgtc agtcgcgcac gatgcatctg gcaaaagggt atactacctc acccgtgacc   8760

ccaccacccc ccttgcacgg gctgcgtggg agacagctag acacactcca atcaactctt   8820

ggctaggcaa tatcatcatg tatgcgccca ccctatgggc aaggatgatt ctgatgactc   8880

actttttctc catccttcta gctcaagagc aacttgaaaa agccctggat tgtcagatct   8940

acggggcttg ctactccatt gagccacttg acctacctca gatcattgaa cgactccatg   9000

gtcttagcgc atttacactc cacagttact ctccaggtga gatcaatagg gtggcttcat   9060

gcctcaggaa acttggggta ccacccttgc gaacctggag acatcgggcc agaagtgtcc   9120

gcgctaagct actgtcccag ggggggaggg ccgccacttg tggcagatac ctctttaact   9180

gggcagtaag gaccaagctt aaactcactc caatcccggc cgcgtcccag ctggacttgt   9240

ctggctggtt cgtcgctggt tacagcgggg gagacatata tcacagcctg tctcgtgccc   9300

gaccccgctg gtttccgttg tgcctactcc tactttctgt aggggtaggc atttacctgc   9360

tccccaaccg atgaacgggg agctaaccac tccaggcctt aagccatttc ctgttttttt   9420

tttttttttt tttttttttt tctttttttt tttctttcct ttccttcttt ttttcctttc   9480

tttttccctt ctttaatggt ggctccatct tagccctagt cacggctagc tgtgaaaggt   9540

ccgtgagccg catgactgca gagagtgctg atactggcct ctctgcagat catgt        9595


<210> SEQ ID NO 5
<211> LENGTH: 3011
<212> TYPE: PRT
<213> ORGANISM: Hepatitis C virus

<400> SEQUENCE: 5

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Ala Ser Glu Arg Ser Gln Pro Arg Gly Arg Arg Gln Pro
     50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205
```

-continued

Asn Ser Ser Ile Val Tyr Glu Ala Ala Asp Val Ile Met His Thr Pro
    210                 215                 220

Gly Cys Val Pro Cys Val Gln Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Ile Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Ala Leu Leu Phe Ala Gly Val Asp Gly Glu
    370                 375                 380

Thr His Thr Thr Gly Arg Val Ala Gly His Thr Thr Ser Gly Phe Thr
385                 390                 395                 400

Ser Leu Phe Ser Ser Gly Ala Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Gln Thr Gly Phe Phe Ala Ala Leu Phe Tyr Ala His Lys Phe Asn
        435                 440                 445

Ser Ser Gly Cys Pro Glu Arg Met Ala Ser Cys Arg Pro Ile Asp Trp
    450                 455                 460

Phe Ala Gln Gly Trp Gly Pro Ile Thr Tyr Thr Lys Pro Asn Ser Ser
465                 470                 475                 480

Asp Gln Arg Pro Tyr Cys Trp His Tyr Ala Pro Arg Pro Cys Gly Val
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Val Pro Thr Tyr Ser
        515                 520                 525

Trp Gly Glu Asn Glu Thr Asp Val Met Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Arg Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Leu Asn Phe
    610                 615                 620

-continued

```
Ser Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ala Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ala Phe Val Ser Phe Ala Ile Lys Trp Glu Tyr Ile Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
        755                 760                 765

Leu Val Phe Phe Cys Ala Ala Trp Tyr Ile Lys Gly Arg Leu Ala Pro
    770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
```

-continued

```
                1045                1050                1055

Gly Glu Val Gln Ile Val Ser Thr Ala Thr Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Leu Phe Arg Ala Ala Val
    1170                1175                1180

Cys Thr Arg Gly Val Ala Lys Ala Val Asp Phe Ile Pro Val Glu Asn
1185                1190                1195                1200

Leu Gly Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
    1410                1415                1420

Val Ile Pro Thr Ser Gly Asp Val Val Val Val Ser Thr Asp Ala Leu
1425                1430                1435                1440

Met Thr Gly Phe Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
            1460                1465                1470
```

-continued

```
Glu Thr Thr Thr Leu Pro Gln Asp Ala Val Ser Arg Thr Gln Arg Arg
       1475                1480                1485

Gly Arg Thr Gly Arg Gly Lys Pro Gly Ile Tyr Arg Phe Val Ala Pro
   1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
               1525                1530                1535

Val Arg Leu Arg Ala Tyr Met Asn Thr Pro Gly Leu Pro Val Cys Gln
           1540                1545                1550

Asp His Leu Glu Phe Trp Glu Gly Val Phe Thr Gly Leu Thr His Ile
       1555                1560                1565

Asp Ala His Phe Leu Ser Gln Thr Lys Gln Ser Gly Glu Asn Phe Pro
   1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
               1605                1610                1615

Thr Leu His Gly Pro Thr Pro Leu Leu Tyr Arg Leu Gly Ala Val Gln
           1620                1625                1630

Asn Glu Val Thr Leu Thr His Pro Ile Thr Lys Tyr Ile Met Thr Cys
       1635                1640                1645

Met Ser Ala Asp Leu Glu Val Val Thr Ser Thr Trp Val Leu Val Gly
   1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
               1685                1690                1695

Asp Arg Glu Val Leu Tyr Gln Glu Phe Asp Glu Met Glu Glu Cys Ser
           1700                1705                1710

Gln His Leu Pro Tyr Ile Glu Gln Gly Met Met Leu Ala Glu Gln Phe
       1715                1720                1725

Lys Gln Lys Ala Leu Gly Leu Leu Gln Thr Ala Ser Arg His Ala Glu
   1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
               1765                1770                1775

Gly Leu Ser Thr Leu Pro Gly Asn Pro Ala Ile Ala Ser Leu Met Ala
           1780                1785                1790

Phe Thr Ala Ala Val Thr Ser Pro Leu Thr Thr Gly Gln Thr Leu Leu
       1795                1800                1805

Phe Asn Ile Leu Gly Gly Trp Val Ala Ala Gln Leu Ala Ala Pro Gly
   1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
               1845                1850                1855

Ala Gly Val Ala Gly Ala Leu Val Ala Phe Lys Ile Met Ser Gly Glu
           1860                1865                1870

Val Pro Ser Thr Glu Asp Leu Val Asn Leu Leu Pro Ala Ile Leu Ser
       1875                1880                1885
```

-continued

```
Pro Gly Ala Leu Val Val Gly Val Val Cys Ala Ala Ile Leu Arg Arg
   1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
               1925                1930                1935

Glu Ser Asp Ala Ala Ala Arg Val Thr Ala Ile Leu Ser Ser Leu Thr
           1940                1945                1950

Val Thr Gln Leu Leu Arg Arg Leu His Gln Trp Ile Ser Ser Glu Cys
       1955                1960                1965

Thr Thr Pro Cys Ser Gly Ser Trp Leu Arg Asp Ile Trp Asp Trp Ile
   1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
               2005                2010                2015

Gly Val Trp Arg Gly Asp Gly Ile Met His Thr Arg Cys His Cys Gly
           2020                2025                2030

Ala Glu Ile Thr Gly His Val Lys Asn Gly Thr Met Arg Ile Val Gly
       2035                2040                2045

Pro Arg Thr Cys Arg Asn Met Trp Ser Gly Thr Phe Pro Ile Asn Ala
   2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
               2085                2090                2095

Gly Asp Phe His Tyr Val Ser Gly Met Thr Thr Asp Asn Leu Lys Cys
           2100                2105                2110

Pro Cys Gln Ile Pro Ser Pro Glu Phe Phe Thr Glu Leu Asp Gly Val
       2115                2120                2125

Arg Leu His Arg Phe Ala Pro Pro Cys Lys Pro Leu Leu Arg Glu Glu
   2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
               2165                2170                2175

Asp Pro Ser His Ile Thr Ala Glu Ala Ala Gly Arg Arg Leu Ala Arg
           2180                2185                2190

Gly Ser Pro Pro Ser Met Ala Ser Ser Ser Ala Ser Gln Leu Ser Ala
       2195                2200                2205

Pro Ser Leu Lys Ala Thr Cys Thr Ala Asn His Asp Ser Pro Asp Ala
   2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
               2245                2250                2255

Asp Pro Leu Val Ala Glu Glu Asp Glu Arg Glu Val Ser Val Pro Ala
           2260                2265                2270

Glu Ile Leu Arg Lys Ser Arg Arg Phe Ala Arg Ala Leu Pro Val Trp
       2275                2280                2285

Ala Arg Pro Asp Tyr Asn Pro Pro Leu Val Glu Thr Trp Lys Lys Pro
   2290                2295                2300

Asp Tyr Glu Pro Pro Val Val His Gly Cys Pro Leu Pro Pro Pro Arg
```

-continued 2305 2310 2315 2320

Ser Pro Pro Val Pro Pro Pro Arg Lys Lys Arg Thr Val Val Leu Thr
2325 2330 2335

Glu Ser Thr Leu Ser Thr Ala Leu Ala Glu Leu Ala Thr Lys Ser Phe
2340 2345 2350

Gly Ser Ser Ser Thr Ser Gly Ile Thr Gly Asp Asn Thr Thr Thr Ser
2355 2360 2365

Ser Glu Pro Ala Pro Ser Gly Cys Pro Pro Asp Ser Asp Val Glu Ser
2370 2375 2380

Tyr Ser Ser Met Pro Pro Leu Glu Gly Glu Pro Gly Asp Pro Asp Leu
2385 2390 2395 2400

Ser Asp Gly Ser Trp Ser Thr Val Ser Ser Gly Ala Asp Thr Glu Asp
2405 2410 2415

Val Val Cys Cys Ser Met Ser Tyr Ser Trp Thr Gly Ala Leu Val Thr
2420 2425 2430

Pro Cys Ala Ala Glu Glu Gln Lys Leu Pro Ile Asn Ala Leu Ser Asn
2435 2440 2445

Ser Leu Leu Arg His His Asn Leu Val Tyr Ser Thr Thr Ser Arg Ser
2450 2455 2460

Ala Cys Gln Arg Gln Lys Lys Val Thr Phe Asp Arg Leu Gln Val Leu
2465 2470 2475 2480

Asp Ser His Tyr Gln Asp Val Leu Lys Glu Val Lys Ala Ala Ala Ser
2485 2490 2495

Lys Val Lys Ala Asn Leu Leu Ser Val Glu Glu Ala Cys Ser Leu Thr
2500 2505 2510

Pro Pro His Ser Ala Lys Ser Lys Phe Gly Tyr Gly Ala Lys Asp Val
2515 2520 2525

Arg Cys His Ala Arg Lys Ala Val Ala His Ile Asn Ser Val Trp Lys
2530 2535 2540

Asp Leu Leu Glu Asp Ser Val Thr Pro Ile Asp Thr Thr Ile Met Ala
2545 2550 2555 2560

Lys Asn Glu Val Phe Cys Val Gln Pro Glu Lys Gly Gly Arg Lys Pro
2565 2570 2575

Ala Arg Leu Ile Val Phe Pro Asp Leu Gly Val Arg Val Cys Glu Lys
2580 2585 2590

Met Ala Leu Tyr Asp Val Val Ser Lys Leu Pro Leu Ala Val Met Gly
2595 2600 2605

Ser Ser Tyr Gly Phe Gln Tyr Ser Pro Gly Gln Arg Val Glu Phe Leu
2610 2615 2620

Val Gln Ala Trp Lys Ser Lys Lys Thr Pro Met Gly Phe Ser Tyr Asp
2625 2630 2635 2640

Thr Arg Cys Phe Asp Ser Thr Val Thr Glu Ser Asp Ile Arg Thr Glu
2645 2650 2655

Glu Ala Ile Tyr Gln Cys Cys Asp Leu Asp Pro Gln Ala Arg Val Ala
2660 2665 2670

Ile Lys Ser Leu Thr Glu Arg Leu Tyr Val Gly Gly Pro Leu Thr Asn
2675 2680 2685

Ser Arg Gly Glu Asn Cys Gly Tyr Arg Arg Cys Arg Ala Ser Gly Val
2690 2695 2700

Leu Thr Thr Ser Cys Gly Asn Thr Leu Thr Cys Tyr Ile Lys Ala Arg
2705 2710 2715 2720

Ala Ala Cys Arg Ala Ala Gly Leu Gln Asp Cys Thr Met Leu Val Cys
2725 2730 2735

-continued

```
Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asn
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Phe
            2980                2985                2990

Trp Phe Cys Leu Leu Leu Leu Ala Ala Gly Val Gly Ile Tyr Leu Leu
        2995                3000                3005

Pro Asn Arg
    3010
```

<210> SEQ ID NO 6
<211> LENGTH: 9599
<212> TYPE: DNA
<213> ORGANISM: Hepatitis C virus

<400> SEQUENCE: 6

```
gccagccccc tgatgggggc gacactccac catgaatcac tcccctgtga ggaactactg      60

tcttcacgca gaaagcgtct agccatggcg ttagtatgag tgtcgtgcag cctccaggac     120

ccccctcccc gggagagcca tagtggtctg cggaaccggt gagtacaccg gaattgccag     180

gacgaccggg tcctttcttg gatcaacccg ctcaatgcct ggagatttgg gcgtgccccc     240

gcgagactgc tagccgagta gtgttgggtc gcgaaaggcc ttgtggtact gcctgatagg     300

gtgcttgcga gtgccccggg aggtctcgta gaccgtgcac catgagcacg aatcctaaac     360

ctcaaagaaa aaccaaacgt aacaccaacc gccgcccaca ggacgtcaag ttcccgggcg     420

gtggtcagat cgttggtgga gtttacctgt tgccgcgcag gggccccagg ttgggtgtgc     480
```

-continued

```
gcgcgactag gaaggcttcc gagcggtcgc aacctcgtgg aaggcgacaa cctatcccaa    540
aggctcgccg acccgagggc agggcctggg ctcagcccgg gtacccttgg cccctctatg    600
gcaatgaggg cctggggtgg gcaggatggc tcctgtcacc ccgcggctcc cggcctagtt    660
ggggccccac ggacccccgg cgtaggtcgc gtaacttggg taaggtcatc gataccctta    720
catgcggctt cgccgatctc atggggtaca ttccgctcgt cggcgccccc ctagggggcg    780
ctgccagggc cttggcacac ggtgtccggg ttctggagga cggcgtgaac tatgcaacag    840
ggaacttgcc cggttgctct ttctctatct tcctcttggc tctgctgtcc tgtttgacca    900
tcccagcttc cgcttatgaa gtgcgcaacg tgtccgggat ataccatgtc acgaacgact    960
gctccaactc aagcattgtg tatgaggcag cggacgtgat catgcatact cccgggtgcg   1020
tgccctgtgt tcaggagggt aacagctccc gttgctgggt agcgctcact cccacgctcg   1080
cggccaggaa tgccagcgtc cccactacga caatacgacg ccacgtcgac ttgctcgttg   1140
ggacggctgc tttctgctcc gctatgtacg tgggggatct ctgcggatct attttcctcg   1200
tctcccagct gttcaccttc tcgcctcgcc ggcatgagac agtgcaggac tgcaactgct   1260
caatctatcc cggccatgta tcaggtcacc gcatggcttg ggatatgatg atgaactggt   1320
cacctacaac agccctagtg gtgtcgcagt tgctccggat cccacaagct gtcgtggaca   1380
tggtggcggg ggcccactgg ggagtcctgg cgggccttgc ctactattcc atggtaggga   1440
actgggctaa ggttctgatt gtggcgctac tctttgccgg cgttgacggg gagacccaca   1500
cgacggggag ggtggccggc cacaccacct ccgggttcac gtcccttttc tcatctgggg   1560
cgtctcagaa aatccagctt gtgaatacca acggcagctg gcacatcaac aggactgccc   1620
taaattgcaa tgactccctc caaactgggt tctttgccgc gctgttttac gcacacaagt   1680
tcaactcgtc cgggtgcccg gagcgcatgg ccagctgccg ccccattgac tggttcgccc   1740
aggggtgggg ccccatcacc tatactaagc ctaacagctc ggatcagagg ccttattgct   1800
ggcattacgc gcctcgaccg tgtggtgtcg tacccgcgtc gcaggtgtgt ggtccagtgt   1860
attgtttcac ccccaagccct gttgtggtgg ggaccaccga tcgttccggt gtccctacgt   1920
atagctgggg ggagaatgag acagacgtga tgctcctcaa caacacgcgt ccgccacaag   1980
gcaactggtt cggctgtaca tggatgaata gtactgggtt cactaagacg tgcggaggtc   2040
ccccgtgtaa catcgggggg gtcggtaacc gcaccttgat ctgccccacg gactgcttcc   2100
ggaagcaccc cgaggctact tacacaaaat gtggctcggg gccctggttg acacctaggt   2160
gcctagtaga ctacccatac aggctttggc actacccctg cactctcaat ttttccatct   2220
ttaaggttag gatgtatgtg gggggcgtgg agcacaggct caatgccgca tgcaattgga   2280
ctcgaggaga gcgctgtaac ttggaggaca gggataggtc agaactcagc ccgctgctgc   2340
tgtctacaac agagtggcag atactgccct gtgctttcac caccctaccg gctttatcca   2400
ctggtttgat ccatctccat cagaacatcg tggacgtgca atacctgtac ggtgtagggt   2460
cagcgtttgt ctcctttgca atcaaatggg agtacatcct gttgcttttc cttctcctgg   2520
cagacgcgcg cgtgtgtgcc tgcttgtgga tgatgctgct gatagcccag gctgaggccg   2580
ccttagagaa cttggtggtc ctcaatgcgg cgtccgtggc cggagcgcat ggtattctct   2640
cctttcttgt gttcttctgc gccgcctggt acattaaggg caggctggct cctggggcgg   2700
cgtatgcttt ttatggcgta tggccgctgc tcctgctcct actggcgtta ccaccacgag   2760
catatgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
```

-continued

```
agtattttct gaccagagta gaagcgcaac tgcacgtgtg ggttcccccc ctcaacgtcc   2940
ggggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc acccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgcccccggc ccatttccta cttgaaaggc tcctcggggg   3840
gtccgctgtt gtgccccgcg ggacacgccg tgggcctatt cagggccgcg gtgtgcaccc   3900
gtggagtggc taaagcggtg gactttatcc ctgtggagaa cctagggaca accatgagat   3960
ccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc cccttttacg gcaaggctat ccccctcgag gtgatcaagg   4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccgggggagc   4860
gcccctccgg catgttcgac tcgtccgtcc tctgtgagtg ctatgacgcg ggctgtgctt   4920
ggtatgagct cacgcccgcc gagactacag ttaggctacg agcgtacatg aacaccccgg   4980
ggcttcccgt gtgccaggac catcttgaat tttgggaggg cgtctttacg ggcctcactc   5040
atatagatgc ccacttttta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
```

-continued

```
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
agttcaagca gaaggccctc ggcctcctgc agaccgcgtc ccgccatgca gaggttatca   5580
cccctgctgt ccagaccaac tggcagaaac tcgaggtctt ttgggcgaag cacatgtgga   5640
atttcatcag tgggatacaa tacttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ctgcctttgt gggtgctggc ctagctggcg ccgccatcgg cagcgttgga ctggggaagg   5880
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccgggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga atttttcaca gaattggacg   6720
gggtgcgcct acacaggttt gcgccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcaccccctt ctatggccag ctcctcggct agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acctgcagaa attctgcgga agtctcggag attcgcccgg gccctgcccg   7200
tctgggcgcg gccggactac aaccccccgc tagtagagac gtggaaaaag cctgactacg   7260
aaccacctgt ggtccatggc tgcccgctac cacctccacg gtcccctcct gtgcctccgc   7320
ctcggaaaaa gcgtacggtg gtcctcaccg aatcaaccct atctactgcc ttggccgagc   7380
ttgccaccaa aagttttggc agctcctcaa cttccggcat tacgggcgac aatacgacaa   7440
catcctctga gcccgcccct tctggctgcc cccccgactc cgacgttgag tcctattctt   7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
```

-continued caggcgcact cgtcaccccg tgcgctgcgg aagaacaaaa actgcccatc aacgcactga 7680
gcaactcgtt gctacgccat cacaatctgg tgtattccac cacttcacgc agtgcttgcc 7740
aaaggcagaa gaaagtcaca tttgacagac tgcaagttct ggacagccat taccaggacg 7800
tgctcaagga ggtcaaagca gcggcgtcaa aagtgaaggc taacttgcta tccgtagagg 7860
aagcttgcag cctgacgccc ccacattcag ccaaatccaa gtttggctat ggggcaaaag 7920
acgtccgttg ccatgccaga aaggccgtag cccacatcaa ctccgtgtgg aaagaccttc 7980
tggaagacag tgtaacacca atagacacta ccatcatggc caagaacgag gttttctgcg 8040
ttcagcctga gaagggggggt cgtaagccag ctcgtctcat cgtgttcccc gacctgggcg 8100
tgcgcgtgtg cgagaagatg gccctgtacg acgtggttag caagctcccc ctggccgtga 8160
tgggaagctc ctacggattc caatactcac caggacagcg ggttgaattc ctcgtgcaag 8220
cgtggaagtc caagaagacc ccgatggggt tctcgtatga tacccgctgt tttgactcca 8280
cagtcactga gagcgacatc cgtacggagg aggcaattta ccaatgttgt gacctggacc 8340
cccaagcccg cgtggccatc aagtccctca ctgagaggct ttatgttggg ggccctctta 8400
ccaattcaag gggggaaaac tgcggctacc gcaggtgccg cgcgagcggc gtactgacaa 8460
ctagctgtgg taacaccctc acttgctaca tcaaggcccg ggcagcctgt cgagccgcag 8520
ggctccagga ctgcaccatg ctcgtgtgtg gcgacgactt agtcgttatc tgtgaaagtg 8580
cgggggtcca ggaggacgcg gcgagcctga gagccttcac ggaggctatg accaggtact 8640
ccgccccccc cggggacccc ccacaaccag aatacgactt ggagcttata acatcatgct 8700
cctccaacgt gtcagtcgcc cacgacggcg ctggaaagag ggtctactac cttacccgtg 8760
accctacaac ccccctcgcg agagccgcgt gggagacagc aagacacact ccagtcaatt 8820
cctggctagg caacataatc atgtttgccc ccacactgtg ggcgaggatg atactgatga 8880
cccatttctt tagcgtcctc atagccaggg atcagcttga acaggctctt aactgtgaga 8940
tctacggagc ctgctactcc atagaaccac tggatctacc tccaatcatt caaagactcc 9000
atggcctcag cgcattttca ctccacagtt actctccagg tgaaatcaat agggtggccg 9060
catgcctcag aaaacttggg gtcccgccct tgcgagcttg gagacaccgg gcccggagcg 9120
tccgcgctag gcttctgtcc agaggaggca gggctgctat atgtggcaag tacctcttca 9180
actgggcagt aagaacaaag ctcaaactca ctccaatagc ggccgctggc cggctggact 9240
tgtccggttg gttcacggct ggctacagcg ggggagacat ttatcacagc gtgtctcatg 9300
cccggccccg ctggttctgg ttttgcctac tcctgctcgc tgcaggggta ggcatctacc 9360
tcctccccaa ccgatgaagg ttggggtaaa cactccggcc tcttaagcca tttcctgttt 9420
tttttttttt tttttttttt tttttctttt ttttttttctt tcctttcctt ctttttttcc 9480
tttctttttc ccttctttaa tggtggctcc atcttagccc tagtcacggc tagctgtgaa 9540
aggtccgtga gccgcatgac tgcagagagt gctgatactg gcctctctgc agatcatgt 9599

<210> SEQ ID NO 7
<211> LENGTH: 31
<212> TYPE: DNA
<213> ORGANISM: Hepatitis C virus

<400> SEQUENCE: 7
ggctacagcg gggggagaca tttatcacag c 31

<210> SEQ ID NO 8

-continued

```
<211> LENGTH: 30
<212> TYPE: DNA
<213> ORGANISM: Hepatitis C virus

<400> SEQUENCE: 8

tcatgcggct cacggacctt tcacagctag                              30

<210> SEQ ID NO 9
<211> LENGTH: 38
<212> TYPE: DNA
<213> ORGANISM: Hepatitis C virus

<400> SEQUENCE: 9

gtccaagctt atcacagcgt gtctcatgcc cggccccg                     38

<210> SEQ ID NO 10
<211> LENGTH: 39
<212> TYPE: DNA
<213> ORGANISM: Hepatitis C virus

<400> SEQUENCE: 10

cgtctctaga ggacctttca cagctagccg tgactaggg                    39

<210> SEQ ID NO 11
<211> LENGTH: 38
<212> TYPE: DNA
<213> ORGANISM: Hepatitis C virus

<400> SEQUENCE: 11

tgaaggttgg ggtaaacact ccggcctctt aggccatt                     38

<210> SEQ ID NO 12
<211> LENGTH: 35
<212> TYPE: DNA
<213> ORGANISM: Hepatitis C virus

<400> SEQUENCE: 12

acatgatctg cagagaggcc agtatcagca ctctc                        35

<210> SEQ ID NO 13
<211> LENGTH: 46
<212> TYPE: DNA
<213> ORGANISM: Hepatitis C virus

<400> SEQUENCE: 13

gtccaagctt acgcgtaaac actccggcct ccttaagcca ttcctg            46

<210> SEQ ID NO 14
<211> LENGTH: 47
<212> TYPE: DNA
<213> ORGANISM: Hepatitis C virus

<400> SEQUENCE: 14

cgtctctaga catgatctgc agagaggcca gtatcagcac tctctgc           47

<210> SEQ ID NO 15
<211> LENGTH: 67
<212> TYPE: DNA
<213> ORGANISM: Hepatitis C virus

<400> SEQUENCE: 15

ttttttttgc ggccgctaat acgactcact atagccagcc ccctgatggg ggcgacactc    60

caccatg                                                             67
```

-continued

<210> SEQ ID NO 16
<211> LENGTH: 30
<212> TYPE: DNA
<213> ORGANISM: Hepatitis C virus

<400> SEQUENCE: 16
actgtcttca cgcagaaagc gtctagccat 30

<210> SEQ ID NO 17
<211> LENGTH: 43
<212> TYPE: DNA
<213> ORGANISM: Hepatitis C virus

<400> SEQUENCE: 17
cgtctctaga caggaaatgg cttaagaggc cggagtgttt acc 43

<210> SEQ ID NO 18
<211> LENGTH: 26
<212> TYPE: DNA
<213> ORGANISM: Hepatitis C virus

<400> SEQUENCE: 18
gcctattggc ctggagtggt tagctc 26

<210> SEQ ID NO 19
<211> LENGTH: 40
<212> TYPE: DNA
<213> ORGANISM: Hepatitis C virus

<400> SEQUENCE: 19
aggatggcct taaggcctgg agtggttagc tccccgttca 40

<210> SEQ ID NO 20
<211> LENGTH: 39
<212> TYPE: DNA
<213> ORGANISM: Hepatitis C virus

<400> SEQUENCE: 20
cgtcatcgat cctcagcggg catatgcact ggacacgga 39

<210> SEQ ID NO 21
<211> LENGTH: 32
<212> TYPE: DNA
<213> ORGANISM: Hepatitis C virus

<400> SEQUENCE: 21
catgcaccag ctgatatagc gcttgtaata tg 32

<210> SEQ ID NO 22
<211> LENGTH: 30
<212> TYPE: DNA
<213> ORGANISM: Hepatitis C virus

<400> SEQUENCE: 22
tccgtagagg aagcttgcag cctgacgccc 30

<210> SEQ ID NO 23
<211> LENGTH: 34
<212> TYPE: DNA
<213> ORGANISM: Hepatitis C virus

<400> SEQUENCE: 23

-continued gtacttgcca catatagcag ccctgcctcc tctg 34

<210> SEQ ID NO 24
<211> LENGTH: 34
<212> TYPE: DNA
<213> ORGANISM: Hepatitis C virus

<400> SEQUENCE: 24
cagaggaggc agggctgcta tatgtggcaa gtac 34

<210> SEQ ID NO 25
<211> LENGTH: 43
<212> TYPE: DNA
<213> ORGANISM: Hepatitis C virus

<400> SEQUENCE: 25
cgtctctaga caggaaatgg cttaagaggc cggagtgttt acc 43

<210> SEQ ID NO 26
<211> LENGTH: 36
<212> TYPE: DNA
<213> ORGANISM: Hepatitis C virus

<400> SEQUENCE: 26
tgcaattgga ctcgaggaga gcgctgtaac ttggag 36

<210> SEQ ID NO 27
<211> LENGTH: 35
<212> TYPE: DNA
<213> ORGANISM: Hepatitis C virus

<400> SEQUENCE: 27
cggtccaagg catatgctcg tggtggtaac gccag 35

<210> SEQ ID NO 28
<211> LENGTH: 35
<212> TYPE: PRT
<213> ORGANISM: Hepatitis C virus

<400> SEQUENCE: 28

Ala Gly Val Asp Gly Glu Thr His Thr Thr Gly Arg Val Ala Gly His
1 5 10 15

Thr Thr Ser Gly Phe Thr Ser Leu Phe Ser Ser Gly Ala Ser Gln Lys
20 25 30

Ile Gln Leu
35

<210> SEQ ID NO 29
<211> LENGTH: 19
<212> TYPE: PRT
<213> ORGANISM: Hepatitis C virus

<400> SEQUENCE: 29

Gly Trp Gly Pro Ile Thr Tyr Thr Lys Pro Asn Ser Ser Asp Gln Arg
1 5 10 15

Pro Tyr Cys

<210> SEQ ID NO 30
<211> LENGTH: 35
<212> TYPE: PRT
<213> ORGANISM: Hepatitis C virus

<400> SEQUENCE: 30

-continued

```
Ala Gly Val Asp Gly Glu Thr His Thr Thr Gly Arg Val Ala Gly His
  1               5                  10                  15

Thr Thr Ser Arg Phe Thr Ser Leu Phe Ser Ser Gly Ala Ser Gln Lys
             20                  25                  30

Ile Gln Leu
         35


<210> SEQ ID NO 31
<211> LENGTH: 19
<212> TYPE: PRT
<213> ORGANISM: Hepatitis C virus

<400> SEQUENCE: 31

Gly Trp Gly Pro Ile Thr Tyr Thr Glu Pro Asn Ser Ser Asp Gln Arg
  1               5                  10                  15

Pro Tyr Cys


<210> SEQ ID NO 32
<211> LENGTH: 35
<212> TYPE: PRT
<213> ORGANISM: Hepatitis C virus

<400> SEQUENCE: 32

Ala Gly Val Asp Gly Glu Thr His Thr Thr Gly Arg Val Val Gly His
  1               5                  10                  15

Thr Thr Ser Gly Phe Thr Ser Leu Phe Ser Ser Gly Ala Ser Gln Lys
             20                  25                  30

Ile Gln Leu
         35


<210> SEQ ID NO 33
<211> LENGTH: 19
<212> TYPE: PRT
<213> ORGANISM: Hepatitis C virus

<400> SEQUENCE: 33

Gly Trp Gly Pro Ile Thr Tyr Thr Gly Pro Asn Ser Ser Asp Gln Arg
  1               5                  10                  15

Pro Tyr Cys


<210> SEQ ID NO 34
<211> LENGTH: 35
<212> TYPE: PRT
<213> ORGANISM: Hepatitis C virus

<400> SEQUENCE: 34

Ala Gly Val Asp Gly Glu Thr His Thr Thr Gly Arg Val Val Gly Arg
  1               5                  10                  15

Thr Thr Ser Gly Phe Thr Ser Leu Phe Ser Ser Gly Ala Ser Gln Lys
             20                  25                  30

Ile Gln Leu
         35


<210> SEQ ID NO 35
<211> LENGTH: 19
<212> TYPE: PRT
<213> ORGANISM: Hepatitis C virus

<400> SEQUENCE: 35

Gly Trp Gly Pro Ile Ala Tyr Thr Glu Pro Asn Ser Ser Asp Gln Arg
```

-continued

```
  1               5                   10                  15

Pro Tyr Cys


<210> SEQ ID NO 36
<211> LENGTH: 35
<212> TYPE: PRT
<213> ORGANISM: Hepatitis C virus

<400> SEQUENCE: 36

Ala Gly Val Asp Gly Thr Thr Tyr Thr Ser Gly Gly Val Ala Gly Arg
  1               5                   10                  15

Thr Thr Ser Gly Phe Thr Ser Leu Phe Ser Pro Gly Ala Ser Gln Lys
            20                  25                  30

Ile Gln Leu
        35


<210> SEQ ID NO 37
<211> LENGTH: 35
<212> TYPE: PRT
<213> ORGANISM: Hepatitis C virus

<400> SEQUENCE: 37

Thr Gly Val Asp Gly Thr Thr Tyr Thr Ser Gly Gly Ala Ala Gly Arg
  1               5                   10                  15

Thr Thr Ser Gly Phe Thr Ser Leu Phe Ser Ser Gly Ala Ser Gln Lys
            20                  25                  30

Ile Gln Leu
        35


<210> SEQ ID NO 38
<211> LENGTH: 35
<212> TYPE: PRT
<213> ORGANISM: Hepatitis C virus

<400> SEQUENCE: 38

Thr Gly Val Asp Gly Thr Thr Tyr Thr Ser Gly Gly Val Ala Gly Arg
  1               5                   10                  15

Thr Thr Ser Gly Phe Thr Ser Leu Phe Ser Ser Gly Ala Ser Gln Lys
            20                  25                  30

Ile Gln Leu
        35


<210> SEQ ID NO 39
<211> LENGTH: 19
<212> TYPE: PRT
<213> ORGANISM: Hepatitis C virus

<400> SEQUENCE: 39

Gly Trp Gly Pro Ile Thr His Thr Glu Pro Asn Ser Ser Asp Gln Arg
  1               5                   10                  15

Pro Tyr Cys


<210> SEQ ID NO 40
<211> LENGTH: 19
<212> TYPE: PRT
<213> ORGANISM: Hepatitis C virus

<400> SEQUENCE: 40

Gly Trp Gly Pro Ile Thr Tyr Thr Gly Pro Asp Ser Leu Asp Gln Arg
  1               5                   10                  15
```

-continued

Pro Tyr Cys

<210> SEQ ID NO 41
<211> LENGTH: 35
<212> TYPE: PRT
<213> ORGANISM: Hepatitis C virus

<400> SEQUENCE: 41

Ala Gly Val Asp Gly Ala Thr Tyr Thr Ser Gly Gly Val Ala Gly Arg
1 5 10 15

Thr Thr Ser Gly Phe Thr Ser Leu Phe Ser Ser Gly Ala Ser Gln Lys
20 25 30

Ile Gln Leu
35

<210> SEQ ID NO 42
<211> LENGTH: 19
<212> TYPE: PRT
<213> ORGANISM: Hepatitis C virus

<400> SEQUENCE: 42

Gly Trp Gly Pro Ile Thr Tyr Thr Glu Pro Asn Ser Pro Asp Gln Arg
1 5 10 15

Pro Tyr Cys

<210> SEQ ID NO 43
<211> LENGTH: 35
<212> TYPE: PRT
<213> ORGANISM: Hepatitis C virus

<400> SEQUENCE: 43

Ala Gly Val Asp Gly Lys Thr Tyr Thr Ser Gly Gly Ala Ala Ser His
1 5 10 15

Thr Thr Ser Arg Phe Thr Ser Leu Phe Ser Pro Gly Ala Ser Gln Arg
20 25 30

Ile Gln Leu
35

<210> SEQ ID NO 44
<211> LENGTH: 19
<212> TYPE: PRT
<213> ORGANISM: Hepatitis C virus

<400> SEQUENCE: 44

Gly Trp Gly Pro Ile Thr Tyr Thr Glu Ser Gly Ser Arg Asp Gln Arg
1 5 10 15

Pro Tyr Cys

<210> SEQ ID NO 45
<211> LENGTH: 35
<212> TYPE: PRT
<213> ORGANISM: Hepatitis C virus

<400> SEQUENCE: 45

Ala Gly Val Asp Gly Glu Thr Tyr Thr Ser Gly Gly Ala Ala Ser His
1 5 10 15

Thr Thr Ser Thr Leu Ala Ser Leu Phe Ser Pro Gly Ala Ser Gln Arg
20 25 30

Ile Gln Leu
35

-continued

<210> SEQ ID NO 46
<211> LENGTH: 19
<212> TYPE: PRT
<213> ORGANISM: Hepatitis C virus

<400> SEQUENCE: 46

Gly Trp Gly Pro Ile Thr Tyr Thr Glu Pro Asp Ser Pro Asp Gln Arg
1 5 10 15

Pro Tyr Cys

<210> SEQ ID NO 47
<211> LENGTH: 341
<212> TYPE: DNA
<213> ORGANISM: Hepatitis C virus

<400> SEQUENCE: 47
gccagccccc gattgggggc gacactccac catagatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac c 341

<210> SEQ ID NO 48
<211> LENGTH: 341
<212> TYPE: DNA
<213> ORGANISM: Hepatitis C virus

<400> SEQUENCE: 48
gccagccccc tgatgggggc gacactccac catgaatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac c 341

<210> SEQ ID NO 49
<211> LENGTH: 341
<212> TYPE: DNA
<213> ORGANISM: Hepatitis C virus

<400> SEQUENCE: 49
gccagccccc tgatgggggc gacactccac catgaatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gataaacccg ctcaatgcct ggagatttgg gcgtgccccc 240
gcaagactgc tagccgagta gtgttgggtc gcgaaaggcc ttgtggtact gcctgatagg 300
gtgcttgcga gtgccccggg aggtctcgta gaccgtgcac c 341

<210> SEQ ID NO 50
<211> LENGTH: 41
<212> TYPE: DNA
<213> ORGANISM: Hepatitis C virus -continued

<400> SEQUENCE: 50
tgaacgggga gctaaccact ccaggccaat aggccttcct g 41

<210> SEQ ID NO 51
<211> LENGTH: 42
<212> TYPE: DNA
<213> ORGANISM: Hepatitis C virus

<400> SEQUENCE: 51
tgaacgggga gctaaccact ccaggcctta agccatttcc tg 42

<210> SEQ ID NO 52
<211> LENGTH: 43
<212> TYPE: DNA
<213> ORGANISM: Hepatitis C virus

<400> SEQUENCE: 52
tgaaggttgg ggtaaacact ccggcctctt aagccatttc ctg 43

<210> SEQ ID NO 53
<211> LENGTH: 16
<212> TYPE: DNA
<213> ORGANISM: Hepatitis C virus

<400> SEQUENCE: 53
ggtggctcca tcttag 16

<210> SEQ ID NO 54
<211> LENGTH: 19
<212> TYPE: DNA
<213> ORGANISM: Hepatitis C virus

<400> SEQUENCE: 54
aatggtggct ccatcttag 19

<210> SEQ ID NO 55
<211> LENGTH: 82
<212> TYPE: DNA
<213> ORGANISM: Hepatitis C virus

<400> SEQUENCE: 55
ccctagtcac ggctagctgt gaaaggtccg tgagccgcat gactgcagag agtgctgata 60
ctggcctctc tgcagatcat gt 82

<210> SEQ ID NO 56
<211> LENGTH: 40
<212> TYPE: DNA
<213> ORGANISM: Hepatitis C virus

<400> SEQUENCE: 56
aggttggggt aaacactccg gcctcttaag ccatttcctg 40

<210> SEQ ID NO 57
<211> LENGTH: 81
<212> TYPE: DNA
<213> ORGANISM: Hepatitis C virus

<400> SEQUENCE: 57
tttttttttt tttttttttt ttttttttct tttttttttt ctttcctttc cttctttttt 60
tcctttcttt ttcccttctt t 81

-continued

<210> SEQ ID NO 58
<211> LENGTH: 101
<212> TYPE: DNA
<213> ORGANISM: Hepatitis C virus

<400> SEQUENCE: 58
aatggtggct ccatcttagc cctagtcacg gctagctgtg aaaggtccgt gagccgcatg 60
actgcagaga gtgctgatac tggcctctct gcagatcatg t 101

<210> SEQ ID NO 59
<211> LENGTH: 127
<212> TYPE: DNA
<213> ORGANISM: Hepatitis C virus

<400> SEQUENCE: 59
tgaaggttgg ggtaaacact ccggcctctt aagccatttc ctgttttttt tttttttttt 60
tttttttttt tctttttttt tttctttcct ttccttcttt ttttcctttc tttttccctt 120
ctttaat 127

<210> SEQ ID NO 60
<211> LENGTH: 183
<212> TYPE: DNA
<213> ORGANISM: Hepatitis C virus

<400> SEQUENCE: 60
tgaaggttgg ggtaaacact ccggcctctt aagccatttc ctgttttttt tttttttttt 60
tttttttttt tctttttttt tttctttcct ttccttcttt ttttcctttc tttttccctt 120
ctttaatggt ggctccatct tagccctagt cacggctagc tgtgaaaggt ccgtgagccg 180
cat 183

<210> SEQ ID NO 61
<211> LENGTH: 52
<212> TYPE: DNA
<213> ORGANISM: Hepatitis C virus

<400> SEQUENCE: 61
tgagccgcat gactgcagag agtgctgata ctggcctctc tgcagatcat gt 52

<210> SEQ ID NO 62
<211> LENGTH: 105
<212> TYPE: DNA
<213> ORGANISM: Hepatitis C virus

<400> SEQUENCE: 62
tgaaattggt ggctccatct tagccctagt cacggctagc tgtgaaaggt ccgtgagccg 60
catgactgca gagagtgctg atactggcct ctctgcagat catgt 105

<210> SEQ ID NO 63
<211> LENGTH: 176
<212> TYPE: DNA
<213> ORGANISM: Hepatitis C virus

<400> SEQUENCE: 63
tgaaggttgg ggtaaacact ccggcctctt aagccatttc ctgttttttt tttttttttt 60
tttttttttt tctttttttt tttctttcct ttccttcttt ttttcctttc tttttccctt 120
ctttaatgcc gcatgactgc agagagtgct gatactggcc tctctgcaga tcatgt 176

<210> SEQ ID NO 64

-continued

```
<211> LENGTH: 200
<212> TYPE: DNA
<213> ORGANISM: Hepatitis C virus

<400> SEQUENCE: 64

tgacttaagc catttcctgt tttttttttt tttttttttt tttttttctt ttttttttttc     60

tttcctttcc ttcttttttt cctttctttt tcccttcttt aatggtggct ccatcttagc    120

cctagtcacg gctagctgtg aaaggtccgt gagccgcatg actgcagaga gtgctgatac    180

tggcctctct gcagatcatg                                                200


<210> SEQ ID NO 65
<211> LENGTH: 144
<212> TYPE: DNA
<213> ORGANISM: Hepatitis C virus

<400> SEQUENCE: 65

tgaaggttgg ggtaaacact ccggcctctt aagccatttc ctgaatggtg gctccatctt     60

agccctagtc acggctagct gtgaaaggtc cgtgagccgc atgactgcag agagtgctga    120

tactggcctc tctgcagatc atgt                                           144
```